United States Patent
McKinnell et al.

(10) Patent No.: US 10,851,102 B2
(45) Date of Patent: Dec. 1, 2020

(54) IMIDAZOLE AND TRIAZOLE CONTAINING BICYCLIC COMPOUNDS AS JAK INHIBITORS

(71) Applicant: THERAVANCE BIOPHARMA R&D IP, LLC, South San Francisco, CA (US)

(72) Inventors: Robert Murray McKinnell, South San Francisco, CA (US); Erik Fenster, South San Francisco, CA (US); Tom M. Lam, South San Francisco, CA (US); Anthony Francesco Palermo, South San Francisco, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

(21) Appl. No.: 16/749,035

(22) Filed: Jan. 22, 2020

(65) Prior Publication Data
US 2020/0231590 A1    Jul. 23, 2020

Related U.S. Application Data

(60) Provisional application No. 62/795,699, filed on Jan. 23, 2019.

(51) Int. Cl.
| | |
|---|---|
| *C07D 471/04* | (2006.01) |
| *C07D 487/04* | (2006.01) |
| *A61K 9/00* | (2006.01) |
| *C07D 487/08* | (2006.01) |
| *A61P 1/00* | (2006.01) |
| *C07D 471/08* | (2006.01) |

(52) U.S. Cl.
CPC .......... *C07D 471/04* (2013.01); *A61K 9/0014* (2013.01); *A61P 1/00* (2018.01); *C07D 471/08* (2013.01); *C07D 487/04* (2013.01); *C07D 487/08* (2013.01)

(58) Field of Classification Search
CPC ............................ C07D 471/04; A61K 9/0014
See application file for complete search history.

(56) References Cited

U.S. PATENT DOCUMENTS

| | | |
|---|---|---|
| 8,377,946 B1 | 2/2013 | Chen et al. |
| 8,648,069 B2 | 2/2014 | Kkritopoulou-Zanze |
| 9,163,007 B2 | 10/2015 | Kkritopoulou-Zanze et al. |
| 9,518,052 B2 | 12/2016 | Coe et al. |
| 9,617,258 B2 | 4/2017 | Thorarensen et al. |
| 9,695,168 B2 * | 7/2017 | Wu ................. C07D 487/04 |
| 10,047,086 B2 * | 8/2018 | Wu ................. C07D 519/00 |
| 10,392,368 B2 * | 8/2019 | Fenster .............. A61P 35/00 |
| 10,538,513 B2 * | 1/2020 | McKinnell .......... A61P 29/00 |
| 2003/0139427 A1 | 7/2003 | Castelhano et al. |
| 2007/0104780 A1 | 5/2007 | Lipari et al. |
| 2012/0238559 A1 | 9/2012 | Baldwin et al. |
| 2012/0245170 A1 | 9/2012 | Bedjeguelal et al. |
| 2013/0065894 A1 | 3/2013 | Loehn et al. |
| 2013/0085128 A1 | 4/2013 | Hachtel et al. |
| 2013/0150340 A1 | 6/2013 | Plettenburg et al. |
| 2014/0349998 A1 | 11/2014 | Ahearn et al. |
| 2015/0158864 A1 | 6/2015 | Thorarensen et al. |
| 2015/0329542 A1 | 11/2015 | Coe et al. |
| 2017/0071946 A1 | 3/2017 | Coe et al. |
| 2018/0064621 A1 | 3/2018 | Salce, Jr. et al. |
| 2018/0117148 A1 | 5/2018 | Holman |
| 2019/0040043 A1 | 2/2019 | Fenster et al. |

FOREIGN PATENT DOCUMENTS

| | | |
|---|---|---|
| CN | 105837574 A | 8/2016 |
| EP | 2567959 A1 | 3/2013 |
| JP | 2009007342 A | 1/2009 |
| WO | 02/085853 A2 | 10/2002 |
| WO | 03/078403 A2 | 9/2003 |
| WO | 2004/113304 A1 | 12/2004 |

(Continued)

OTHER PUBLICATIONS

U.S. Appl. No. 16/688,109, unpublished, McKinnell et al.
Abcouwer, "Angiogenic factors and cytokines in diabetic retinopathy", J Clin Cell Immunol, Supplement 1: 1-12 (2013).
Bao et al., "The involvement of the JAK-STAT signaling pathway in chronic inflammatory skin disease atopic dermatitis", JAK-STAT, 2(3): e24137-1-e24137-8 (2013).
The International Search Report and the Written Opinion for PCT application No. PCT/US2020/014525 dated Apr. 30, 2020.

(Continued)

*Primary Examiner* — Golam M Shameem
(74) *Attorney, Agent, or Firm* — Jeffrey A. Hagenah; Florence Jovic

(57) ABSTRACT

The invention provides compounds of formula (I):

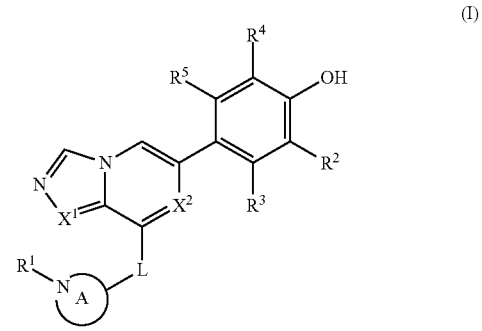

or a pharmaceutically-acceptable salt thereof, wherein the variables are defined in the specification, that are inhibitors of JAK kinases, particularly JAK3. The invention also provides pharmaceutical compositions comprising such compounds, and methods of using such compounds to treat gastrointestinal and other inflammatory diseases.

19 Claims, No Drawings

(56) References Cited

FOREIGN PATENT DOCUMENTS

| | | |
|---|---|---|
| WO | 2006/040351 A1 | 4/2006 |
| WO | 2007/117995 A2 | 10/2007 |
| WO | 2009/147188 A1 | 12/2009 |
| WO | 2009/147189 A1 | 12/2009 |
| WO | 2009/147190 A1 | 12/2009 |
| WO | 2010/012121 A1 | 2/2010 |
| WO | 2011/014817 A1 | 2/2011 |
| WO | 2011/031554 A2 | 3/2011 |
| WO | 2011/067365 A1 | 6/2011 |
| WO | 2011/112766 A2 | 9/2011 |
| WO | 2012/061537 A1 | 5/2012 |
| WO | 2013/037390 A1 | 3/2013 |
| WO | 2013/057253 A1 | 4/2013 |
| WO | 2013/149194 A1 | 10/2013 |
| WO | 2013/167403 A1 | 11/2013 |
| WO | 2014/039595 A1 | 3/2014 |
| WO | 2014/140065 A1 | 9/2014 |
| WO | 2015/083028 A1 | 6/2015 |
| WO | 2015/112445 A1 | 7/2015 |
| WO | 2015/173683 A1 | 11/2015 |
| WO | 2016/007731 A1 | 1/2016 |
| WO | 2016/011394 A1 | 1/2016 |
| WO | 2016/071293 A2 | 5/2016 |
| WO | 2016/178110 A1 | 11/2016 |
| WO | 2016/179605 A1 | 11/2016 |
| WO | 2017/077283 A1 | 5/2017 |
| WO | 2017/077288 A1 | 5/2017 |
| WO | 2017/143014 A1 | 8/2017 |
| WO | 2018/004306 A1 | 1/2018 |
| WO | 2018/036414 A1 | 1/2018 |
| WO | 2018/075937 A1 | 4/2018 |
| WO | 2018/098491 A1 | 5/2018 |
| WO | 2018/169373 A1 | 9/2018 |
| WO | 2019/090158 A1 | 5/2019 |
| WO | 2019/132560 A1 | 7/2019 |
| WO | 2019/132561 A1 | 7/2019 |
| WO | 2019/132562 A1 | 7/2019 |
| WO | 2019/182924 A1 | 9/2019 |

OTHER PUBLICATIONS

Coghill et al., "Effector CD4+ T cells, the cytokines they generate, and GVHD: something old and something new", Blood, 117(12): 3268-3276 (Mar. 24, 2011).
Craiglow et al., "Tofacitinib citrate for the treatment of vitiligo: A pathogenesis-directed therapy", JAMA Dermatology, 151: 1110-1112 (2015).
De Nitto et al., "Involvement of interleukin-15 and interleukin-21, two gamma-chain-related cytokines, in celiac disease", World J Gastroenterol, 15(37): 4609-4614 (Oct. 7, 2009).
Feliciani et al., "A TH2-like cytokine response is involved in bullous pemphigoid. The role of IL-4 and IL-5 in the pathogenesis of the disease", International Journal of Immunopathology and Pharmacology, 12(2): 55-61 (1999).
Forster et al., "Selective JAK3 inhibitors with a covalent reversible binding mode targeting a new induced fit binding pocket", Cell Chemical Biology, 23: 1335-1340 (2016).
Goedken et al., "Tricyclic covalent inhibitors selectively target JAK3 through an active site Thiol", J. Biol. Chem., 290 (8): 4573-4589 (2015).
Horai et al, "Cytokines in autoimmune uveitis", Journal of Interferon & Cytokine Research, 31(10): 733-744 (2011).
Knickelbein et al., "Inflammatory mechanisms of age-related macular degeneration", International Ophthalmology Clinics, 55(3): 63-78 (2015).
Kudlacz et al., "The JAK-3 inhibitor CP-690550 is a potent anti-inflammatory agent in a murine model of pulmonary eosinophilia", European Journal of Pharmacology, 582: 154-161 (2008).
Kumawat et al., "Microscopic colitis patients demonstrate a mixed Th17/Tc17 and Th1/Tc1 mucosal cytokine profile", Molecular Immunology, 55: 355-364 (2013).

Liu et al., "Developing irreversible inhibitors of the protein kinase cysteinome", Chemistry & Biology, 20: 146-159 (2013).
Lynch et al., "Strategic use of conformational bias and structure based design to identify potent JAK3 inhibitors with improved selectivity against the JAK family and the kinome", Bioorganic & Medicinal Chemistry Letters, 23: 2793-2800 (2013).
Malaviya et al., "Janus Kinase-3 dependent inflammatory responses in allergic asthma", International Immunopharmacology, 10: 829-836 (2010).
Matsunaga et al., "Effects of a Janus kinase inhibitor, pyridone 6, on airway responses in a murine model of asthma", Biochemical and Biophysical Research Communications, 404: 261-267 (2011).
Netchiporouk et al., "Deregulation in STAT signaling is important for cutaneous T-cell lymphoma (CTCL) pathogenesis and cancer progression", Cell Cycle, 13(21): 3331-3335 (Nov. 1, 2014).
Okiyama et al., "Reversal of CD8 T-cell-mediated mucocutaneous graft-versus-host-like disease by the JAK inhibitor tofacitinib", Journal of Investigative Dermatology, 134: 992-1000 (2014).
Reimund et al., "Mucosal inflammatory cytokine production by intestinal biopsies in patients with ulcerative colitis and Crohn's disease", Journal of Clinical Immunology, 16(3): 144-150 (1996).
Ritzen et al., "Fragment-based discovery of 6-Arylindazole JAK inhibitors", ACS Medicinal Chemistry Letters, 7: 641-646 (2016).
Scott, "Tofacitinib: A review of its use in adult patients with rheumatoid arthritis", Drugs, 73: 857-874 (2013).
Shchuko et al., "Intraocular cytokines in retinal vein occlusion and its relation to the efficiency of anti-vascular endothelial growth factor therapy", Indian Journal of Ophthalmology, 63: 905-911 (2015).
Sohn et al., "Changes in aqueous concentrations of various cytokines after intravitreal triamcinolone versus bevacizumab for diabetic macular edema", Ophthalmology, 152: 686-694 (2011).
Sonkoly et al., "IL-31: A new link between T cells and pruritus in atopic skin inflammation", J Allergy Clin Immunol, 117(2): 411-417 (2006).
Soth et al., "3-Amido pyrrolopyrazine JAK kinase inhibitors: Development of a JAK3 vs JAK1 selective inhibitor and evaluation in cellular and in vivo models", Journal of Medicinal Chemistry, 56: 345-356 (2013).
Stallmach et al., "Cytokine/chemokine transcript profiles reflect mucosal inflammation in Crohn's disease", Int J Colorectal Dis, 19: 308-315 (2004).
Stevenson et al., "Dry eye disease", Arch Ophthalmol, 130(1): 90-100 (Jan. 2012).
Tan et al., "Development of selective covalent janus kinase 3 inhibitors", J. Med. Chem., 58: 6589-6606 (2015).
Tanaka et al., "New insight into mechanisms of pruritus from molecular studies on familial primary localized cutaneous amyloidosis", British Journal of Dermatology, 161: 1217-1224 (2009).
Telliez et al., "Discovery of a JAK3-selective inhibitor: Functional differentiation of JAK3-selective inhibition over pan-JAK or JAK1-selective inhibition", ACS Chemical Biology, 11: 3442-3451 (2016).
Thorarensen et al., "Design of a Janus Kinase 3 (JAK3) specific inhibitor 1-((2S,5R)-54(7H-Pyrrolo[2,3-d] pyrimidin-4-yl)amino)-2-methylpiperidin-1-yl)prop-2-en-1-one (PF-06651600) allowing for the interrogation of JAK3 signaling in humans", Journal of Medicinal Chemistry, 60: 1971-1993 (2017).
Weinbrand-Goichberg et al., "Eosinophilic esophagitis: an immune-mediated esophageal disease", Immunol Res, 56: 249-260 (2013).
Welz-Kubiak et al., "IL-31 is overexpressed in lichen planus but its level does not correlate with pruritus severity", Journal of Immunology Research, Article 854747, 6 pages (2015).
Woywodt et al., "Mucosal cytokine expression, cellular markers and adhesion molecules in inflammatory bowel disease", European Journal of Gastroenterology & Hepatology, 11: 267-276 (1999).
Xing et al., "Alopecia areata is driven by cytotoxic T lymphocytes and is reversed by JAK inhibition", Nature Medicine, 20(9): 1043-1049 (Sep. 2014).
Yamamoto et al., "Mucosal inflammation in the terminal ileum of ulcerative colitis patients: Endoscopic findings and cytokine profiles", Digestive and Liver Disease, 40: 253-259 (2008).

(56) References Cited

OTHER PUBLICATIONS

Yano et al., "Ipilimumab augments antitumor activity of bispecific antibody-armed T cells", Journal of Translational Medicine, 12: 191 (2014).

Zhou et al., "Cytokines and Behcet's Disease", Autoimmunity Reviews, 11: 699-704 (2012).

* cited by examiner

IMIDAZOLE AND TRIAZOLE CONTAINING BICYCLIC COMPOUNDS AS JAK INHIBITORS

CROSS-REFERENCE TO RELATED APPLICATIONS

This application claims the benefit of U.S. Provisional Application No. 62/795,699, filed on Jan. 23, 2019, the disclosure of which is incorporated herein by reference in its entirety.

BACKGROUND

Field

The invention is directed to imidazole and triazole containing bicyclic compounds useful as JAK kinase inhibitors and more particularly as JAK3 inhibitors that are selective for JAK3 over other members of the JAK kinase family such as JAK1, JAK2 and TYK2. The invention is also directed to pharmaceutical compositions comprising such compounds, and methods of using such compounds to treat inflammatory diseases.

State of the Art

Ulcerative colitis is a chronic inflammatory disease of the colon. The disease is characterized by inflammation and ulceration of the mucosal layer of the rectum and the large intestine. Common symptoms include diarrhea, bloody stools, and abdominal pain. The clinical course is intermittent, marked by alternating periods of exacerbation and remission. Incidence seems to be greater in developed than in developing countries. An estimated 1.2 million people in major industrialized countries suffer from ulcerative colitis and the numbers are expected to increase along with population growth. Patients with ulcerative colitis are at an increased risk of developing colorectal cancer (e.g., Danese et al. *N Engl J Med*, 2011, 365, 1713-1725). Although there exists a variety of therapeutic options to promote and maintain remission of ulcerative colitis (UC) in patients, none is ideal. There remains an unmet medical need for an effective therapy to promote and maintain remission of moderate to severe UC without the safety concerns resulting from chronic, systemic immunosuppression.

Although the precise pathogenesis of UC is unclear, it is apparent that proinflammatory cytokines play a pivotal role in the immunological response (Strober et al., *Gastroenterol*, 2011, 140, 1756-1767). Many of the proinflammatory cytokines most commonly elevated in UC (e.g., IL-4, IL-6, IL-13, IL-15, IL-23, IL-24, IFNγ and leptin), rely on the JAK family of tyrosine kinases (i.e., JAK1, JAK2, JAK3 and TYK2) for signal transduction.

Inhibition of the JAK3 enzyme blocks the signaling of many key pro-inflammatory cytokines. Thus JAK3 inhibitors are likely to be useful in the treatment of ulcerative colitis and other gastrointestinal inflammatory diseases such as Crohn's disease and immune checkpoint inhibitor induced colitis. JAK3 inhibitors are also likely to be useful for the treatment of inflammatory skin diseases such as atopic dermatitis and inflammatory respiratory disorders such as allergic rhinitis, asthma, and chronic obstructive pulmonary disease (COPD). In addition, JAK3 inhibitors may also be useful in the treatment of many ocular diseases for which inflammation plays a prominent role such as uveitis, diabetic retinopathy, diabetic macular edema, dry eye disease, age-related macular degeneration, retinal vein occlusion (RVO) and atopic keratoconjunctivitis.

Selectivity for JAK3 over JAK1 is anticipated to be beneficial as there is evidence that JAK3 selectivity allows sparing of potentially beneficial cytokines such as IL-10 which has been involved in mucosal healing, IL-22 which is involved in mucus barrier protection and epithelial regeneration, and IL-6 which is involved in the proliferation of intestinal epithelial cells. Selectivity for JAK3 over JAK2 also allows sparing of erythropoietin (EPO) and thrombopoietin (TPO) signaling. Therefore, it would be desirable to provide new compounds which are selective JAK3 inhibitors over other members of the JAK kinase family such as JAK1, JAK2 and TYK2.

Finally, due to the modulating effect of the JAK/STAT pathway on the immune system, systemic exposure to JAK inhibitors may have an adverse systemic immunosuppressive effect. It would be desirable, therefore, to provide new JAK3 inhibitors which have their effect at the site of action without significant systemic effects. In particular, for the treatment of gastrointestinal inflammatory diseases, such as ulcerative colitis, it would be desirable to provide new JAK3 inhibitors which can be administered orally and achieve therapeutically relevant exposure in the gastrointestinal tract with minimal systemic exposure. For skin diseases, it would be desirable to provide new JAK3 inhibitors that could be administered topically to the skin with minimal systemic exposure.

Therefore, it would be desirable to provide new compounds which are selective JAK3 inhibitors over other members of the JAK kinase family such as JAK1, JAK2 and TYK2, and have minimal systemic exposure.

SUMMARY

In one aspect, the invention provides novel compounds having activity as JAK kinase inhibitors and more particularly as JAK3 inhibitors.

Accordingly, the invention provides a compound of formula (I):

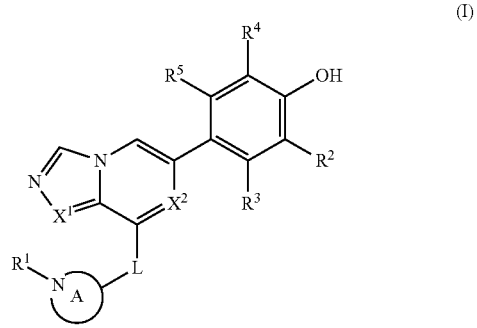

or a pharmaceutically acceptable salt thereof, wherein
$X^1$ and $X^2$ are each independently selected from N and CH;

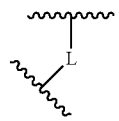

is selected from the group consisting of

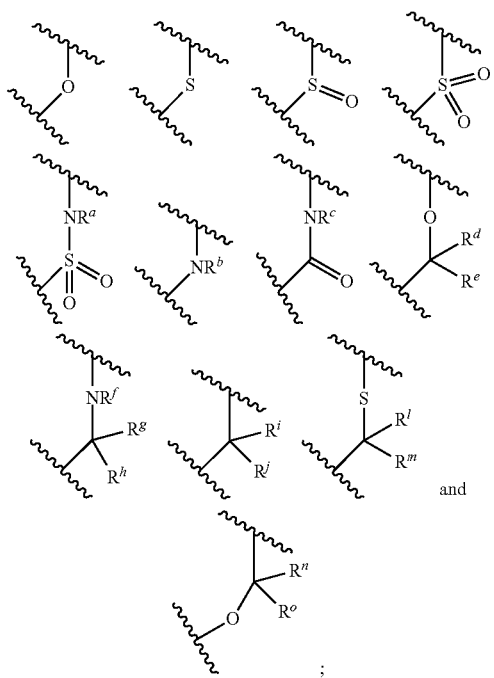

$R^a$, $R^b$, $R^c$, and $R^f$ are each independently selected from the group consisting of H and $C_{1-3}$ alkyl;

$R^d$, $R^e$, $R^g$, $R^h$, $R^i$, $R^j$, $R^l$, $R^m$, and $R^o$ are each independently selected from the group consisting of H and $C_{1-3}$ alkyl wherein the $C_{1-3}$ alkyl group may be optionally substituted with 1 to 3 halogens;

A is selected from the group consisting of (a) a 4 to 8 membered monocyclic heterocyclic group containing one nitrogen atom and optionally containing one additional heteroatom selected from N, S, $S(O)_2$ and O, and (b) a 6 to 10 membered multicyclic heterocyclic group containing one nitrogen atom and optionally containing one additional heteroatom selected from N, S, $S(O)_2$ and O, wherein L is linked to a carbon atom in A and A is optionally substituted with 1 to 3 $R^k$ groups;

each $R^k$ is independently selected from the group consisting of F, CN, $C_{1-3}$ alkoxy, and $C_{1-3}$ alkyl, wherein the $C_{1-3}$ alkyl group may be optionally substituted with OH, OMe or 1 to 3 halogens;

$R^1$ is selected from the group consisting of:

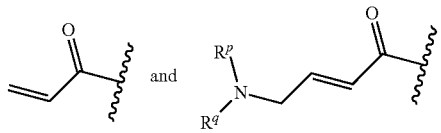

wherein $R^p$ and $R^q$ are each independently selected from the group consisting of H, $C_{3-5}$ cycloalkyl and $C_{1-6}$ alkyl;

$R^2$ is selected from the group consisting of H, Cl, OMe, Me and F;

$R^3$ is selected from the group consisting of H, Me, Et, $CF_3$, OMe, and F;

$R^4$ is selected from the group consisting of H, Me, OMe, Cl, and F; and $R^5$ is selected from the group consisting of H, Me, Et, and F.

The invention also provides a pharmaceutical composition comprising a compound of the disclosure, or a pharmaceutically acceptable salt thereof, and a pharmaceutically-acceptable carrier.

The invention also provides a method of treating a gastrointestinal inflammatory disease in a mammal, the method comprising administering to the mammal a compound of the disclosure, or a pharmaceutically acceptable salt thereof, or a pharmaceutical composition of the disclosure.

The invention also provides a method of treating inflammatory diseases or disorders of the skin in a mammal, the method comprising applying a compound of the disclosure, or a pharmaceutically acceptable salt thereof, or a pharmaceutical composition of the disclosure to the skin of the mammal.

The invention also provides a method of treating cutaneous T-cell lymphoma in a mammal, the method comprising applying a pharmaceutical composition comprising a compound of the disclosure, or a pharmaceutically acceptable salt thereof, to the skin of the mammal.

The invention also provides a compound of the disclosure or a pharmaceutically acceptable salt thereof, as described herein for use in medical therapy, as well as the use of a compound of the disclosure, or a pharmaceutically acceptable salt thereof, in the manufacture of a formulation or medicament for treating a gastrointestinal inflammatory disease, or an inflammatory disease of the skin in a mammal.

DETAILED DESCRIPTION

Among other aspects, the invention provides JAK kinase inhibitors of formula (I) which are selective for JAK3 over other members of the JAK kinase family such as JAK1, JAK2 and TYK2, and pharmaceutically-acceptable salts thereof.

In one aspect, the invention provides compounds having activity as JAK kinase inhibitors, particularly as JAK3 kinase inhibitors.

Accordingly, the invention provides a compound of formula (I):

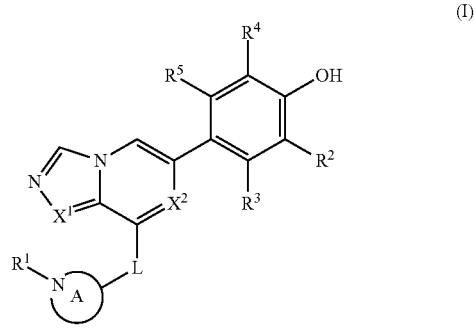

or a pharmaceutically acceptable salt thereof, wherein
$X^1$ and $X^2$ are each independently selected from N and CH;

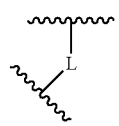

is selected from the group consisting of

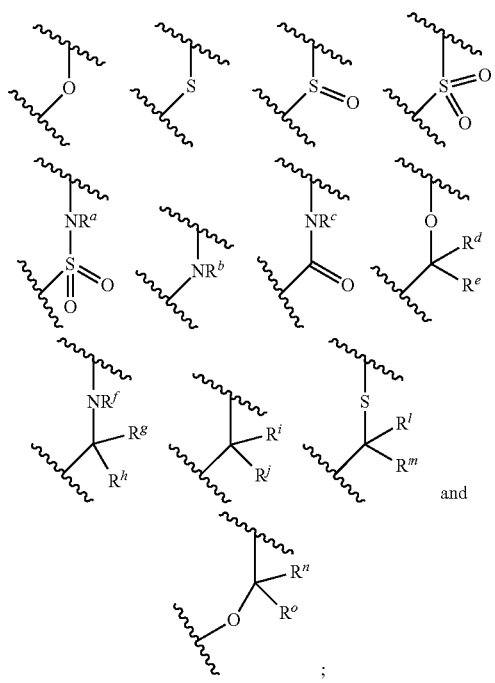

;

$R^a$, $R^b$, $R^c$, and $R^f$ are each independently selected from the group consisting of H and $C_{1-3}$ alkyl;

$R^d$, $R^e$, $R^g$, $R^h$, $R^i$, $R^j$, $R^l$, $R^m$, $R^n$ and $R^o$ are each independently selected from the group consisting of H and $C_{1-3}$ alkyl wherein the $C_{1-3}$ alkyl group may be optionally substituted with 1 to 3 halogens;

A is selected from the group consisting of (a) a 4 to 8 membered monocyclic heterocyclic group containing one nitrogen atom and optionally containing one additional heteroatom selected from N, S, $S(O)_2$ and O, and (b) a 6 to 10 membered multicyclic heterocyclic group containing one nitrogen atom and optionally containing one additional heteroatom selected from N, S, $S(O)_2$ and O, wherein L is linked to a carbon atom in A and A is optionally substituted with 1 to 3 $R^k$ groups;

each $R^k$ is independently selected from the group consisting of F, CN, $C_{1-3}$ alkoxy, and $C_{1-3}$ alkyl, wherein the $C_{1-3}$ alkyl group may be optionally substituted with OH, OMe or 1 to 3 halogens;

$R^1$ is selected from the group consisting of:

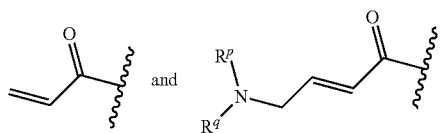

wherein $R^p$ and $R^q$ are each independently selected from the group consisting of H, $C_{3-5}$ cycloalkyl and $C_{1-6}$ alkyl;

$R^2$ is selected from the group consisting of H, Cl, OMe, Me and F;

$R^3$ is selected from the group consisting of H, Me, Et, $CF_3$, OMe, and F;

$R^4$ is selected from the group consisting of H, Me, OMe, Cl, and F; and $R^5$ is selected from the group consisting of H, Me, Et, and F.

In some embodiments, the compound has the Formula (II):

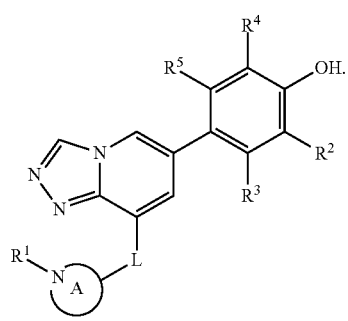

(II)

In some embodiments, the compound has the Formula (III):

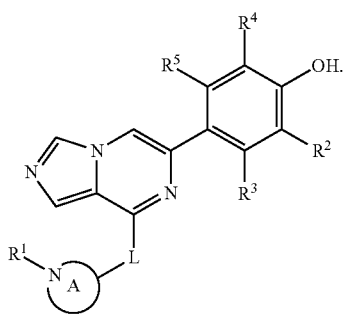

(III)

In some embodiments, the compound has the Formula (IV):

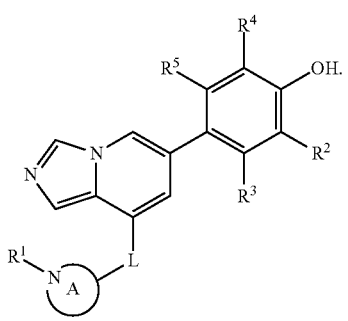

(IV)

In some embodiments, $R^1$ is selected from the group consisting of:

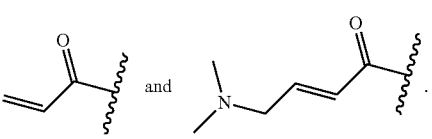

.

In some embodiments, $R^1$ is

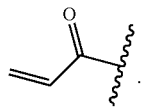 [SMILES: *C(=O)C=C]

In some embodiments, A is selected from the group consisting of azetidine, pyrrolidine, piperidine, 2-azaspiro[3.3]heptane, and nortropane, wherein A is optionally substituted with 1 to 3 $R^k$ groups. In some embodiments, A is selected from the group consisting of azetidine and piperidine, wherein A is optionally substituted with 1 to 3 $R^k$ groups. In some embodiments, A is an azetidine optionally substituted with 1 to 3 $R^k$ groups. In some embodiments, A is a piperidine optionally substituted with 1 to 3 $R^k$ groups.

In some embodiments,

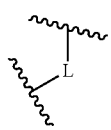

is selected from the group consisting of

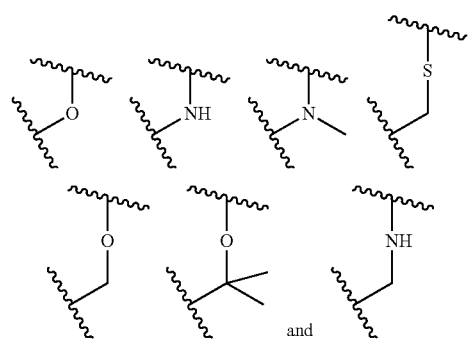

and

In some embodiments,

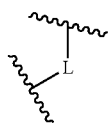

is selected from the group consisting of

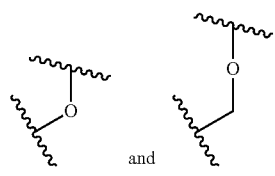

and .

In some embodiments,

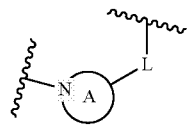

is selected from the group consisting of:

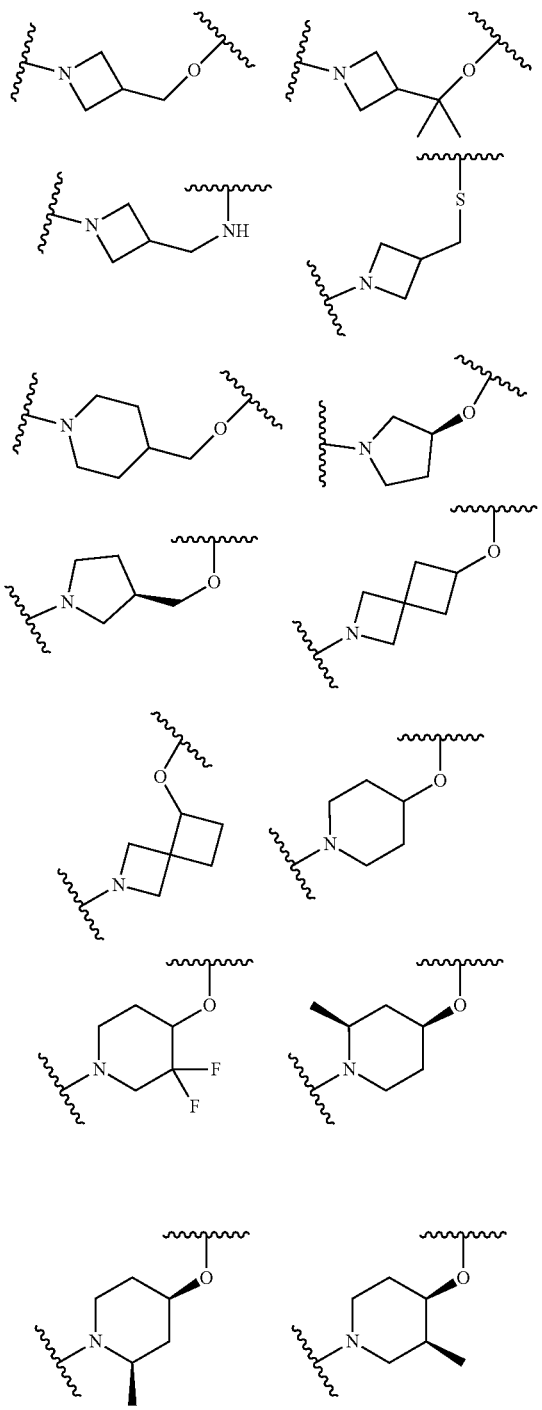

-continued
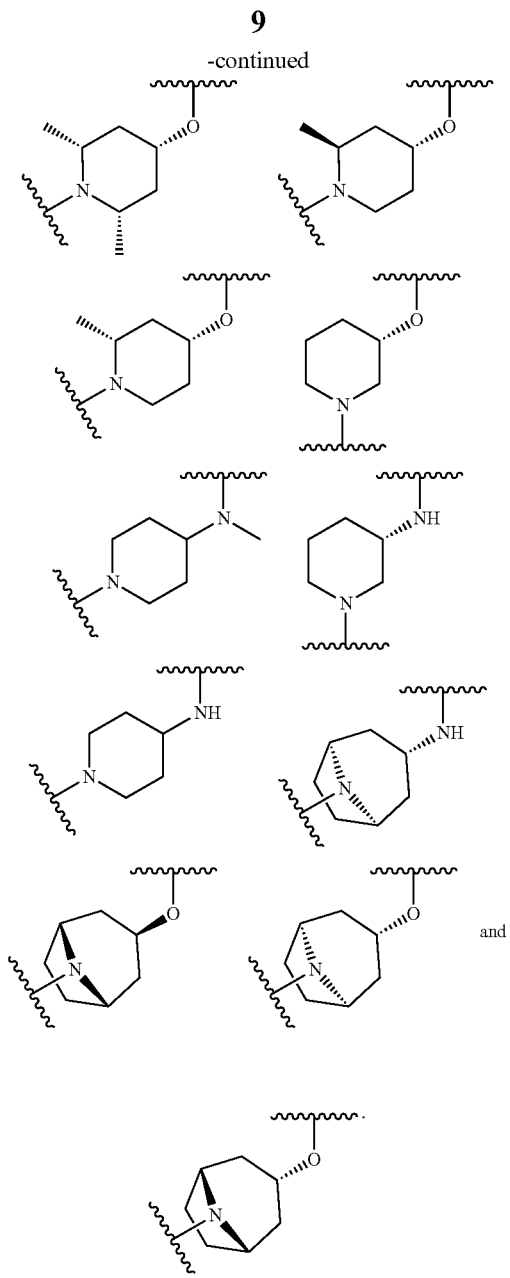
In some embodiments,
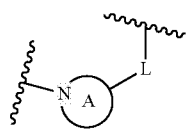
is selected from the group consisting of:
-continued
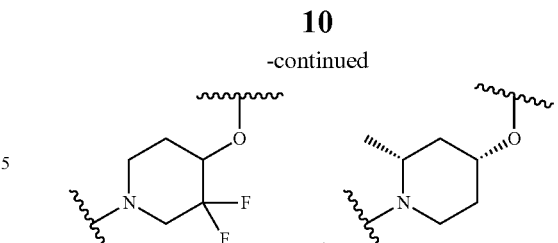
In some embodiments,
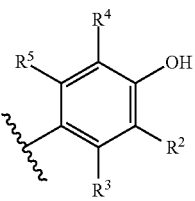
is selected from the group consisting of:
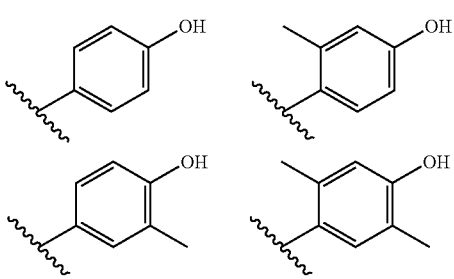
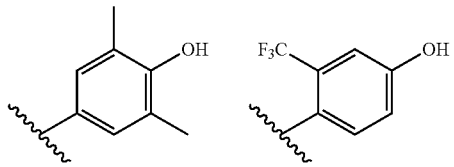
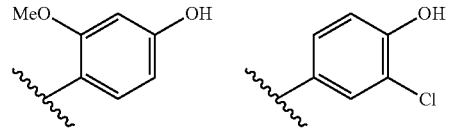
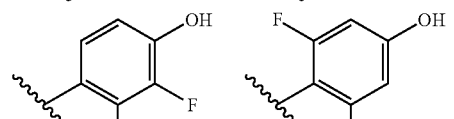
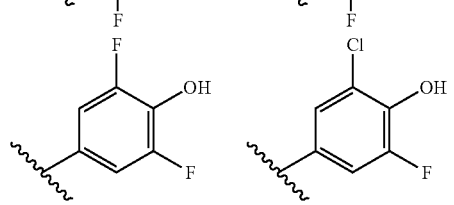
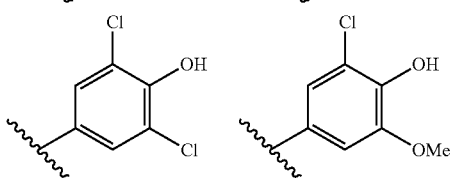

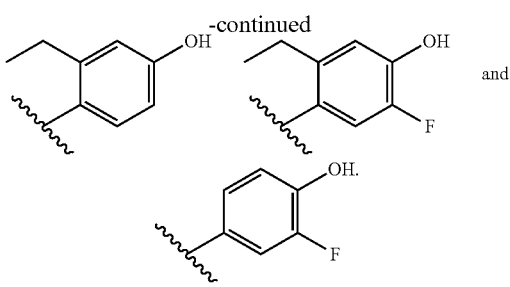
and

In some embodiments,

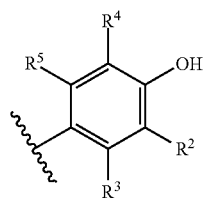

is selected from the group consisting of:

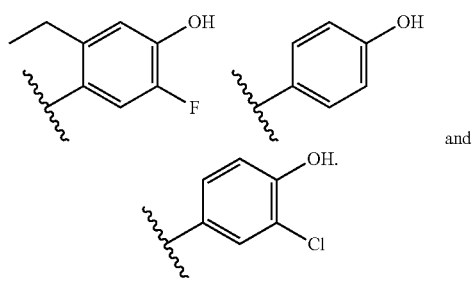
and

In some embodiments,

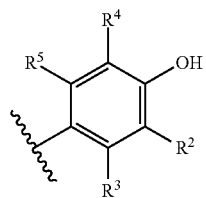

is selected from the group consisting of:

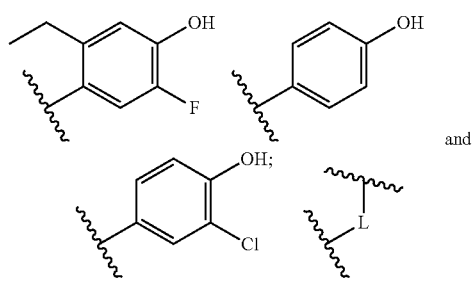
and is selected from the group consisting of

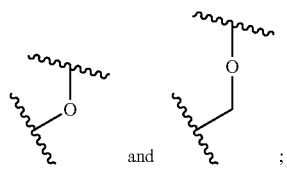
and ;

$R^1$ is

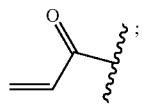 [SMILES: *C(=O)C=C]
;

and

A is selected from the group consisting of azetidine and piperidine, wherein A is optionally substituted with 1 or 2 $R^k$ groups, wherein each $R^k$ is independently selected from the group consisting of methyl and fluoro.

In some embodiments, the invention provides a compound selected from the group consisting of:

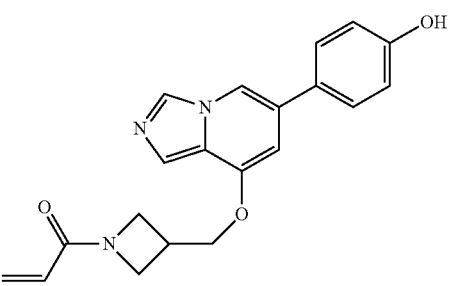

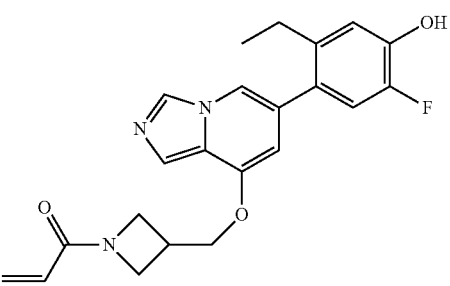

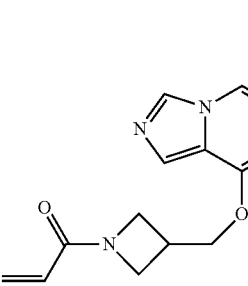

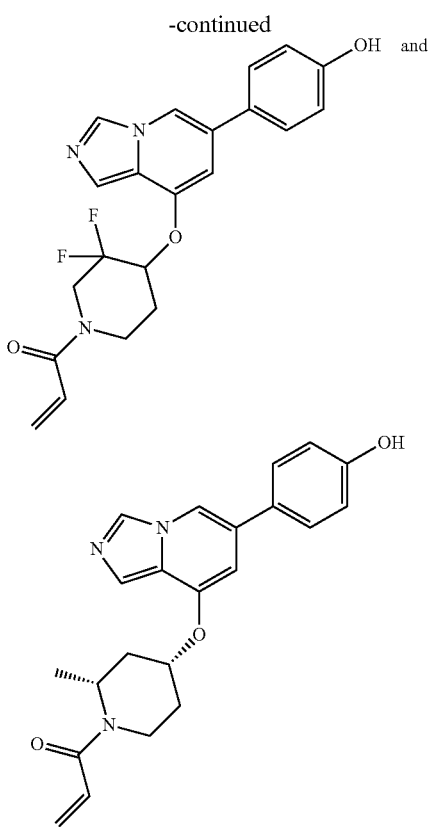

or pharmaceutically acceptable salts thereof.

The invention also provides a pharmaceutical composition comprising a compound of the disclosure, or a pharmaceutically acceptable salt thereof, and a pharmaceutically-acceptable carrier. In some embodiments, the pharmaceutical composition further comprises one or more other therapeutic agents. In some embodiments, the one or more other therapeutic agent is useful for treating a gastrointestinal inflammatory disease, an inflammatory disease of the skin, an inflammatory disease of the lungs or an inflammatory disease of the eye. In some embodiments, the one or more other therapeutic agent is useful for treating a gastrointestinal inflammatory disease. In some embodiments the gastrointestinal inflammatory disease is ulcerative colitis. In some embodiments the gastrointestinal inflammatory disease is Crohn's disease. In some embodiments the gastrointestinal inflammatory disease is celiac disease.

Furthermore, some compounds may sometimes exist in tautomeric forms. It will be understood that although structures are shown, or named, in a particular form, the invention also includes the tautomer thereof. Also, some compounds may sometimes exist in atropoisomeric forms. It will be understood that although structures are shown in a particular form, the invention also includes the corresponding atropoisomeric forms thereof.

The compounds of the invention may contain one or more chiral centers and therefore, such compounds (and intermediates thereof) can exist as racemic mixtures; scalemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

This invention also includes isotopically-labeled compounds of the disclosure, for example isotopically-labeled compounds of formula (I), (II), (III), (IV), i.e., compounds of the disclosure and compounds of formula (I), (II), (III), (IV), where one or more atom has been replaced or enriched with an atom having the same atomic number but an atomic mass different from the atomic mass that predominates in nature. Examples of isotopes that may be incorporated into a compounds of the disclosure and a compound of formula (I), (II), (III), (IV), include, but are not limited to, $^{2}H$, $^{3}H$, $^{11}C$, $^{13}C$, $^{14}C$, $^{13}N$, $^{15}N$, $^{15}O$, $^{17}O$, $^{18}O$, $^{35}S$, and $^{18}F$. Of particular interest are compounds of the disclosure and compounds of formula (I), (II), (III), (IV), enriched in tritium or carbon-14, which compounds can be used, for example, in tissue distribution studies. Also of particular interest are compounds of the disclosure and compounds of formula (I), (II), (III), (IV), enriched in deuterium especially at a site of metabolism, which compounds are expected to have greater metabolic stability. Additionally, of particular interest are compounds of the disclosure and compounds of formula (I), (II), (III), (IV), enriched in a positron emitting isotope, such as $^{11}C$, $^{18}F$, $^{15}O$ and $^{13}N$, which compounds can be used, for example, in Positron Emission Tomography (PET) studies.

Definitions

When describing this invention including its various aspects and embodiments, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like.

The term "haloalkyl" refers to an alkyl group, as defined above, that is substituted by one or more halogen, e.g., trifluoromethyl, difluoromethyl, trichloromethyl, 2,2,2 trifluoroethyl, 1,2 difluoroethyl, 3 bromo 2 fluoropropyl, 1,2 dibromoethyl, and the like.

When a specific number of carbon atoms are intended for a particular term, the number of carbon atoms is shown preceding the term. For example, the term "$C_{1-3}$alkyl" means an alkyl group having from 1 to 3 carbon atoms wherein the carbon atoms are in any chemically-acceptable configuration, including linear or branched configurations.

The term "alkoxy" means the monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl, cyclopentyl, cyclohexyl, cycloheptyl, cyclooctyl, adamantyl, and the like.

The term "heterocycle", "heterocyclic", or "heterocyclic ring" means a saturated or partially unsaturated cyclic non-aromatic group, having from 3 to 10 total ring atoms, wherein the ring contains from 2 to 9 carbon ring atoms and from 1 to 4 ring heteroatoms selected from nitrogen, oxygen, and sulfur. Heterocyclic groups may be monocyclic or multicyclic (i.e., fused, spiro or bridged). When the heterocyclic group is multicyclic, at least one but not necessarily all of the cyclic groups contains a heteroatom. Representative heterocyclic groups include, by way of example, pyrrolidinyl, piperidinyl, piperazinyl, imidazolidinyl, morpholinyl, thiomorpholyl, indolin-3-yl, 2-imidazolinyl, tetrahydropyranyl, 1,2,3,4-tetrahydroisoquinolin-2-yl, quinuclidinyl, 7-azanorbornanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, tetrahydropyran etc.

The term "therapeutically effective amount" means an amount sufficient to effect treatment when administered to a patient in need of treatment.

The term "treatment" as used herein means the treatment of a disease, disorder, or medical condition (such as a gastrointestinal inflammatory disease), in a patient, such as a mammal (particularly a human) which includes one or more of the following:

(a) preventing the disease, disorder, or medical condition from occurring, i.e., preventing the reoccurrence of the disease or medical condition or prophylactic treatment of a patient that is pre-disposed to the disease or medical condition;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS), triisopropylsilyl (TIPS), tert-butyldimethylsilyl (TBS or TBDMS), [2-(trimethylsilyl)-ethoxy]methyl (SEM); and the like. Numerous protecting groups, and their introduction and removal, are described in T. W. Greene and P. G. M. Wuts, *Protecting Groups in Organic Synthesis*, Third Edition, Wiley, N.Y.

General Synthetic Procedures

Compounds of this disclosure, and intermediates thereof, can be prepared according to the following general methods and procedures using commercially-available or routinely-prepared starting materials and reagents. The substituents and variables (e.g., A, $X^1$, $X^2$, $R^1$, $R^2$, $R^3$, $R^4$, $R^5$ etc.) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present invention may be shown or described in the following procedures, those skilled in the art will recognize that other embodiments or aspects of the present invention can also be prepared using such procedures or by using other methods, reagents, and starting materials known to those skilled in the art. In particular, it will be appreciated that compounds of the disclosure may be prepared by a variety of process routes in which reactants are combined in different orders to provide different intermediates en route to producing final products.

A general method of preparing final compounds of the disclosure wherein L is selected from:

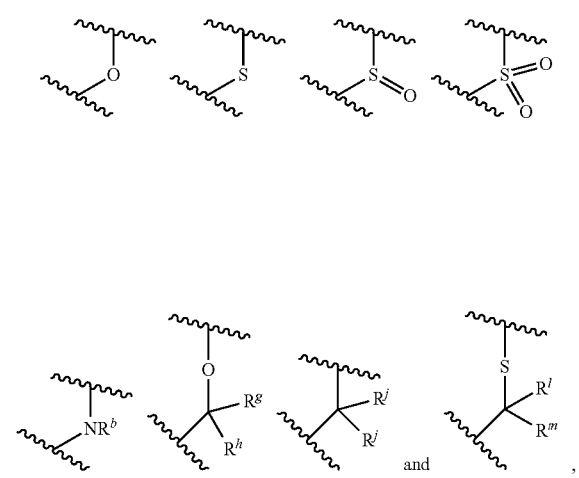

is illustrated in Scheme 1.

Scheme 1

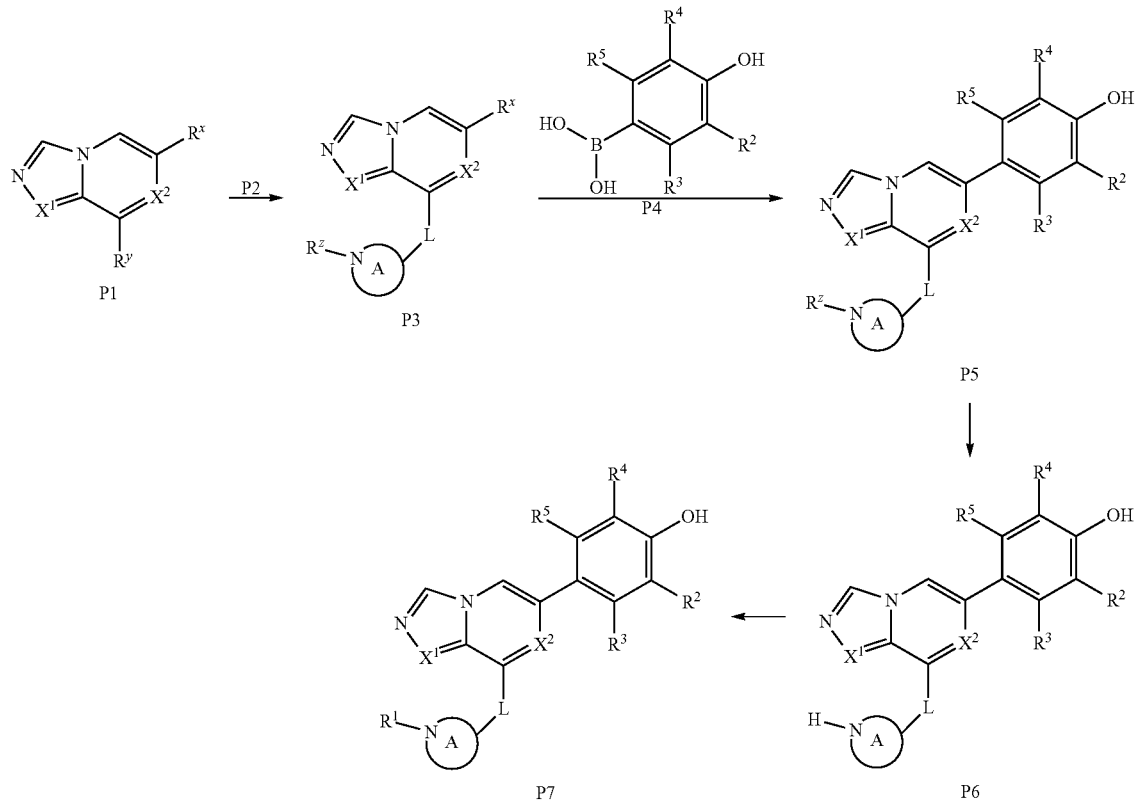

Starting material P1, where $R^x$ and $R^y$ are halogens which may be the same or different, is reacted with P2 to give P3. P2 may be:

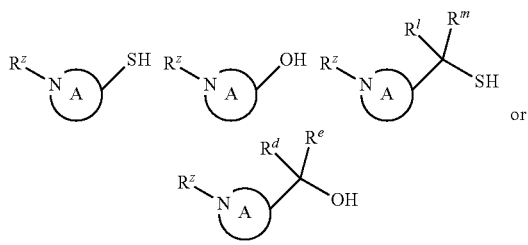

where $R^z$ is an amino-protecting group, for example Boc. In this case, P2 is deprotonated with a base such as NaH or KHMDS (potassium hexamethyldisilazide) and reacted with P1 to give P3, or P1 and P2 are combined in presence of a base, such as $Cs_2CO_3$ under heating to give P3.

Alternatively, P2 may be:

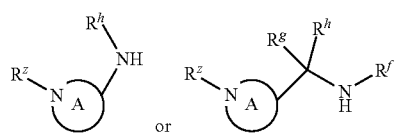

where $R^z$ is an amino-protecting group, for example Boc. In this case, P2 is reacted with P1 under Buchwald coupling conditions such as in the presence of Pd(O) and a base to give P3. Alternatively, P2 is reacted with P1 in presence of a base such as DIPEA, under heat if necessary, to give P3.

Alternatively, P2 may be:

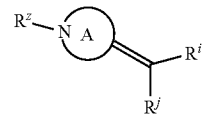

where $R^z$ is an amino-protecting group, for example Boc. In this case, P2 is reacted with P1 in presence of Pd(O), 9-BBN and a base to form P3.

P3 is coupled with boronic acid P4 through a Suzuki coupling in presence of Pd(O) and a base to give P5. P5 is deprotected to give P6 (when $R^z$ is Boc, deprotection can be conducted in the presence of a strong acid such as TFA or HCl). Finally, P6 is derivatized into an amide by amide coupling (reaction with an acid in presence of a coupling agent such as HATU or hydroxybenzotriazole (HOBT)) or reaction with an acyl chloride in presence of a base such as Hunig's base.

In this reaction scheme, the order of the reactions may be modified. For example the Suzuki coupling may be conducted before the introduction of the portion containing the A ring.

The sulfonyl linker can be obtained by oxidizing the corresponding sulfide, for example with oxone and basic alumina.

Accordingly, in a method aspect, the disclosure provides a method for preparing a compound of formula (I) or a pharmaceutically acceptable salt thereof,

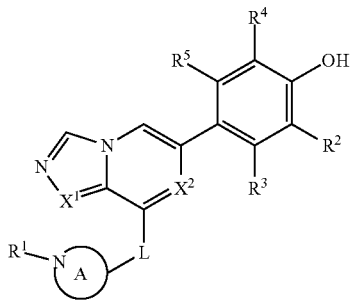

(I)

the method comprising:
reacting a compound of formula:

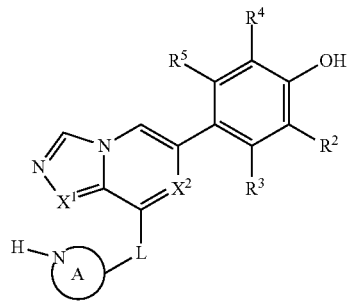

with
(i) Cl—R$^1$, or
(ii) HO—R$^1$
wherein R$^1$, R$^2$, R$^3$, R$^4$, R$^5$, X$^1$, X$^2$, L and A are as defined above, and
optionally forming a pharmaceutically-acceptable salt to provide a compound of formula (I), or a pharmaceutically acceptable salt thereof.

In separate and distinct aspects, the disclosure provides a compound of formula:

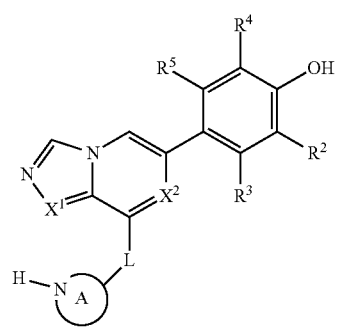

wherein the variables take any of the values described above.

Pharmaceutical Compositions

The compounds of the disclosure and pharmaceutically-acceptable salts thereof are typically used in the form of a pharmaceutical composition or formulation. Such pharmaceutical compositions may be administered to a patient by any acceptable route of administration including, but not limited to, oral, topical (including transdermal), rectal, nasal, inhaled, and parenteral modes of administration.

Accordingly, in one of its composition aspects, the invention is directed to a pharmaceutical composition comprising a pharmaceutically-acceptable carrier or excipient and a compound of formula (I), (II), (III), or (IV), or a pharmaceutically-acceptable salt thereof. Optionally, such pharmaceutical compositions may contain other therapeutic and/or formulating agents if desired. When discussing compositions and uses thereof, the "compound of the invention" or "compound of the disclosure" may also be referred to herein as the "active agent". As used herein, the term "compound(s) of the disclosure" is intended to include all compounds encompassed by formula (I), (II), (III), and (IV), and pharmaceutically-acceptable salts thereof.

The pharmaceutical compositions of the disclosure typically contain a therapeutically effective amount of a compound of the disclosure. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the active agent; including from about 5 to about 70% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the disclosure are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In some embodiments, the pharmaceutical compositions of the disclosure are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present disclosure as an active ingredient.

When intended for oral administration in a solid dosage form (i.e., as capsules, tablets, pills and the like), the pharmaceutical compositions of the disclosure will typically comprise the active agent and one or more pharmaceutically-acceptable carriers. Optionally, such solid dosage forms may comprise: fillers or extenders, such as starches, microcrystalline cellulose, lactose, dicalcium phosphate, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as crosscarmellose sodium, agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and anti-oxidants can also be present in the pharmaceutical compositions of the disclosure. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid, methacrylic acid ester copolymers, cellulose acetate trimellitate, carboxymethyl ethyl cellulose, hydroxypropyl methyl cellulose acetate succinate, and the like.

Pharmaceutical compositions of the disclosure may also be formulated to provide slow or controlled release of the active agent using, by way of example, hydroxypropyl methylcellulose in varying proportions; or other polymer matrices, liposomes and/or microspheres. In addition, the pharmaceutical compositions of the disclosure may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), oleic acid, glycerol, tetrahydrofuryl alcohol, polyethylene glycols and fatty acid esters of sorbitan, and mixtures thereof. Alternatively, certain liquid formulations can be converted, for example, by spray drying, to a powder, which is used to prepare solid dosage forms by conventional procedures.

Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of this disclosure, or a pharmaceutically acceptable salt thereof, can also be administered parenterally (e.g., by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more antioxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of the disclosure are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the disclosure will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the disclosure and a powder suitable for use in a powder inhaler. Suitable powder bases include, by way of example, lactose or starch.

The compounds of the disclosure, or a pharmaceutically acceptable salt thereof, may also be formulated for topical administration to the skin as an ointment or cream. Ointment formulations are semisolid preparations having a base of an oily or greasy material that is typically clear. Suitable oily materials for use in ointment formulations include petrolatum (petroleum jelly), beeswax, cocoa butter, shea butter, and cetyl alcohol. Ointments may optionally additionally include emollients and penetration enhancers, if desired.

Cream formulations may be prepared as emulsions comprising an oil phase and aqueous phase, typically including purified water. Components of cream formulations may include: oil bases, such as petrolatrum, mineral oils, vegetable and animal oils, and triglycerides; cream bases, such as lanolin alcohols, stearic acid, and cetostearyl alcohol; a gel base, such as polyvinyl alcohol; solvents, such as, propylene glycol and polyethylene glycol; emulsifiers, such as polysorbates, stearates, such as glyceryl stearate, octylhydroxystearate, polyoxyl stearate, PEG stearyl ethers, isopropyl palmitate, and sorbitan monostearate; stabilizers, such as polysaccharides and sodium sulfite; emollients (i.e. moisturizers), such as medium chain triglycerides, isopropyl myristate, and dimethicone; stiffening agents, such as cetyl alcohol and stearyl alcohol; antimicrobial agents, such as methylparaben, propylparaben, phenoxyethanol, sorbic acid, diazolidinyl urea, and butylated hydroxyanisole; penetration enhancers, such as N-methylpyrrolidone, propylene glycol, polyethylene glycol monolaurate, and the like; and chelating agents, such as edetate disodium.

The following non-limiting examples illustrate representative pharmaceutical compositions of the present invention.

Tablet Oral Solid Dosage Form

A compound of the disclosure or a pharmaceutically-acceptable salt thereof is dry blended with microcrystalline cellulose, polyvinyl pyrrolidone, and crosscarmellose sodium in a ratio of 4:5:1:1 and compressed into tablets to provide a unit dosage of, for example, 5 mg, 20 mg or 40 mg active agent per tablet.

Capsule Oral Solid Dosage Form

A compound of the disclosure or a pharmaceutically-acceptable salt thereof is combined with microcrystalline cellulose, polyvinyl pyrrolidone, and crosscarmellose sodium in a ratio of 4:5:1:1 by wet granulation and loaded into gelatin or hydroxypropyl methylcellulose capsules to provide a unit dosage of, for example, 5 mg, 20 mg or 40 mg active agent per capsule.

Liquid Formulation

A liquid formulation comprising a compound of the disclosure (0.1%), water (98.9%) and ascorbic acid (1.0%) is formed by adding a compound of the disclosure to a mixture of water and ascorbic acid.

Enteric Coated Oral Dosage Form

A compound of the disclosure is dissolved in an aqueous solution containing polyvinyl pyrrolidone and spray coated onto microcrystalline cellulose or sugar beads in a ratio of 1:5 w/w active agent:beads and then an approximately 5% weight gain of an enteric coating comprising an acrylic copolymer, for example a combination of acrylic copolymers available under the trade names Eudragit-L® and Eudragit-S®, or hydroxypropyl methylcellulose acetate succinate is applied. The enteric coated beads are loaded into gelatin or hydroxypropyl methylcellulose capsules to provide a unit dosage of, for example, 30 mg active agent per capsule.

Enteric Coated Oral Dosage Form

An enteric coating comprising a combination of Eudragit-L® and Eudragit-S®, or hydroxypropyl methylcellulose acetate succinate is applied to a tablet oral dosage form or a capsule oral dosage form described above.

Ointment Formulation for Topical Administration

A compound of the disclosure is combined with petrolatum, $C_{8-10}$ triglyceride, octylhydroxystearate, and N-methylpyrrolidone in a ratio to provide a composition containing 0.05% to 5% active agent by weight.

Ointment Formulation for Topical Administration

A compound of the disclosure is combined with white petrolatum, propylene glycol, mono- and di-glycerides, paraffin, butylated hydroxytoluene, and edetate calcium disodium in a ratio to provide a composition containing 0.05% to 5% active agent by weight.

Ointment Formulation for Topical Administration

A compound of the disclosure is combined with mineral oil, paraffin, propylene carbonate, white petrolatum and white wax to provide a composition containing 0.05% to 5% active agent by weight.

Cream Formulation for Topical Administration

Mineral oil is combined with a compound of the disclosure, propylene glycol, isopropyl palmitate, polysorbate 60, cetyl alcohol, sorbitan monostearate, polyoxyl 40 stearate, sorbic acid, methylparaben and propylparaben to form an oil phase, which is combined with purified water by shear blending to provide a composition containing 0.05% to 5% active agent by weight.

Cream Formulation for Topical Administration

A cream formulation comprising a compound of the disclosure, benzyl alcohol, cetyl alcohol, citric acid anhydrous, mono and di-glycerides, oleyl alcohol, propylene glycol, sodium cetostearyl sulphate, sodium hydroxide, stearyl alcohol, triglycerides, and water contains 0.05% to 5% active agent by weight.

Cream Formulation for Topical Administration

A cream formulation comprising a compound of the disclosure, cetostearyl alcohol, isopropyl myristate, propylene glycol, cetomacrogol 1000, dimethicone 360, citric acid, sodium citrate, and purified water, with imidurea, methylparaben, and propylparaben, as preservatives, contains 0.05% to 5% active agent by weight.

Utility

Inhibition of JAK3 blocks the signaling of many key pro-inflammatory cytokines. Thus the compounds of the disclosure are expected to be useful in the treatment of inflammatory diseases.

The compounds of the disclosure have been designed to be selective for JAK3 over JAK1, JAK2 and TYK2. Selectivity for JAK3 over JAK1 is anticipated to be beneficial as there is some evidence that JAK3 selectivity allows sparing of potentially beneficial cytokines such as IL-10 which has been involved in mucosal healing, IL-22 which is involved in mucus barrier protection and epithelial regeneration, and IL-6 which is involved in the proliferation of intestinal epithelial cells. Selectivity for JAK3 over JAK2 allows sparing of erythropoietin (EPO) and thrombopoietin (TPO) signaling.

Without being limited by this theory, the compounds of the disclosure possess an electrophilic portion which may form a covalent bond with the cysteine (Cys909) present in JAK3, a residue replaced by a serine in the other three JAK isoforms (Goedken et al., *J Biol Chem.*, 2015, 290, 8, 4573-89). Such covalent binding to JAK3 could be beneficial by providing an extended target engagement which may translate in better efficacy.

Additionally, certain compounds of the disclosure have minimal systemic exposure, thereby avoiding potential adverse systemic immunosuppressive effects.

Gastrointestinal Inflammatory Disease

In addition to providing potent inhibition of JAK3, some compounds of the disclosure have been designed to be poorly absorbed to minimize systemic exposure. These compounds are designed to have their effect at the site of action, for example, in the colon. Certain compounds exhibit low permeabilities with $K_p$ values less than about $5\times10^{-6}$ cm/sec, which is considered favorable to minimize systemic exposure and target the colon. Certain compounds have a $K_p$ value less than about $10\times10^{-6}$ cm/sec which may also be sufficient to minimize systemic exposure and target the colon. As described in the experimental section, compounds 12, 13, 16, and 24 exhibited a colon to plasma ratio in excess of 200. Compound 15 exhibited a colon to plasma ratio in excess of 30. Compound 30 exhibited a colon to plasma ratio in excess of 8.

It is expected that a high colon to plasma ratio will provide robust, luminally-driven anti-inflammatory activity without associated, systemically-driven, adverse effects. The compounds of the disclosure are expected to be useful for a variety of gastrointestinal inflammatory indications that include, but are not limited to, inflammatory bowel disease, ulcerative colitis (proctosigmoiditis, pancolitis, ulcerative proctitis and left-sided colitis), Crohn's disease, collagenous colitis, lymphocytic colitis, Behcet's disease, celiac disease, immune checkpoint inhibitor induced colitis, ileitis, eosinophilic esophagitis, graft versus host disease-related colitis, and infectious colitis. Ulcerative colitis (Reimund et al., *J Clin Immunology*, 1996, 16, 144-150), Crohn's disease (Woywodt et al., *Eur J Gastroenterology Hepatology*, 1999, 11, 267-276), collagenous colitis (Kumawat et al., *Mol Immunology*, 2013, 55, 355-364), lymphocytic colitis (Kumawat et al., 2013), eosinophilic esophagitis (Weinbrand-Goichberg et al., *Immunol Res*, 2013, 56, 249-260), graft versus host disease-related colitis (Coghill et al., *Blood*, 2001, 117, 3268-3276), infectious colitis (Stallmach et al., *Int J Colorectal Dis*, 2004, 19, 308-315), Behcet's disease (Zhou et al., *Autoimmun Rev*, 2012, 11, 699-704), celiac disease (de Nitto et al., *World J Gastroenterol*, 2009, 15, 4609-4614), immune checkpoint inhibitor induced colitis (e.g., CTLA-4 inhibitor-induced colitis; (Yano et al., *J Translation Med*, 2014, 12, 191), PD-1- or PD-L1-inhibitor-induced colitis), and ileitis (Yamamoto et al., *Dig Liver Dis*, 2008, 40, 253-259) are characterized by elevation of certain pro-inflammatory cytokine levels. As many pro-inflammatory cytokines signal via JAK activation, compounds described in this application are expected to be able to alleviate the inflammation and provide symptom relief.

In particular, the compounds of the disclosure are expected to be useful for the induction and maintenance of remission of ulcerative colitis, and for the treatment of Crohn's disease, immune checkpoint inhibitor induced colitis, celiac disease, and the gastrointestinal adverse effects in graft versus host disease.

In one aspect, therefore, the invention provides a method of treating a gastrointestinal inflammatory disease in a mammal (e.g., a human), the method comprising administering to the mammal a compound of the disclosure, or a pharmaceutically acceptable salt thereof, or a pharmaceutical composition comprising a pharmaceutically-acceptable carrier and a compound of the disclosure, or a pharmaceutically acceptable salt thereof. In some embodiments, the gastrointestinal inflammatory disease is ulcerative colitis. In some embodiments, the gastrointestinal inflammatory disease is celiac disease. In some embodiments, the gastrointestinal inflammatory disease is Crohn's disease. In some embodiments, the gastrointestinal inflammatory disease is immune checkpoint inhibitor induced colitis. In some embodiments, the gastrointestinal inflammatory disease is gastrointestinal adverse effects in graft versus host disease.

The invention further provides a method of treating ulcerative colitis, celiac disease, or Crohn's disease in a mammal, the method comprising administering to the mammal a compound of the disclosure, or a pharmaceutically acceptable salt thereof, or a pharmaceutical composition comprising a pharmaceutically-acceptable carrier and a compound of the disclosure, or a pharmaceutically acceptable salt thereof.

When used to treat ulcerative colitis, celiac disease, or Crohn's disease, the compounds of the disclosure, or a pharmaceutically acceptable salt thereof will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating ulcerative colitis, celiac disease, Crohn's disease and other gastrointestinal inflammatory disorders are expected to range from about 1 to about 400 mg/day of active agent, including from about 5 to about 300 mg/day and from about 20 to about 70 mg per day of active agent for an average 70 kg human.

Combination Therapy

Compounds of the disclosure, or pharmaceutically acceptable salts thereof may also be used in combination with one or more agents which act by the same mechanism or by different mechanisms to effect treatment of gastrointestinal inflammatory disorders. The different agents may be administered sequentially or simultaneously (in separate compositions or in the same composition). Useful classes of agents for combination therapy include, but are not limited to, aminosalicylates, steroids, systemic immunosuppressants, anti-TNFα antibodies, TNF alpha ligand inhibitor, TNF binding agent, anti-VLA-4 antibodies, anti-integrin $\alpha_4\beta_7$ antibodies, anti-bacterial agents, Glucocorticoid agonists, Nuclear factor kappa B inhibitors, 5-Lipoxygenase inhibitors, integrin alpha-4/beta-7 antagonist, Cyclooxygenase inhibitors, IL-23 antagonists, Leukotriene BLT receptor antagonist, IL-6 antagonists, IL-8 antagonists, integrin antagonists, nicotinic acetylcholine receptor agonists, PPAR gamma agonists, sphingosine-1-phosphate receptor-1 modulators, B-lymphocyte antigen CD20 inhibitors, calcineurin inhibitors, CD3 antagonist, cell adhesion molecule inhibitors, eosinophil peroxidase inhibitors, heparin agonists, ICAM1 gene inhibitors, IL-13 antagonists, IL-2 receptor alpha subunit inhibitors, insulin sensitizers, interferon beta ligands, interferon gamma receptor antagonists, interleukin-1 beta ligand modulators, MAdCAM inhibitors, PDE 4 inhibitors, sphingosine-1-phosphate receptor-1 agonists, TLR-9 agonists, acetylcholinesterase inhibitors, ACTH receptor agonists, activin receptor antagonists, CCR5 chemokine antagonists, CCR9 chemokine antagonists, and anti-diarrheal medicines.

Aminosalicylates that may be used in combination with the present JAK inhibitor compounds include, but are not limited to, mesalamine, osalazine and sulfasalazine. Examples of steroids include, but are not limited to, prednisone, prednisolone, hydrocortisone, budesonide, beclomethasone, and fluticasone. Systemic immunosuppressants useful for treatment of inflammatory disorders include, but are not limited to cyclosporine, azathioprine, methotrexate, 6-mercaptopurine, and tacrolimus. Further, anti-TNFα antibodies, which include, but are not limited to, infliximab, adalimumab, golimumab, and certolizumab, may be used in combination therapy. Useful compounds acting by other mechanisms include anti-VLA-4 antibodies, such as natalizumab, anti-integrin $\alpha_4\beta_7$ antibodies, such as vedolizumab, anti-bacterial agents, such as rifaximin, and anti-diarrheal medicines, such as loperamide. (Mozaffari et al. *Expert Opin. Biol. Ther.* 2014, 14, 583-600; Danese, *Gut,* 2012, 61, 918-932; Lam et al., *Immunotherapy,* 2014, 6, 963-971.)

Other compounds that may be used in combination with the present JAK inhibitor compounds include, but are not limited to opaganib, abatacept, mongersen, filgotinib, LYC-30937, BI-655130, mirikizumab, adalimumab, tacrolimus, rituximab, GSK-2982772, andecaliximab, naltrexone, risankizumab, QBECO, alicaforsen, etrolizumab, foralumab, ocrelizumab, vedolizumab, amiselimod, ozanimod, dolcanatide, catridecacog, budesonide, STNM-01, cannabidiol, telotristat etiprate, SHP-647, carotegrast methyl, peg-ilodecakin, TOP-1288, iberogast N, PF-06480605, peficitinib, beclomethasone, recombinant interferon beta-1a, infliximab, golimumab, tralokinumab, ustekinumab, certolizumab pegol, thalidomide, upadacitinib, apremilast, natalizumab, interferon beta-1a, rifaximin, RBX-2660, etrasimod, zileuton, fingolimod, cobitolimod, ropivacaine, ABX-464, PF-06700841, prednisolone, GLPG-0974, valganciclovir, ciclosporin, VB-201, tulinercept, MDGN-002, PTG-100, dexamethasone, GED-0507-34-Levo, bertilimumab, brazikumab, KHK-4083, rosiglitazone, mocravimod, sotrastaurin, KAG-308, PUR-0110, E-6007, balsalazide, basiliximab, LP-02, ASP-3291, Trichuris suis ova, K(D)PT, midismase, DNVX-078, vatelizumab, alequel, low molecular weight heparin, metenkefalin, tridecactide, HMPL-004, SB-012, olsalazine, balsalazide, propionyl-L-carnitine, Clostridium butyricum, beclomethasone and acemannan.

In another aspect, therefore, the invention provides a therapeutic combination for use in the treatment of gastrointestinal inflammatory disorders, the combination comprising a compound of the disclosure, or a pharmaceutically acceptable salt thereof, and one or more other therapeutic agents useful for treating gastrointestinal inflammatory disorders, such as the ones illustrated above. For example, the invention provides a combination comprising a compound of the disclosure, or a pharmaceutically acceptable salt thereof, and one or more agents selected from aminosalicylates, steroids, systemic immunosuppressants, anti-TNFα antibodies, anti-VLA-4 antibodies, anti-integrin $\alpha_4\beta_7$ antibodies, anti-bacterial agents, and anti-diarrheal medicines. Secondary agent(s), when included, are present in a therapeutically effective amount, i.e. in any amount that produces a therapeutically beneficial effect when co-administered with a compound of the disclosure or a pharmaceutically acceptable salt thereof.

Also provided, therefore, is a pharmaceutical composition comprising a compound of the disclosure, or a pharmaceutically acceptable salt thereof, and one or more other therapeutic agents useful for treating gastrointestinal inflammatory disorders.

Further, in a method aspect, the invention provides a method of treating gastrointestinal inflammatory disorders, the method comprising administering to the mammal a compound of the disclosure, or a pharmaceutically acceptable salt thereof, and one or more other therapeutic agents useful for treating gastrointestinal inflammatory disorders.

When used in combination therapy, the agents may be formulated in a single pharmaceutical composition, as disclosed above, or the agents may be provided in separate compositions that are administered simultaneously or at separate times, by the same or by different routes of administration. When administered separately, the agents are administered sufficiently close in time so as to provide a desired therapeutic effect. Such compositions can be packaged separately or may be packaged together as a kit. The two or more therapeutic agents in the kit may be administered by the same route of administration or by different routes of administration.

Inflammatory Skin Disease

Atopic dermatitis and other inflammatory skin diseases have been associated with elevation of proinflammatory cytokines that rely on the JAK-STAT pathway. Therefore, the compounds of the disclosure, or a pharmaceutically acceptable salt thereof, or a crystalline form thereof, may be beneficial in a number of dermal inflammatory or pruritic conditions that include, but are not limited to atopic dermatitis, alopecia areata, vitiligo, psoriasis, dermatomyositis, cutaneous T cell lymphoma (Netchiporouk et al., *Cell Cycle.* 2014; 13, 3331-3335) and subtypes (Sezary syndrome, mycosis fungoides, pagetoid reticulosis, granulomatous slack skin, lymphomatoid papulosis, pityriasis lichenoides chronica, pityriasis lichenoides et varioliformis acuta, CD30+ cutaneous T-cell lymphoma, secondary cutaneous CD30+ large cell lymphoma, non-mycosis fungoides CD30-cutaneous large T-cell lymphoma, pleomorphic T-cell lymphoma, Lennert lymphoma, subcutaneous T-cell lymphoma, angiocentric lymphoma, blastic NK-cell lymphoma), prurigo nodularis, lichen planus, primary localized cutaneous amyloidosis, bullous pemphigoid, skin manifestations of graft versus host disease, pemphigoid, discoid lupus, granuloma annulare, lichen simplex chronicus, vulvar/scrotal/perianal pruritus, lichen sclerosus, post herpetic neuralgia itch, lichen planopilaris, and foliculitis decalvans. In particular, atopic dermatitis (Bao et al., *JAK-STAT,* 2013, 2, e24137), alopecia areata (Xing et al., *Nat Med.* 2014, 20, 1043-1049), vitiligo (Craiglow et al, *JAMA Dermatol.* 2015, 151, 1110-1112), prurigo nodularis (Sonkoly et al., *J Allergy Clin Immunol.* 2006, 117, 411-417), lichen planus (Welz-Kubiak et al., *J Immunol Res.* 2015, ID:854747), primary localized cutaneous amyloidosis (Tanaka et al., *Br J Dermatol.* 2009, 161, 1217-1224), bullous pemphigoid (Feliciani et al., *Int J Immunopathol Pharmacol.* 1999, 12, 55-61), and dermal manifestations of graft versus host disease (Okiyama et al., *J Invest Dermatol.* 2014, 134, 992-1000) are characterized by elevation of certain cytokines that signal via JAK activation. Accordingly, compounds of the disclosure, or a pharmaceutically acceptable salt thereof, have the potential to alleviate associated dermal inflammation or pruritus driven by these cytokines. In particular, compounds of the disclosure, or a pharmaceutically acceptable salt thereof, are expected to be useful for the treatment of atopic dermatitis and other inflammatory skin diseases.

In one aspect, therefore, the invention provides a method of treating an inflammatory skin disease in a mammal (e.g., a human), the method comprising applying a pharmaceutical composition comprising a compound of the disclosure, or a pharmaceutically acceptable salt thereof, and a pharmaceutical carrier to the skin of the mammal. In one aspect, the inflammatory skin disease is atopic dermatitis.

Compounds of the disclosure, or a pharmaceutically acceptable salt thereof, may also be used in combination with one or more compound useful to treat inflammatory skin diseases. In some embodiments, the one or more compound is a steroid, Histamine H1 receptor antagonist, calcineurin inhibitor, IL-13 antagonist, PDE 4 inhibitor, G-protein coupled receptor-44 antagonist, IL-4 antagonist, 5-HT 1a receptor antagonist, 5-HT 2b receptor antagonist, Alpha 2 adrenoceptor agonist, cannabinoid CB1 receptor antagonist, CCR3 chemokine, antagonist, collagenase inhibitor, cytosolic phospholipase A2 inhibitor, eotaxin ligand inhibitor, GATA 3 transcription factor inhibitor, Histamine H4 receptor antagonist, IL-10 antagonist, IL-12 antagonist, IL-17 antagonist, IL-2 antagonist, IL-23 antagonist, IL-4 receptor modulator, IL-5 antagonist, immunoglobulin E antagonist, immunoglobulin E modulator, interferon gamma receptor antagonist, Interleukin 33 ligand inhibitor, Interleukin-31 receptor antagonist, Leukotriene antagonist, Liver X receptor agonist, Liver X receptor beta agonist, nuclear factor kappa B inhibitor, OX-40 receptor antagonist, PGD2 antagonist, phospholipase A2 inhibitor, SH2 domain inositol phosphatase 1 stimulator, thymic stromal lymphoprotein ligand inhibitor, TLR modulator, TNF alpha ligand modulator, or vanilloid VR1 antagonist. In some embodiments, the one or more compound is a gram positive antibiotic, such as mupirocin or fusidic acid. In some embodiments, the one or more compound is tranilast, tacrolimus, epinastine, SB-011, AM-1030, ZPL-521, MM-36, FB-825, PG-102, viromed, GBR-830, AVX-001, AMG-0101, E-6005, DMT-210, AX-1602, bertilimumab, rosiptor acetate, Q-301, ANB-020, VTP-38543, ZPL-389, lebrikizumab, tezepelumab, fexofenadine, pimecrolimus, bepotastine, crisaborole, tralokinumab, fevipiprant, doxycycline, desloratadine, ALX-101, nemolizumab, asivatrep, ciclosporin, mepolizumab, dupilumab, secukinumab, timapiprant, or ustekinumab.

In one aspect, therefore, the invention provides a method of treating an inflammatory skin disease in a mammal, the method comprising applying a compound of the disclosure, or a pharmaceutically acceptable salt thereof, and a gram positive antibiotic to the skin of the mammal. In another aspect, the invention provides a pharmaceutical composition comprising a compound of the disclosure, or a pharmaceutically acceptable salt thereof, a gram positive antibiotic, and a pharmaceutically-acceptable carrier.

Respiratory Diseases

Cytokines which signal through the JAK-STAT pathway, in particular IL-2, IL-3, IL-4, IL-5, IL-6, IL-9, IL-11, IL-13, IL-23, IL-31, IL-27, thymic stromal lymphopoietin (TSLP), interferon-γ (IFNγ) and granulocyte-macrophage colony-stimulating factor (GM-CSF) have also been implicated in asthma inflammation and in other inflammatory respiratory diseases. As described above, the compounds of the disclosure have been shown to be potent inhibitors of JAK3 and have also demonstrated potent inhibition of IL-2 pro-inflammatory cytokines in cellular assays.

The anti-inflammatory activity of JAK inhibitors has been robustly demonstrated in preclinical models of asthma (Malaviya et al., *Int Immunopharmacol*, 2010, 10, 829-836; Matsunaga et al., *Biochem and Biophys Res Commun*, 2011, 404, 261-267; Kudlacz et al., *Eur J Pharmacol*, 2008, 582, 154-161.) Accordingly, the compounds of the disclosure, or a pharmaceutically acceptable salt thereof, are expected to be useful for the treatment of inflammatory respiratory disorders such as asthma. Inflammation and fibrosis of the lung is characteristic of other respiratory diseases in addition to asthma such as chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, and bronchiolitis obliterans. The compounds of the disclosure, or a pharmaceutically acceptable salt thereof, therefore, may be useful for the treatment of chronic obstructive pulmonary disease, cystic fibrosis, pneumonitis, interstitial lung diseases (including idiopathic pulmonary fibrosis), acute lung injury, acute respiratory distress syndrome, bronchitis, emphysema, bronchiolitis obliterans, bronchiolitis obliterans organizing pneumonia (also termed COS), primary Graft Dysfunction (PGD), organizing pneumonia (OP), acute rejection (AR), lymphocytic bronchiolitis (LB), chronic Lung Allograft Dysfunction (CLAD), restrictive CLAD (rCLAD or RAS), neutrophilic allograft dysfunction, and sarcoidosis.

In one aspect, therefore, the disclosure provides a method of treating a respiratory disease in a mammal (e.g., a human), the method comprising administering to the mammal a compound of the disclosure, or a pharmaceutically-acceptable salt thereof.

In one aspect, the respiratory disease is asthma, chronic obstructive pulmonary disease, cystic fibrosis, pneumonitis, chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, bronchiolitis obliterans, bronchiolitis obliterans organizing pneumonia (also termed COS), primary Graft Dysfunction (PGD), organizing pneumonia (OP), acute rejection (AR), lymphocytic bronchiolitis (LB), chronic Lung Allograft Dysfunction (CLAD), restrictive CLAD (rCLAD or RAS), neutrophilic allograft dysfunction, allergic rhinitis or sarcoidosis. In another aspect, the respiratory disease is asthma or chronic obstructive pulmonary disease.

In a further aspect, the respiratory disease is a lung infection, a helminthic infection, pulmonary arterial hypertension, sarcoidosis, lymphangioleiomyomatosis, bronchiectasis, or an infiltrative pulmonary disease. In yet another aspect, the respiratory disease is drug-induced pneumonitis, fungal induced pneumonitis, allergic bronchopulmonary aspergillosis, hypersensitivity pneumonitis, eosinophilic granulomatosis with polyangiitis, idiopathic acute eosinophilic pneumonia, idiopathic chronic eosinophilic pneumonia, hypereosinophilic syndrome, Löffler syndrome, bronchiolitis obliterans organizing pneumonia, or immune-checkpoint-inhibitor induced pneumonitis.

The disclosure further provides a method of treating a respiratory disease, the method comprising administering to the mammal a pharmaceutical composition comprising a compound of the disclosure, or a pharmaceutically-acceptable salt thereof, and a pharmaceutically-acceptable carrier.

Compounds of the disclosure, or pharmaceutically acceptable salts thereof, may also be used in combination with one or more compound useful to respiratory diseases.

Ocular Diseases

Many ocular diseases have been shown to be associated with elevations of proinflammatory cytokines that rely on the JAK-STAT pathway.

The compounds of the disclosure, or a pharmaceutically acceptable salt thereof, therefore, may be useful for the treatment of a number of ocular diseases that include, but are not limited to, uveitis, diabetic retinopathy, diabetic macular edema, dry eye disease, age-related macular degeneration, retinal vein occlusion (RVO) and atopic keratoconjunctivitis.

In particular, uveitis (Horai and Caspi, *J Interferon Cytokine Res*, 2011, 31, 733-744), diabetic retinopathy (Abcouwer, *J Clin Cell Immunol*, 2013, *Suppl* 1, 1-12), diabetic macular edema (Sohn et al., *American Journal of Optha-* mology, 2011, 152, 686-694), dry eye disease (Stevenson et al, *Arch Ophthalmol,* 2012, 130, 90-100), retinal vein occlusion (Shchuko et al, *Indian Journal of Ophthalmology,* 2015, 63(12), 905-911) and age-related macular degeneration (Knickelbein et al, *Int Ophthalmol Clin,* 2015, 55(3), 63-78) are characterized by elevation of certain pro-inflammatory cytokines that signal via the JAK-STAT pathway. Accordingly, compounds of the disclosure, or a pharmaceutically acceptable salt thereof, may be able to alleviate the associated ocular inflammation and reverse disease progression or provide symptom relief.

In one aspect, therefore, the disclosure provides a method of treating an ocular disease in a mammal, the method comprising administering a pharmaceutical composition comprising a compound of the disclosure, or a pharmaceutically-acceptable salt thereof, and a pharmaceutical carrier to the eye of the mammal. In one aspect, the ocular disease is uveitis, diabetic retinopathy, diabetic macular edema, dry eye disease, age-related macular degeneration, retinal vein occlusion or atopic keratoconjunctivitis. In one aspect, the method comprises administering the compound of the disclosure, or a pharmaceutically acceptable salt thereof, by intravitreal injection.

Compounds of the disclosure, or a pharmaceutically acceptable salt thereof, may also be used in combination with one or more compound useful to ocular diseases.

Other Diseases

The compounds of the disclosure, or a pharmaceutically acceptable salt thereof, may also be useful to treat other diseases such as other inflammatory diseases, autoimmune diseases or cancers.

The compounds of the disclosure, or a pharmaceutically acceptable salt thereof, may be useful to treat one or more of arthritis, rheumatoid arthritis, juvenile rheumatoid arthritis, transplant rejection, xerophthalmia, psoriatic arthritis, diabetes, insulin dependent diabetes, motor neurone disease, myelodysplastic syndrome, pain, sarcopenia, cachexia, septic shock, systemic lupus erythematosus, leukemia, chronic lymphocytic leukemia, chronic myelocytic leukemia, acute lymphoblastic leukemia, acute myelogenous leukemia, ankylosing spondylitis, myelofibrosis, B-cell lymphoma, hepatocellular carcinoma, Hodgkins disease, breast cancer, Multiple myeloma, melanoma, non-Hodgkin lymphoma, non-small-cell lung cancer, ovarian clear cell carcinoma, ovary tumor, pancreas tumor, polycythemia vera, Sjoegrens syndrome, soft tissue sarcoma, sarcoma, splenomegaly, T-cell lymphoma, and thalassemia major.

Compounds of the disclosure have been demonstrated to be potent inhibitors of the JAK3 enzyme and to be selective for JAK3 over JAK1, JAK2 and TYK2 in enzyme binding assays and to have potent functional activity for JAK3 in a cellular assay as described in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
Calcd=calculated
Boc=tert-Butyloxycarbonyl
d=day(s)
DIPEA=N,N-diisopropylethylamine
DMF=N,N-dimethylformamide
DMSO=dimethyl sulfoxide
EtOAc=ethyl acetate
EtOH=ethyl alcohol
h=hour(s)
HATU=N,N,N',N'-tetramethyl-O-(7-azabenzotriazol-1-yl)uronium hexafluorophosphate
IPA=isopropyl alcohol
MeOH=methanol
min=minute(s)
RT or rt=room temperature
SiG=Silica gel
TEA=triethylamine
THF=tetrahydrofuran
THP=tetrahydropyran
TFA=trifluoroacetic acid Reagents and solvents were purchased from commercial suppliers (Aldrich, Fluka, Sigma, etc.), and used without further purification. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by column chromatography or by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as $CD_3OD$, $CDCl_3$, or $d_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or a Waters (Milford, Ma.) 3100 instrument, coupled to autopurification systems.

Unless otherwise indicated the following conditions were used for preparative HPLC purifications.

Column: C18, 5 µm 21.2×150 mm or C18, 5 µm 21×250 mm or C14, 5 µm 21×150 mm
Column temperature: Room Temperature
Flow rate: 20.0 mL/min
Mobile Phases: A=Water+0.05% TFA
B=ACN+0.05% TFA,
Injection volume: (100-1500 µL)
Detector wavelength: 214 nm Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 uL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

Analytic HPLC Conditions
Method A
Column: LUNA C18 (2), 150×4.60 mm, 3 µm
Column temperature: 37° C.
Flow rate: 1.0 mL/min
Injection volume: 5 µL
Sample preparation: Dissolve in 1:1 ACN:water Mobile Phases: A=Water:ACN:TFA (98:2:0.05) B=Water:ACN:TFA (2:98:0.05)

Detector wavelength: 250 nm

Gradient: 32 min total (time (min)/% B): 0/2, 10/20, 24/90, 29/90, 30/2, 32/2

Method B

Column: LUNA C18 (2), 150×4.60 mm, 3 µm

Column temperature: 37° C.

Flow rate: 1.0 mL/min

Injection volume: 10 µL

Sample preparation: Dissolve in 1:1 ACN:water

Mobile Phases: A=Water:ACN:TFA (98:2:0.05) B=Water:ACN:TFA (10:90:0.05)

Detector wavelength: 254 nm

Gradient: 35 min total (time (min)/% B): 0/2, 20/25, 23/90, 26/90, 27/2, 35/2

Preparation 1: tert-butyl (S)-3-((6-bromoimidazo[1,5-a]pyridin-8-yl)oxy)pyrrolidine-1-carboxylate

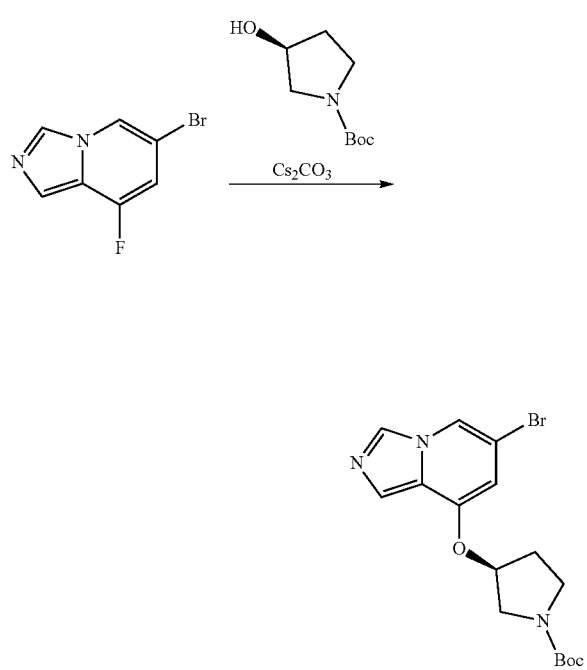

To a stirring solution of 6-bromo-8-fluoroimidazo[1,5-a]pyridine (500 mg, 2.32 mmol) in DMSO (10 mL) was added tert-butyl (S)-3-hydroxypyrrolidine-1-carboxylate (521 mg, 2.79 mmol) and $Cs_2CO_3$ (1.51 g, 4.65 mmol) at room temperature. The reaction mixture was allowed to stir at 120° C. for 4 h. The reaction was diluted with water and extracted with EtOAc. The organic layer was washed with brine, dried over anhydrous $Na_2SO_4$, filtered, and concentrated under reduced pressure. The crude material was purified by silica gel column chromatography using a 30-35% EtOAc:hexanes gradient and afforded the desired product (550 mg, 1.44 mmol). (m/z): $[M+H]^+$ calculated for $C_{16}H_{20}BrN_3O_3$ 383.0 found 383.0.

Preparation 2: tert-butyl (S)-3-((6-(4-hydroxyphenyl)imidazo[1,5-a]pyridin-8-yl)oxy)pyrrolidine-1-carboxylate

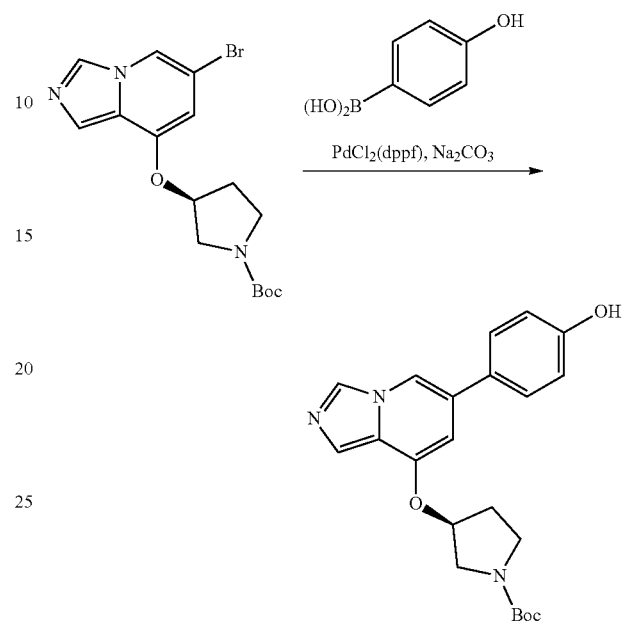

To a stirring solution of tert-butyl (S)-3-((6-bromoimidazo[1,5-a]pyridin-8-yl)oxy)pyrrolidine-1-carboxylate (550 mg, 1.43 mmol) in dioxane (12 mL) and water (3 mL) was added (4-hydroxyphenyl)boronic acid (238 mg, 1.72 mmol) and $Na_2CO_3$ (305 mg, 2.86 mmol). The reaction was purged with argon for 15 min and then $Pd(dppf)Cl_2 \cdot DCM$ (117 mg, 0.144 mmol) was added and the reaction was sealed, heated to 120° C., and stirred for 2 h. The reaction was then cooled to room temperature and the organic layer was dried over $Na_2SO_4$ (238 mg, 1.73 mmol) and $Na_2CO_3$ (305 mg, 2.88 mmol). The mixture was then filtered through a celite pad and the filtrate was concentrated under reduced pressure to obtain the crude material. Purification of the crude material by silica gel column chromatography using a 30-35% EtOAc:hexanes gradient afforded the desired product (453 mg, 1.15 mmol). (m/z): $[M+H]^+$ calculated for $C_{22}H_{25}N_3O_4$ 396.19 found 396.29.

Preparation 3: (S)-4-(8-(pyrrolidin-3-yloxy)imidazo[1,5-a]pyridin-6-yl)phenol

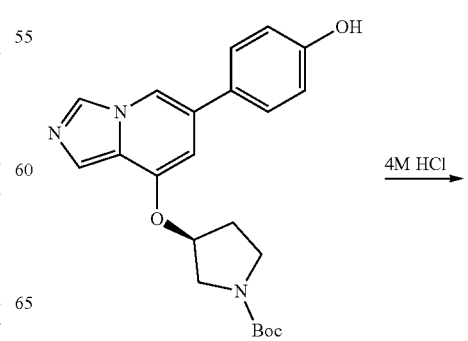

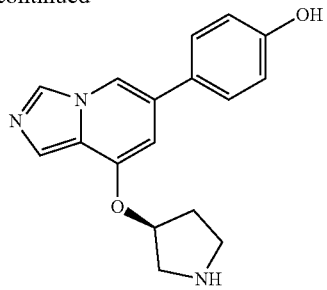

To a stirring solution of tert-butyl (S)-3-(((6-(4-hydroxyphenyl)imidazo[1,5-a]pyridin-8-yl)oxy)pyrrolidine-1-carboxylate (420 mg, 1.088 mmol) in dioxane (15 mL) was added 4M HCl in dioxane (15 mL) at 0° C. under a nitrogen atmosphere. The reaction mixture was stirred for 2 h at room temperature. The reaction was then concentrated under reduced pressure and dried under high-vacuum to obtain the crude material. The crude was triturated with diethyl ether to obtain the product as an HCl salt (350 mg, 1.06 mmol). (m/z): [M+H]$^+$ calculated for $C_{17}H_{17}N_3O_2$ 296.14 found 296.11.

Example 1: (S)-1-(3-(((6-(4-hydroxyphenyl)imidazo[1,5-a]pyridin-8-yl)oxy)pyrrolidin-1-yl)prop-2-en-1-one

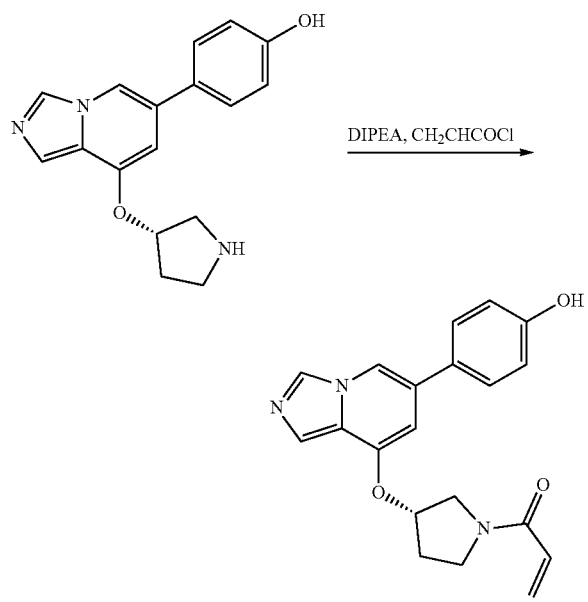

To a stirring solution of (S)-4-(8-(pyrrolidin-3-yloxy)imidazo[1,5-a]pyridin-6-yl)phenol (32 mg, 0.095 mmol) in DMF (475 μL) was added DIPEA (83 μl, 0.48 mmol) and the reaction was cooled to 0° C. After 5 minutes of stirring, acryloyl chloride (7.7 μL, 0.095 mmol) was added and the reaction was stirred at 0° C. for 10 minutes. LCMS analysis indicated formation of the desired product and the reaction was then concentrated in vacuo. The crude residue was dissolved in ~1:1 AcOH:H$_2$O and purified by reverse phase HPLC using a 5-45% MeCN:H$_2$O (with 0.1% TFA) gradient on a Phenomenex 21.2×250 mm Luna Axia C18 column to yield the desired product as a TFA salt (3.2 mg, 0.007 mmol). (m/z): [M+H]$^+$ calculated for $C_{20}H_{19}N_3O_3$ 350.1 found 350.1.

Preparation 4: tert-butyl 4-(((6-bromoimidazo[1,5-a]pyridin-8-yl)oxy)methyl)piperidine-1-carboxylate

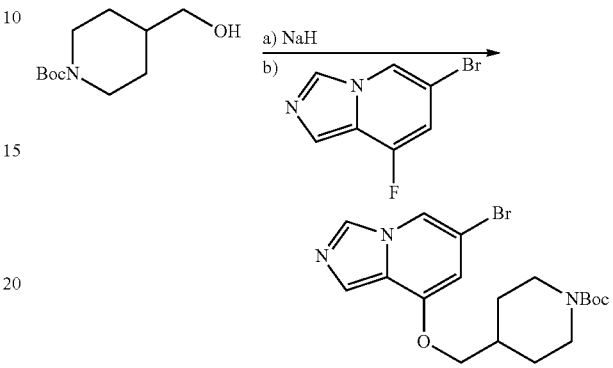

To a stirring solution of tert-butyl 4-(hydroxymethyl)piperidine-1-carboxylate (451 mg, 2.093 mmol) in DMF (3.5 mL) at 0° C. was added sodium hydride (60% dispersion in mineral oil) (89 mg, 2.2 mmol). The reaction was warmed to room temperature and stirred for 30 minutes. 6-bromo-8-fluoroimidazo[1,5-a]pyridine (300 mg, 1.40 mmol) in DMF (3.5 mL) was added to the reaction at 0° C. The reaction was stirred overnight at room temperature and then quenched with 10 mL H$_2$O and extracted with 3×10 mL EtOAc. The organic extracts were combined and washed with ~50 mL 1:1 H$_2$O:brine, dried over Na$_2$SO$_4$, filtered, and concentrated onto celite. The crude material was purified by silica gel column chromatography using a 0-80% EtOAc:Hex gradient to yield the desired product (290 mg, 1.40 mmol). (m/z): [M+H]$^+$ calculated for $C_{18}H_{24}BrN_3O_3$ 411.1 found 411.0.

Preparation 5: tert-butyl 4-(((6-(4-hydroxyphenyl)imidazo[1,5-a]pyridin-8-yl)oxy)methyl) piperidine-1-carboxylate

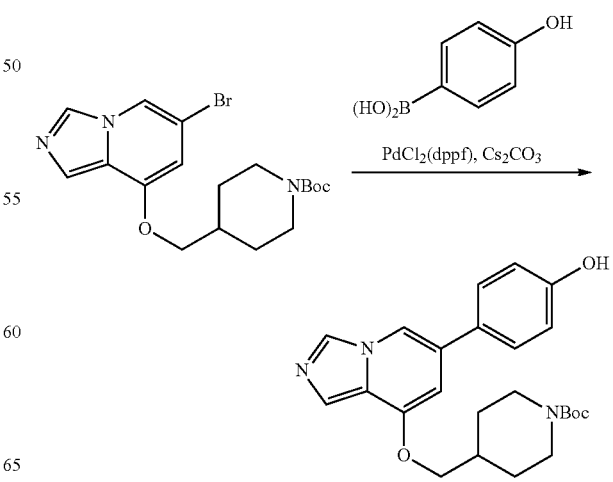

To a stirring solution of tert-butyl 4-(((6-bromoimidazo[1,5-a]pyridin-8-yl)oxy)methyl)piperidine-1-carboxylate (290 mg, 0.707 mmol) in dioxane (2.8 mL) was added 4-hydroxyphenylboronic acid (136 mg, 0.989 mmol), and a solution of cesium carbonate (691 mg, 2.12 mmol) in water (0.7 mL). The reaction was sealed, heated to 110° C. and stirred overnight. The reaction was cooled to room temperature, concentrated onto celite, and purified by silica gel column chromatography using a 10-80% EtOAc:Hex gradient to afford the desired product (45 mg, 0.106 mmol). (m/z): [M+H]$^+$ calculated for $C_{24}H_{29}N_3O_4$ 424.2 found 424.1.

Preparation 6: 4-(8-(piperidin-4-ylmethoxy)imidazo[1,5-a]pyridin-6-yl)phenol

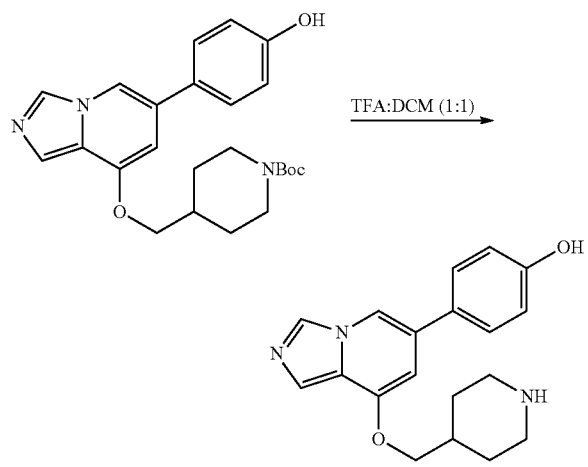

To a solution of tert-butyl 4-(((6-(4-hydroxyphenyl)imidazo[1,5-a]pyridin-8-yl)oxy)methyl)piperidine-1-carboxylate in DCM (500 µL) was added TFA (500 µL) and the reaction was stirred for 2 hours before being concentrated in vacuo to afford the crude product (47 mg, 0.106 mmol). (m/z): [M+H]$^+$ calculated for $C_{19}H_{21}N_3O_2$ 324.2 found 324.

Example 2: 1-(4-(((6-(4-hydroxyphenyl)imidazo[1,5-a]pyridin-8-yl)oxy)methyl) piperidin-1-yl)prop-2-en-1-one

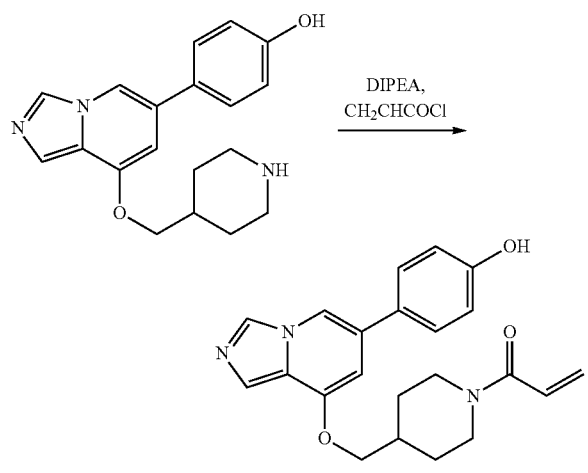

To a stirring solution of 4-(8-(piperidin-4-ylmethoxy)imidazo[1,5-a]pyridin-6-yl)phenol in DMF (274 µl) was added DIPEA (57.5 µl, 0.329 mmol) and then acryloyl chloride (4.01 µl, 0.049 mmol). The reaction was stirred at room temperature for 5 minutes and then concentrated in vacuo. The crude material was redissolved in ~1:1 AcOH:H$_2$O and purified by reverse phase HPLC using a 19-50% MeCN:H$_2$O (0.1% TFA) gradient on a Phenomenex 21.2× 250 mm Luna Axia C18 column to afford the desired product as a TFA salt (8.6 mg, 0.017 mmol). (m/z): [M+H]$^+$ calculated for $C_{22}H_{22}N_3O_3$ 378.2 found 378.1.

Preparation 7: 4-(8-fluoroimidazo[1,5-a]pyridin-6-yl)phenol

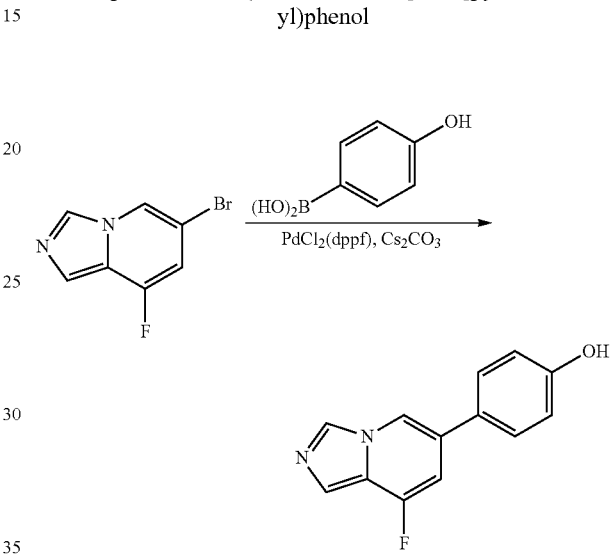

To a stirring solution of 6-bromo-8-fluoroimidazo[1,5-a]pyridine (900 mg, 4.19 mmol) in dioxane (13.4 mL) was added 4-hydroxyphenylboronic acid (866 mg, 6.28 mmol), a solution of cesium carbonate (4091 mg, 12.56 mmol) in H$_2$O (3.35 mL), and dichloro[1,1'-bis(diphenylphosphino)ferrocene]palladium (513 mg, 0.628 mmol). The reaction was sealed, heated to 110° C. and stirred overnight. The reaction was concentrated directly onto celite and purified by silica gel column chromatography using a 0-95% EtOAc:Hex gradient to afford the desired product (812 mg, 3.56 mmol). (m/z): [M+H]$^+$ calculated for $C_{13}H_9FN_2O$, 229.1 found 229.

Preparation 8: tert-butyl 5-((6-(4-hydroxyphenyl)imidazo[1,5-a]pyridin-8-yl)oxy)-2-azaspiro[3.3]heptane-2-carboxylate

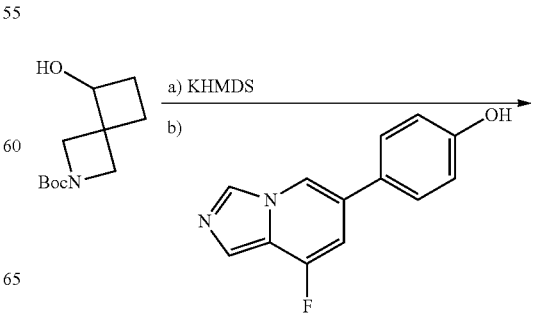

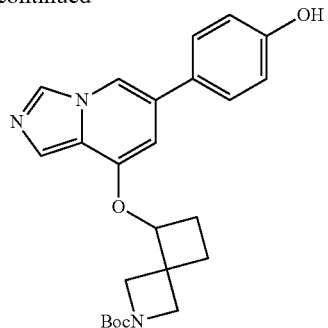

To a solution of tert-butyl 5-hydroxy-2-azaspiro[3.3]heptane-2-carboxylate in DMF (3.3 mL) at 0° C. was added potassium hexamethyldisilazide (1.0 M in THF) (1.78 mL, 1.775 mmol) and the reaction was warmed to room temperature and stirred for 20 minutes. A solution of 4-(8-fluoroimidazo[1,5-a]pyridin-6-yl)phenol (150 mg, 0.657 mmol) in DMF (3.3 mL) was then added to the potassium alkoxide solution. The resulting reaction was stirred at room temperature for 3 hours, then diluted with 10 mL H$_2$O and extracted with 3×5 mL EtOAc. The organic fractions were combined and dried over Na$_2$SO$_4$, filtered, and concentrated onto celite. Purification by silica gel column chromatography using a 10-100% EtOAc:Hex gradient yielded the desired product (166 mg, 0.394 mmol). (m/z): [M+H]$^+$ calculated for C$_{37}$H$_{36}$FN$_5$O$_5$ 422.2 found 422.

Preparation 9: 4-(8-((2-azaspiro[3.3]heptan-5-yl)oxy)imidazo[1,5-a]pyridin-6-yl)phenol

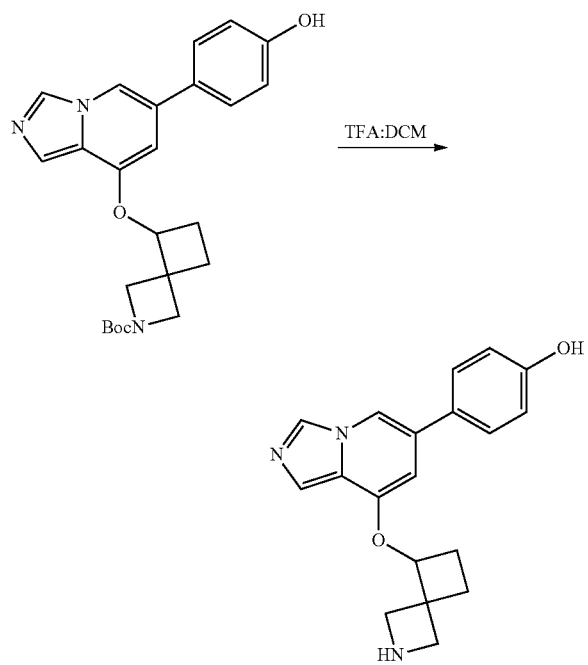

To a stirring solution of tert-butyl 5-((6-(4-hydroxyphenyl)imidazo[1,5-a]pyridin-8-yl)oxy)-2-azaspiro[3.3]heptane-2-carboxylate (166 mg, 0.394 mmol) in DCM (500 µL) was added TFA (500 µL). The reaction was stirred for 2 hours and then concentrated in vacuo to afford the crude product as a TFA salt. The crude product was used without any further purification and 100% yield was assumed (127 mg, 0.394 mmol). (m/z): [M+H]$^+$ calculated for C$_{19}$H$_{19}$N$_3$O$_3$ 322.2 found 322.

Example 3: 1-(5-((6-(4-hydroxyphenyl)imidazo[1,5-a]pyridin-8-yl)oxy)-2-azaspiro[3.3]heptan-2-yl)prop-2-en-1-one

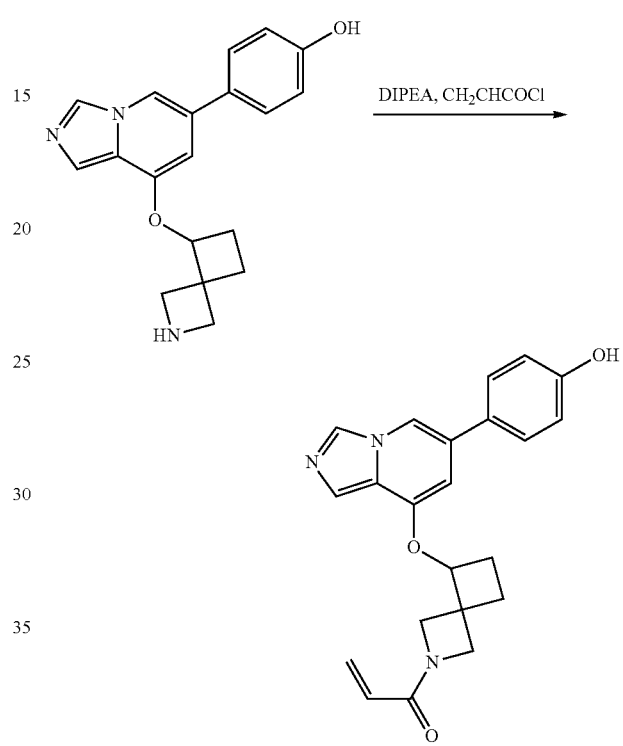

To a solution of 4-(8-((2-azaspiro[3.3]heptan-5-yl)oxy)imidazo[1,5-a]pyri din-6-yl)phenol (127 mg, 0.395 mmol) in DMF (1.98 mL) was added DIPEA (414 µL, 2.37 mmol) and then acryloyl chloride (24.1 µL, 0.296 mmol). The reaction was stirred for 5 minutes and was then concentrated in vacuo. The crude residue was dissolved in ~1:1 AcOH:H$_2$O and purified by reverse phase HPLC using a 15-50% MeCN:H$_2$O (with 0.1% TFA) gradient on a Phenomenex 21.2×250 mm Luna Axia C18 column to afford the desired product (8.6 mg, 0.023 mmol). (m/z): [M+H]$^+$ calculated for C$_{19}$H$_{19}$N$_3$O$_2$ 376.2 found 376.2.

Preparation 10: tert-butyl 4-((6-bromoimidazo[1,5-a]pyridin-8-yl)amino)piperidine-1-carboxylate

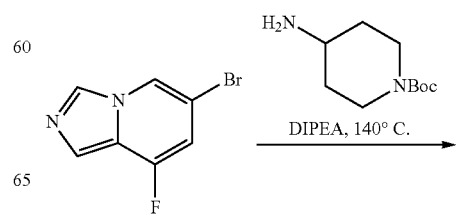

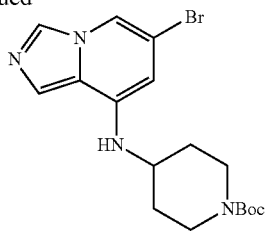

To a stirring solution of 6-bromo-8-fluoroimidazo[1,5-a]pyridine (560 mg, 2.80 mmol) in DMSO (10 ml) was added DIPEA (0.73 mL, 4.20 mmol). Tert-butyl 4-aminopiperidine-1-carboxylate (500 mg, 1.40 mmol) was added and the reaction was heated to 140° C. and stirred for 16 h. The reaction was then cooled and diluted with water and extracted EtOAc. The organic fraction was washed with brine, dried over $Na_2SO_4$, filtered, and then concentrated under reduced pressure to obtain the crude product. Purification of the crude material by silica gel column chromatography using a 10% MeOH:DCM solvent system afforded the desired product (160 mg, 0.40 mmol). (m/z): [M+H]$^+$ calculated for $C_{17}H_{23}BrN_4O_2$ 396.1 found 396.0.

Preparation 11: tert-butyl 4-((6-(4-hydroxyphenyl)imidazo[1,5-a]pyridin-8-yl)amino)piperidine-1-carboxylate

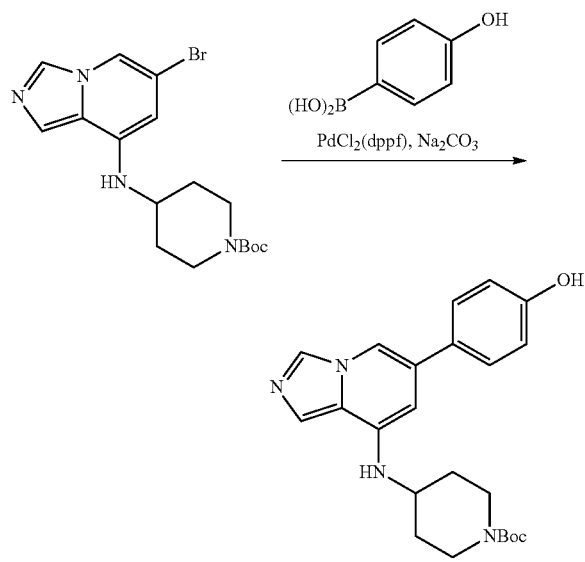

To a pressure tube was added tert-butyl 4-((6-bromoimidazo[1,5-a]pyridin-8-yl)amino)piperidine-1-carboxylate (160 mg, 0.406 mmol) in dioxane (12 ml) and $H_2O$ (3 ml) followed by (4-hydroxyphenyl)boronic acid (71 mg, 0.487 mmol) and $Na_2CO_3$ (91 mg, 0.812 mmol). The reaction mixture was purged with argon for 10 minutes and then $PdCl_2$(dppf) (35 mg, 0.041 mmol) was added. The reaction was heated to 120° C. and stirred for 4 h. The reaction was cooled and diluted with water and extracted with ethyl acetate, and the organic phase was then washed with water and brine solution. The organic layer was dried over $Na_2SO_4$, filtered, and then concentrated under reduced pressure to obtain the crude product. The crude product was purified by silica gel column chromatography with 100% EtOAc to afford the desired product.

Preparation 12: 4-(8-(piperidin-4-ylamino)imidazo[1,5-a]pyridin-6-yl)phenol

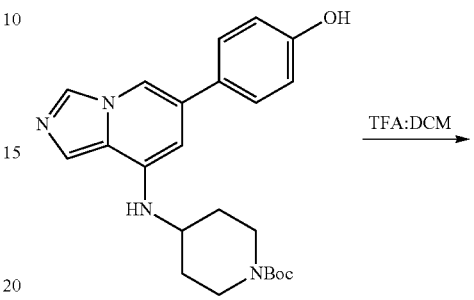

To a stirring solution of tert-butyl 4-((6-(4-hydroxyphenyl)imidazo[1,5-a]pyridin-8-yl)amino)piperidine-1-carboxylate (100 mg, 0.245 mmol) in DCM (10 mL) was added TFA (1 mL) at 0° C. The resulting reaction mixture was warmed to room temperature at stirred for 1 h. The reaction was then concentrated under reduced pressure to obtain the crude product. The crude product was triturated with diethyl ether to obtain the desired product as a beige solid. (m/z): [M+H]$^+$ calculated for $C_{18}H_{20}N_4O$, 309.1 found 309.1.

Example 4: 1-(4-((6-(4-hydroxyphenyl)imidazo[1,5-a]pyridin-8-yl)amino)piperidin-1-yl)prop-2-en-1-one

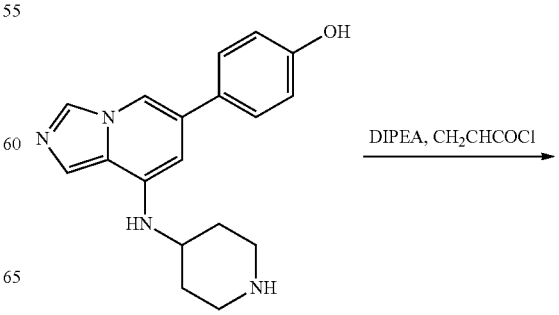

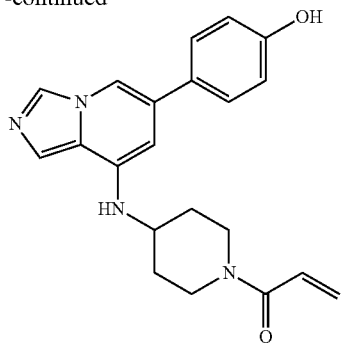

To a stirring solution of 4-(8-(piperidin-4-ylamino)imidazo[1,5-a]pyridin-6-yl)phenol (30 mg, 0.071 mmol) in DMF (355 μL) was added DIPEA (75 μl, 0.426 mmol) and then acryloyl chloride (5.2 μl, 0.064 mmol). The reactions were stirred for 5 minutes and then concentrated in vacuo. The crude residue was dissolved in ~1:1 AcOH:H$_2$O and purified by reverse phase HPLC using a 10-40% MeCN:H$_2$O (with 0.1% TFA) gradient on a MAC-MOD 21.2×150 mm ACE C18-PFP 5 μm column to afford the desired product as a TFA salt (2.3 mg, 0.006 mmol). (m/z): [M+H]$^+$ calculated for C$_{21}$H$_{22}$N$_4$O, 363.2 found 363.2.

Preparation 13:
5-chloro-3-fluoro-2-hydrazinylpyridine

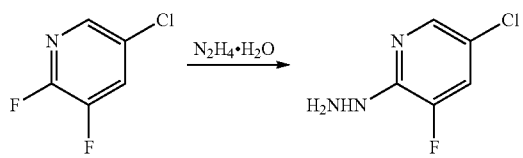

To a stirring solution of 5-chloro-2,3-difluoropyridine (2.0 g, 13.42 mmol) in ethanol (30 mL) was added N$_2$H$_4$·H$_2$O (3.35 mL, 67.11 mmol) and the reaction was brought to reflux and stirred for 16 h. The reaction was then cooled and concentrated half the original volume, and then cooled in an ice bath to induce precipitation. The precipitate was filtered and washed with a minimal amount of EtOH and water, then dried under vacuum to obtain the desired product as a white powder (1.9 g, 11.76 mmol). (m/z): [M+H]$^+$ calculated for C$_5$H$_5$ClFN$_3$ 163.0 found 163.9.

Preparation 14: 6-chloro-8-fluoro-[1,2,4]triazolo[4,3-a]pyridine

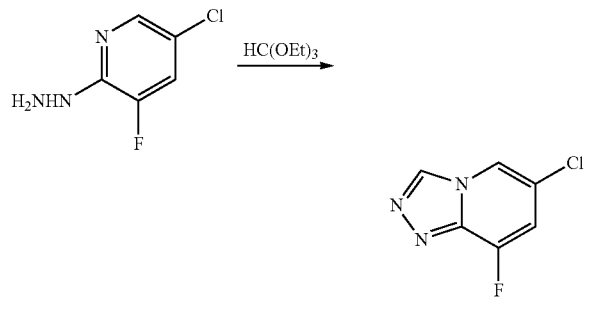

To a stirring solution of 5-chloro-3-fluoro-2-hydrazinylpyridine (1.0 g, 6.21 mmol) in triethoxymethane (15 mL) with molecular sieves was added catalytic formic acid. The reaction was heated to 100° C. and stirred for 5 h. The reaction was then cooled and concentrated, and the crude was triturated with diethyl ether to afford the desired compound as off white solid (710 mg, 4.14 mmol). (m/z): [M+H]$^+$ calculated for C$_6$H$_3$ClFN$_3$ 173.0 found 173.0.

Preparation 15: tert-butyl 3-(((6-chloro-[1,2,4]triazolo[4,3-a]pyridin-8-yl)oxy)methyl)azetidine-1-carboxylate

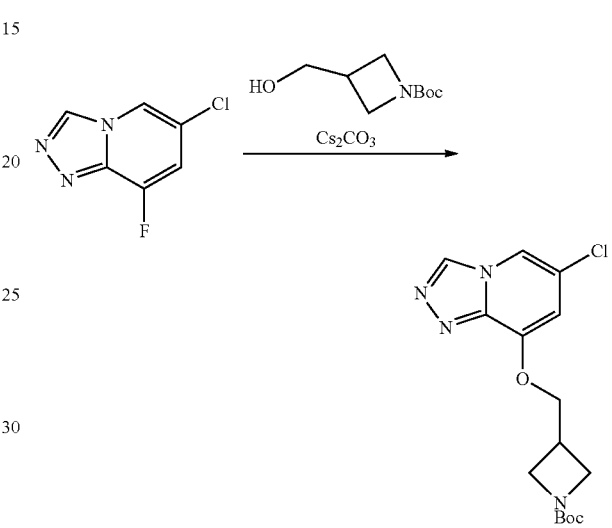

To a stirring solution of tert-butyl 6-chloro-8-fluoro-[1,2,4]triazolo[4,3-a]pyridine (700 mg, 4.09 mmol) in DMSO (20 mL) was added tert-butyl 3-(hydroxymethyl)azetidine-1-carboxylate (919 mg, 4.91 mmol) and Cs$_2$CO$_3$ (2.66 g, 8.18 mmol) and reaction was heated to 120° C. and stirred for 8 h. The reaction was then cooled to room temperature and then partitioned between water and EtOAc. The organic layer was isolated, washed with water and brine, dried over anhydrous Na$_2$SO$_4$, filtered, and then concentrated to afford the crude product as a viscous liquid (730 mg, 2.15 mmol). The product was used without any further purification. (m/z): [M+H]$^+$ calculated for C$_{15}$H$_{19}$ClN$_4$O$_3$ 340.1 found 340.1.

Preparation 16: tert-butyl 3-(((6-(4-hydroxyphenyl)-[1,2,4]triazolo[4,3-a]pyridin-8-yl)oxy)methyl)azetidine-1-carboxylate

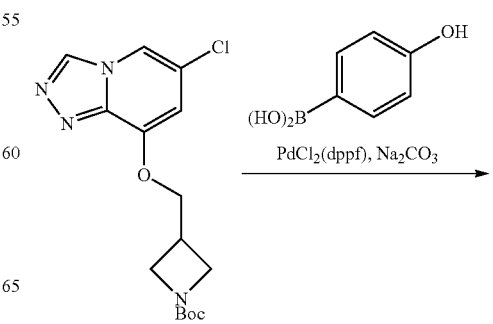

-continued

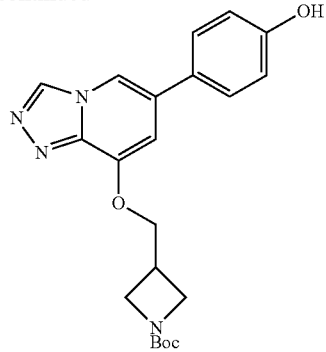

To a stirring solution of tert-butyl 3-(((6-chloro-[1,2,4]triazolo[4,3-a]pyridin-8-yl)oxy)methyl)azetidine-1-carboxylate (700 mg, 2.21 mmol) in DME:EtOH:H$_2$O (7:2.3:1) (31 mL) was added (4-hydroxyphenyl)boronic acid (341 mg, 2.48 mmol) followed by Na$_2$CO$_3$ (655 mg, 6.18 mmol). The reaction mixture was sparged with argon for 15 min and was followed by the addition of PdCl$_2$(dppf) (168 mg, 0.20 mmol). The reaction was heated to 120° C. and stirred for 6 h. The reaction mixture was filtered through a pad of celite, the pad was washed with EtOAc, and the filtrate was diluted with H$_2$O (30 mL). The filtrate was then extracted using EtOAc (2×50 mL). The organic layer was washed with water and dried over Na$_2$SO$_4$, filtered, and then concentrated under reduced pressure to obtain the crude product. Purification by neutral alumina chromatography using a 10% MeOH:DCM solvent system afforded the desired product as an off white solid (400 mg, 1.00 mmol). (m/z): [M+H]$^+$ calculated for C$_{21}$H$_{24}$N$_4$O$_4$ 397.1 found 397.1.

Preparation 17: 4-(8-(azetidin-3-ylmethoxy)-[1,2,4]triazolo[4,3-a]pyridin-6-yl)phenol

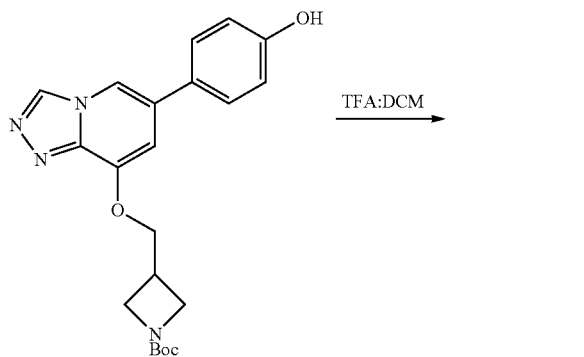

To a stirring solution of tert-butyl 3-(((6-(4-hydroxyphenyl)[1,2,4]triazolo[4,3-a]pyridin-8-yl)oxy)methyl)azetidine-1-carboxylate (350 mg, 0.88 mmol) in DCM (15 mL) was added TFA (2.0 mL). The reaction was stirred at room temperature for 3 h and was then concentrated under reduced pressure. The residue was triturated with diethyl ether to afford the TFA salt of the desired product as a light brown solid (445 mg, 1.50 mmol). (m/z): [M+H]$^+$ calculated for C$_{16}$H$_{16}$N$_4$O$_2$ 297.1 found 297.1.

Example 5: 1-(3-(((6-(4-hydroxyphenyl)-[1,2,4]triazolo[4,3-a]pyridin-8-yl)oxy)methyl)azetidin-1-yl)prop-2-en-1-one

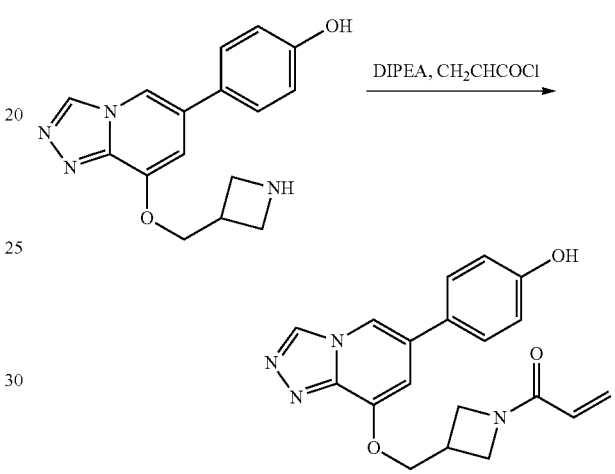

To a stirring solution of 4-(8-(azetidin-3-ylmethoxy)-[1,2,4]triazolo[4,3-a]pyridin-6-yl)phenol (28 mg, 0.069 mmol) in DMF (344 µl) was added DIPEA (72 µl, 412 mmol) and then acryloyl chloride (5.3 µl, 0.065 mmol). The reaction was run for 5 minutes and was then concentrated to dryness in vacuo. The crude residue was redissolved in ~1:1 AcOH:H$_2$O and purified by reverse phase HPLC using a 18-45% MeCN:H$_2$O (with 0.1% TFA) using a Phenomenex 21.2× 250 mm Luna Axia C18 column to afford the desired product as a TFA salt (7.6 mg, 0.022 mmol). (m/z): [M+H]$^+$ calculated for C$_{19}$H$_{18}$N$_4$O$_3$ 351.1 found 351.2.

Preparation 18: 3-chloro-5-(4-hydroxyphenyl)pyrazine-2-carbonitrile

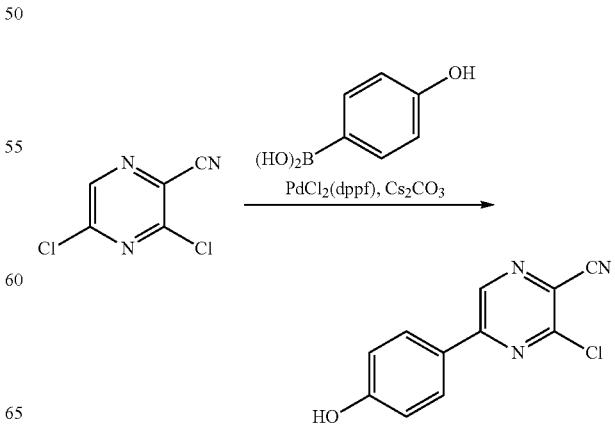

To a stirring solution of 3,5-dichloropyrazine-2-carbonitrile (300 mg, 1.72 mmol) in dioxane:H$_2$O (5.0 mL:1.0 mL) was added (4-hydroxyphenyl)boronic acid (261 mg, 1.89 mmol) followed by Cs$_2$CO$_3$ (1.1 g, 3.44 mmol). The reaction mixture was purged with argon for 5 minutes and then PdCl$_2$(dppf) (140 mg, 0.17 mmol) was added. The reaction was then heated to 100° C. and stirred for 3 h. The reaction was then cooled and filtered through a celite pad and the filtrate was concentrated under reduced pressure to afford the crude product. The crude product was then purified by silica gel column chromatography using a 10-12% EtOAc: hexanes gradient to afford the desired product (140 mg, 0.60 mmol). Regiochemistry was confirmed by NOE analysis. (m/z): [M+H]$^+$ calculated for C$_{11}$H$_6$ClN$_3$O, 233.0 found 233.1.

Preparation 19: tert-butyl 3-(((3-cyano-6-(4-hydroxyphenyl)pyrazin-2-yl)oxy)methyl)azetidine-1-carboxylate

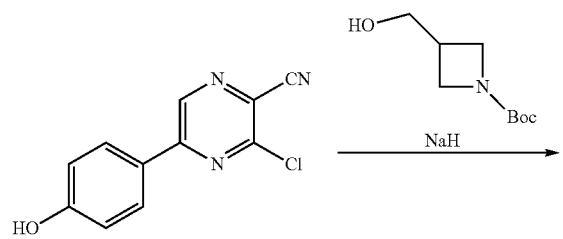

In a dry two neck flask charged with NaH (60% dispersion in mineral oil) (134 mg, 3.37 mmol) was added DMF (2.0 mL) at 0° C. To this was added tert-butyl 3-(hydroxymethyl)azetidine-1-carboxylate (637 mg, 3.37 mmol) dissolved in DMF (4.0 mL). The reaction was stirred at 0° C. for 30 min and then 3-chloro-5-(4-hydroxyphenyl)pyrazine-2-carbonitrile (650 mg, 2.81 mmol) in DMF (4 mL) was added. The reaction was stirred at 0° C. for 30 min. The reaction was then quenched with ice and extracted with EtOAc. The organic layer was dried over Na$_2$SO$_4$, filtered, and concentrated under reduced pressure to afford the crude product. The crude product was purified by silica gel column chromatography using a 20-25% EtOAc:hexanes gradient to afford the desired product (610 mg, 1.60 mmol). (m/z): [M+H]$^+$ calculated for C$_{20}$H$_{22}$N$_4$O$_4$ 383.1 found 383.1.

Preparation 20: tert-butyl 3-(((3-(aminomethyl)-6-(4-hydroxyphenyl)pyrazin-2-yl)oxy)methyl)azetidine-1-carboxylate

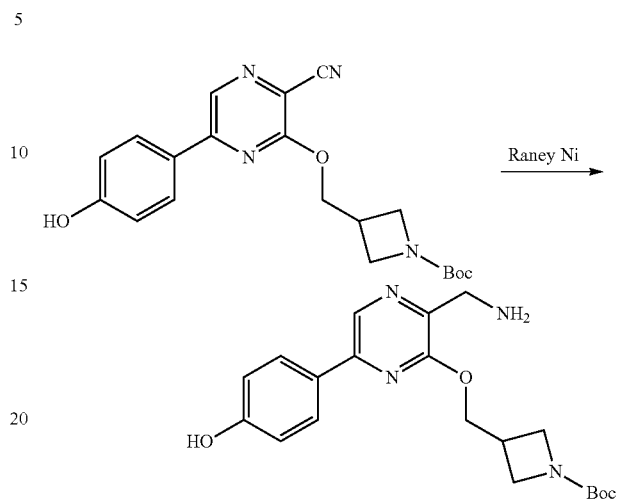

In a dry flask charged with Raney Ni (1.0 g) was added tert-butyl 3-(((3-cyano-6-(4-hydroxyphenyl)pyrazin-2-yl)oxy)methyl)azetidine-1-carboxylate (400 mg, 1.04 mmol) dissolved in MeOH (20 mL) followed by NH$_4$OH (10 mL). The reaction was then set under an atmosphere of hydrogen using a balloon. The reaction was stirred at 25° C. for 16 h. The reaction mixture was then filtered through a pad of celite and the filtrate was concentrated under reduced pressure to obtain the crude product (380 mg, 0.98 mmol). The product was used without any further purification. (m/z): [M+H]$^+$ calculated for C$_{20}$H$_{26}$N$_4$O$_4$ 387.2 found 387.3.

Preparation 21: tert-butyl 3-(((3-(formamidomethyl)-6-(4-hydroxyphenyl)pyrazin-2-yl)oxy)methyl)azetidine-1-carboxylate

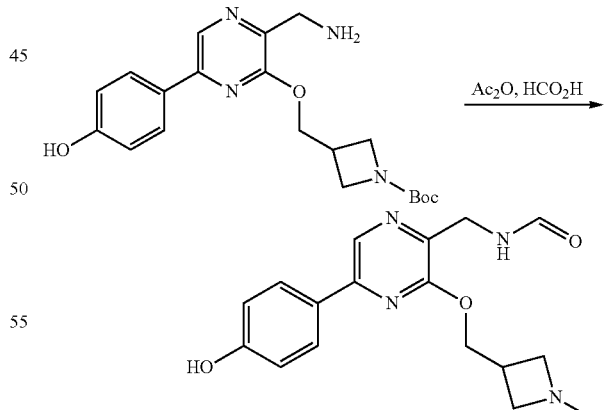

In a dry, sealed pressure tube, a mixture of HCO$_2$H (0.53 mL, 14.25 mmol) and Ac$_2$O (0.87 mL, 9.5 mmol) was heated at 70° C. for 2 h. The formylating mixture was cooled to room temperature and then added to a solution of tert-butyl 3-(((3-(aminomethyl)-6-(4-hydroxyphenyl)pyrazin-2-yl)oxy)methyl)azetidine-1-carboxylate (370 mg, 0.95 mmol) in THF (10 mL) at 0° C. The reaction was stirred at room temperature for 2 h. The reaction was diluted with water and extracted with ethyl acetate. The organic layer was dried over Na$_2$SO$_4$, filtered, and concentrated under reduced pressure to afford the crude product (360 mg, 0.87 mmol). The crude was used in the subsequent reaction with no further purification.

Preparation 22: tert-butyl 3-(((6-(4-hydroxyphenyl)imidazo[1,5-a]pyrazin-8-yl)oxy)methyl)azetidine-1-carboxylate

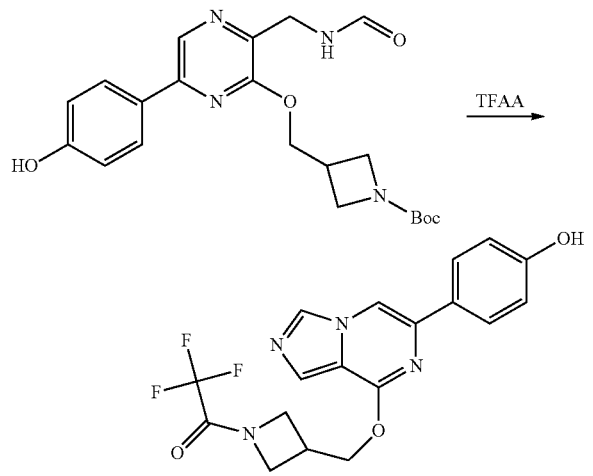

To a stirring solution of tert-butyl 3-(((3-(formamidomethyl)-6-(4-hydroxyphenyl)pyrazin-2-yl)oxy)methyl)azetidine-1-carboxylate (360 mg, 0.86 mmol) in DCM (15 mL) was added TFAA (0.36 mL, 2.60 mmol) at 0° C. The reaction was then warmed to room temperature and stirred for 16 h. The reaction mixture was concentrated under reduced pressure to obtain the crude product which was not purified any further (350 mg, 0.89 mmol). (m/z): [M+H]$^+$ calculated for C$_{18}$H$_{15}$F$_3$N$_4$O$_3$ 393.1 found 393.0.

Preparation 23: 4-(8-(azetidin-3-ylmethoxy)imidazo[1,5-a]pyrazin-6-yl)phenol

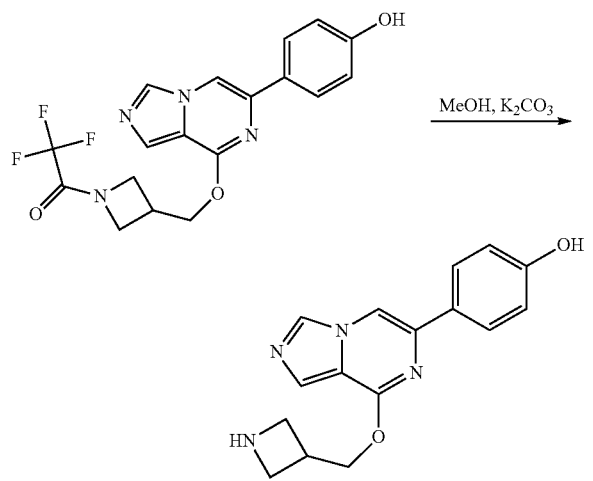

To a stirring solution of 2,2,2-trifluoro-1-(3-(((6-(4-hydroxyphenyl)imidazo[1,5-a]pyrazin-8-yl)oxy)methyl)azetidin-1-yl)ethan-1-one (350 mg, 0.89 mmol) in MeOH (15 mL) at 0° C. was added K$_2$CO$_3$ (360 mg, 2.67 mmol). The reaction was then warmed to room temperature and stirred for 1 h. The reaction was then concentrated under reduced pressure to obtain the crude product. The crude product was purified by reverse phase prep. HPLC to afford the desired product as a TFA salt (90 mg, 0.304 mmol). (m/z): [M+H]$^+$ calculated for C$_{16}$H$_{16}$N$_4$O$_2$ 297.1 found 297.0.

Example 6: 1-(3-(((6-(4-hydroxyphenyl)imidazo[1,5-a]pyrazin-8-yl)oxy)methyl)azetidin-1-yl)prop-2-en-1-one

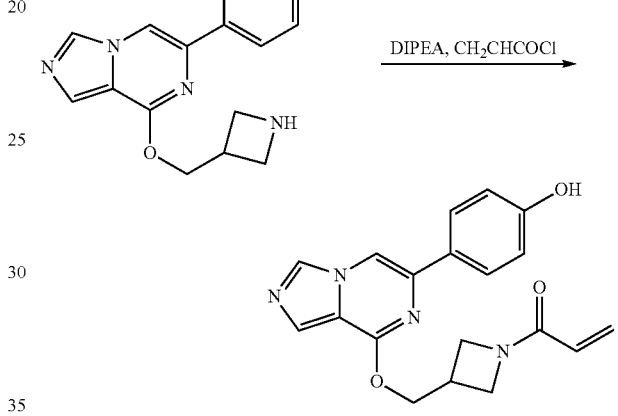

To a stirring solution of 4-(8-(azetidin-3-ylmethoxy)imidazo[1,5-a]pyrazin-6-yl)phenol (28 mg, 0.069 mmol) in DMF (344 μL) was added DIPEA (72 μL, 0.412 mmol) and then acryloyl chloride (5.3 μl, 0.065 mmol). The reaction was run for 5 minutes and was then concentrated to dryness in vacuo. The crude residue was dissolved in ~1:1 AcOH:H$_2$O and purified by reverse phase HPLC using a 18-45% MeCN:H$_2$O (with 0.1% TFA) using a Phenomenex 21.2× 250 mm Luna Axia C18 column to afford the desired product as a TFA salt (11.9 mg, 0.034 mmol). (m/z): [M+H]$^+$ calculated for C$_{19}$H$_{18}$N$_4$O$_3$ 351.1 found 351.1.

Preparation 24: methyl 5-bromo-3-fluoropicolinate

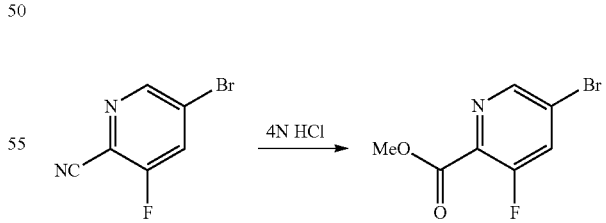

To a stirring solution of 5-bromo-3-fluoropicolinonitrile (8.0 g, 39.80 mmol) in MeOH (80 mL) was added 4N HCl (80 mL). The reaction was stirred under reflux for 30 h. The reaction was then concentrated under reduced pressure and the solid residue was neutralized with saturated NaHCO$_3$ and extracted with ethyl acetate. The organic layer was washed with brine, dried over Na$_2$SO$_4$, filtered and concentrated under reduced pressure to obtain the crude product.

The crude was purified by flash chromatography on silica gel using a 8-10% EtOAc:hexane gradient to afford the desired product as a white solid (5.5 g, 23.5 mmol). (m/z): [M+H]+ calculated for C7H5BrFNO2 234.9 found 234.9.

Preparation 25:
(5-bromo-3-fluoropyridin-2-yl)methanol

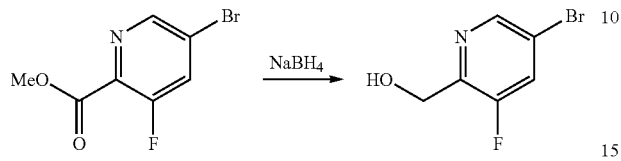

To a stirring solution of methyl 5-bromo-3-fluoropicolinate (2×8.0 g, 34.18 mmol) in MeOH:THF (1:1) (2×400 ml) was added NaBH4 (2×3.9 g, 102.54 mmol) portion wise at 0° C. and then the reaction mixture was stirred for 2 h at room temperature. The solvent was removed under reduced pressure and the crude residue was diluted with water and extracted with DCM. The organic layer was further washed with water and brine, dried over Na2SO4, filtered, and concentrated under reduced pressure to afford the desired product as a white solid (13.01 g, 63.15 mmol). (m/z): [M+H]+ calculated for C6H5BrFNO 206.9 found 207.0.

Preparation 26:
5-bromo-2-(bromomethyl)-3-fluoropyridine

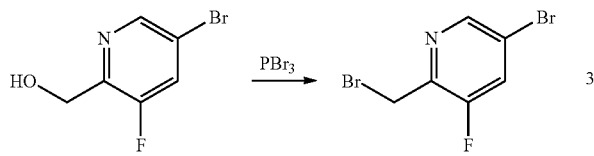

To a stirring solution of (5-bromo-3-fluoropyridin-2-yl)methanol (13.0 g, 63.41 mmol) in DCM (200 ml) was added PBr3 (36.1 mL, 380.48 mmol) drop wise at 0° C. The reaction mixture was then stirred at room temperature for 4 h. The reaction mixture was carefully poured into saturated NaHCO3 in small portions and the pH was maintained at about 6. The solution was then extracted with DCM, dried over Na2SO4, filtered, and concentrated under reduced pressure. The crude product was then purified by silica gel column chromatography using a 10% EtOAc:hexanes gradient to afford the desired product as white solid (12.05 g, 44.81 mmol). (m/z): [M+H]+ calculated for C6H4Br2FN 266.8 found 267.1.

Preparation 27:2-((5-bromo-3-fluoropyridin-2-yl)methy)isoindoline-1,3-dione

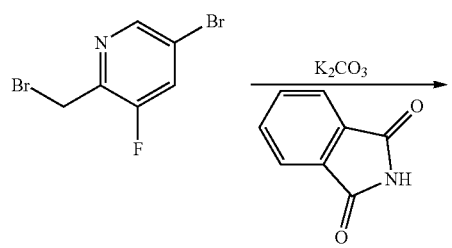

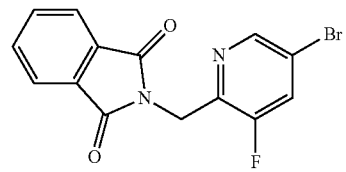

To a stirring solution of 5-bromo-2-(bromomethyl)-3-fluoropyridine (12.0 g, 44.60 mmol) in DMF (100 ml) was added pthalimide (7.21 g, 49.07 mmol) and K2CO3 (12.30 g, 89.20 mmol). The reaction was stirred at room temperature for 16 h. The reaction was then diluted with water and extracted with ethyl acetate. The organic fractions were combined and washed with cold water and brine, dried over Na2SO4, filtered, and concentrated to afford the crude product. The crude product was used in the subsequent reaction without any further purification (15.02 g). (m/z): [M+H]+ calculated for C14H8BrFN2O2 335.9 found 335.9.

Preparation 28:
(5-bromo-3-fluoropyridin-2-yl)methanamine

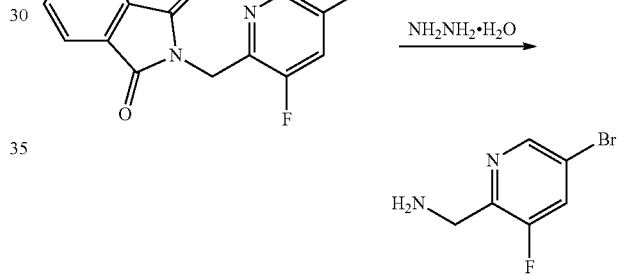

To a stirring solution of 2-((5-bromo-3-fluoropyridin-2-yl)methyl)isoindoline-1,3-dione (15.0 g, 44.77 mmol) in EtOH (300 ml) was added hydrazine hydrate (6.2 mL, 134.32 mmol). The reaction was then stirred at 50° C. for 6 h. The reaction was then cooled and concentrated under reduced pressure and dried completely under high vacuum. The solid residue was diluted with excess DCM, triturated and filtered through sintered funnel, and the residue was washed twice with DCM. The filtrate was concentrated under reduced pressure to obtain the desired product as a light brown viscous liquid (9.1 g, 44.34 mmol). (m/z): [M+H]+ calculated for C6H6BrFN2 205.9 found 205.8.

Preparation 29:
N-((5-bromo-3-fluoropyridin-2-yl)methyl)formamide

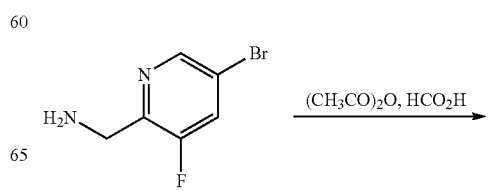

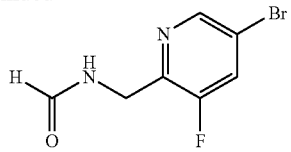

In a sealed tube, acetic anhydride (41.4 mL, 439.02 mmol) and formic acid (19.86 mL, 526.8 mmol) was stirred at 70° C. for 2 h to generate a formylating mixture. To a separate flask containing (5-bromo-3-fluoropyridin-2-yl)methanamine (9.0 g, 43.90 mmol) in THF (200 mL) at 0° C. was added the formylating mixture in a dropwise fashion. The reaction was maintained at 0° C. and stirred for 2 h. The reaction was then diluted with water and extracted with ethyl acetate. The organic layer was dried over $Na_2SO_4$, filtered, and concentrated under reduced pressure to afford the desired product as light brown solid (10.5 g). The crude product was used in the subsequent reaction with no further purification. (m/z): $[M+H]^+$ calculated for $C_7H_6BrFN_2O$, 233.9 found 233.9.

Preparation 30: 6-bromo-8-fluoroimidazo[1,5-a]pyridine

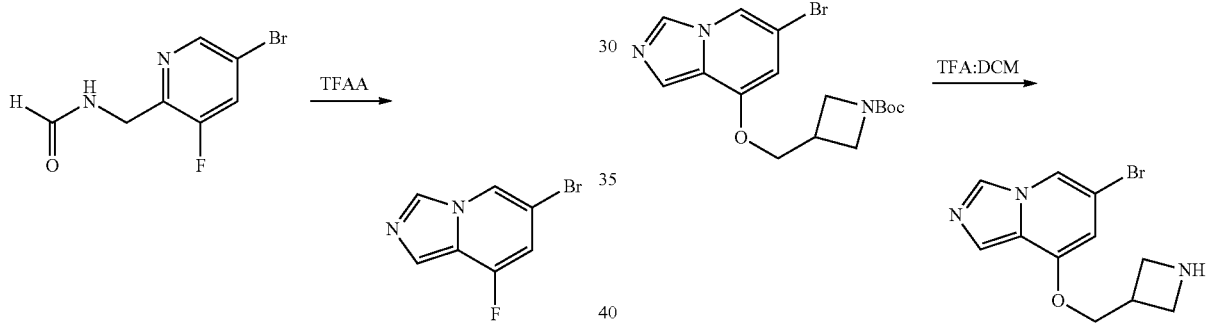

To a stirring solution of N-((5-bromo-3-fluoropyridin-2-yl)methyl)formamide (10.5 g, 45.06 mmol) in DCM (100 mL) was added TFAA (trifluoroacetic anhydride, 20.27 ml, 135.1 mmol) at 0° C. dropwise. The reaction was warmed to room temperature and stirred for 3 h. The reaction was cooled to 0° C. and slowly quenched with saturated $NaHCO_3$ and extracted with DCM. The organic layer was concentrated under reduced pressure to obtain the crude product which was purified by silica gel column chromatography using a 20-25% EtOAc:hexane gradient to afford the desired product as a light-brown solid (5.05 g, 23.49 mmol). (m/z): $[M+H]^+$ calculated for $C_7H_4BrFN_2$ 215.9 found 215.9.

Preparation 31: tert-butyl 3-(((6-bromoimidazo[1,5-a]pyridin-8-yl)oxy)methyl)azetidine-1-carboxylate

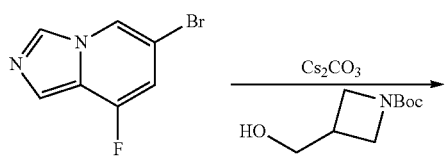

To a stirring solution of 6-bromo-8-fluoroimidazo[1,5-a]pyridine (1.5 g, 6.97 mmol) in DMSO (20 mL) was added tert-butyl 3-(hydroxymethyl)azetidine-1-carboxylate (1.56 g, 8.37 mmol) and $Cs_2CO_3$ (4.54 g, 13.94 mmol) at room temperature. The reaction was stirred at 120° C. for 6 h in a sealed vial. The reaction was diluted with water and extracted using EtOAc. The combined organic layers were washed with brine, dried over $Na_2SO_4$, filtered, and concentrated to obtain the crude residue. Purification of the crude by silica gel column chromatography using a 30-40% EtOAc:hex gradient afforded the desired product (1.8 g, 4.72 mmol). (m/z): $[M+H]^+$ calculated for $C_{16}H_{20}BrN_3O_3$ 383.0 found 382.9.

Preparation 32: 8-(azetidin-3-ylmethoxy)-6-bromoimidazo[1,5-a]pyridine

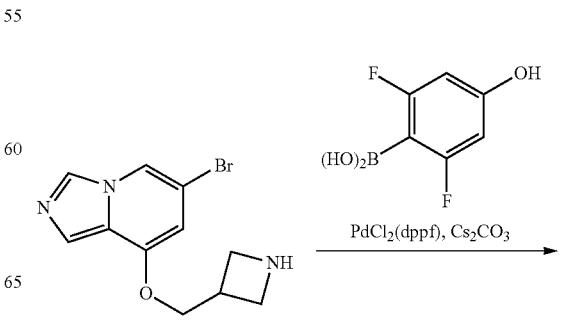

To a stirring solution of tert-butyl 3-(((6-bromoimidazo[1,5-a]pyridin-8-yl)oxy)methyl)azetidine-1-carboxylate (1.8 g, 4.72 mmol) in DCM (18 mL) was added TFA (9.0 mL) at 0° C. under a nitrogen atmosphere. The reaction mixture was stirred for 2-3 h at room temperature. The reaction was then concentrated and triturated with diethyl ether to afford the desired product as a TFA salt (2.2 g, 5.57 mmol). (m/z): $[M+H]^+$ calculated for $C_{11}H_{12}BrN_3O$, 283.0 found 282.9.

Preparation 33: 4-(8-(azetidin-3-ylmethoxy)imidazo[1,5-a]pyridin-6-yl)-3,5-difluorophenol

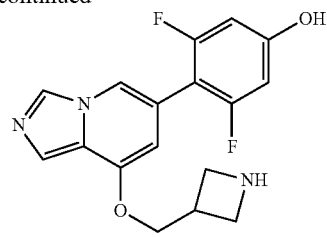

To a stirring solution of 8-(azetidin-3-ylmethoxy)-6-bromoimidazo[1,5-a]pyridine (70 mg, 0.177 mmol) in dioxane (1.42 mL) was added (2,6-difluoro-4-hydroxyphenyl)boronic acid (40 mg, 0.230 mmol), followed by a solution of cesium carbonate (174 mg, 0.533 mmol) in water (354 µL). The reaction was sealed and heated to 110° C. overnight. The reactions were concentrated in vacuo and used in the subsequent reaction without further purification. (m/z): [M+H]$^+$ calculated for $C_{17}H_{15}FN_3O_2$ 332.1 found 332.

Example 7: 1-(3-(((6-(2,6-difluoro-4-hydroxyphenyl)imidazo[1,5-a]pyridin-8-yl)oxy)methyl)azetidin-1-yl)prop-2-en-1-one

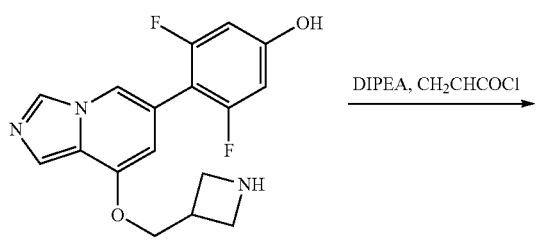

To a stirring solution of 4-(8-(azetidin-3-ylmethoxy)imidazo[1,5-a]pyridin-6-yl)-3,5-difluorophenol in DMF (619 µl) was added DIPEA (130 µl, 0.742 mmol) and then acryloyl chloride (5.03 µl, 0.062 mmol). The reaction was stirred for 10 minutes and then concentrated in vacuo. The crude residue was dissolved in ~1:1 AcOH:H$_2$O and then purified by reverse phase HPLC using a 10-45% MeCN:H$_2$O gradient (with 0.1% TFA) using a Phenomenex 21.2× 250 mm Luna Axia C18 column to afford the desired product as a TFA salt (1.4 mg, 0.004 mmol). (m/z): [M+H]$^+$ calculated for $C_{20}H_{17}F_2N_3O_3$ 386.1 found 386.1.

Preparation 34: 4-(8-(azetidin-3-ylmethoxy)imidazo[1,5-a]pyridin-6-yl)-2,3-difluorophenol

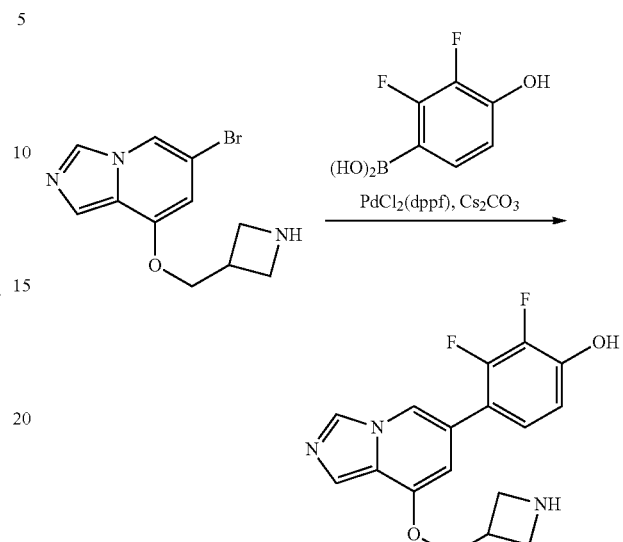

To a stirring solution of 8-(azetidin-3-ylmethoxy)-6-bromoimidazo[1,5-a]pyridine (70 mg, 0.177 mmol) in dioxane (1.42 mL) was added (2,3-difluoro-4-hydroxyphenyl)boronic acid (40 mg, 0.230 mmol), followed by a solution of cesium carbonate (174 mg, 0.533 mmol) in water (354 µL). The reaction was sealed and heated to 110° C. overnight. The reactions were concentrated in vacuo and used in the subsequent reaction without further purification. (m/z): [M+H]$^+$ calculated for $C_{17}H_{15}FN_3O_2$ 332.1 found 332.

Example 8: 1-(3-(((6-(2,3-difluoro-4-hydroxyphenyl)imidazo[1,5-a]pyridin-8-yl)oxy)methyl)azetidin-1-yl)prop-2-en-1-one

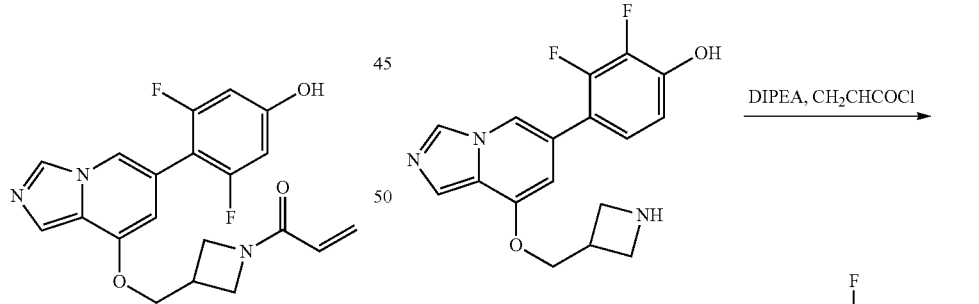

To a stirring solution of 4-(8-(azetidin-3-ylmethoxy)imidazo[1,5-a]pyridin-6-yl)-2,3-difluorophenol in DMF (619 µl) was added DIPEA (130 µl, 0.742 mmol) and then acryloyl chloride (5.03 μl, 0.062 mmol). The reaction was stirred for 10 minutes and then concentrated in vacuo. The crude residue was dissolved in ~1:1 AcOH:H$_2$O and then purified by reverse phase HPLC using a 10-50% MeCN:H$_2$O gradient (with 0.1% TFA) using a Phenomenex 21.2×250 mm Luna Axia C18 column to afford the desired product as a TFA salt (3.3 mg, 0.009 mmol). (m/z): [M+H]$^+$ calculated for C$_{20}$H$_{17}$F$_2$N$_3$O$_3$ 386.1 found 386.1.

Preparation 35: 4-(8-(azetidin-3-ylmethoxy)imidazo[1,5-a]pyridin-6-yl)-2-chloro-6-methoxyphenol

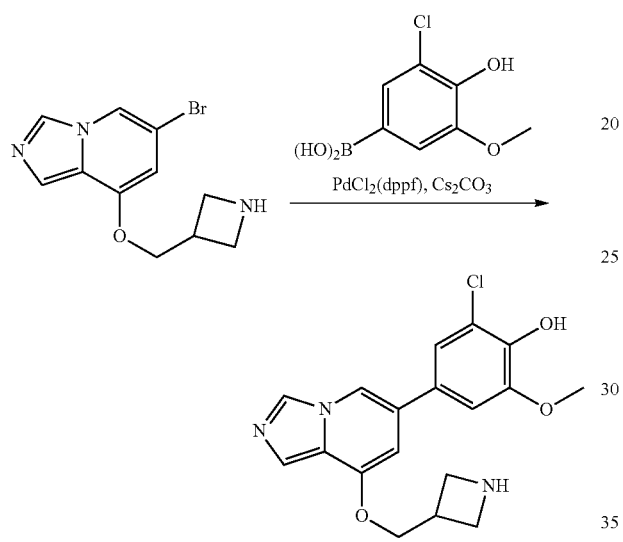

To a stirring solution of 8-(azetidin-3-ylmethoxy)-6-bromoimidazo[1,5-a]pyridine (70 mg, 0.177 mmol) in dioxane (1.42 mL) was added 3-chloro-4-hydroxy-5-methoxyphenylboronic acid (47 mg, 0.230 mmol), followed by a solution of cesium carbonate (174 mg, 0.533 mmol) in water (354 μL). The reaction was sealed and heated to 110° C. overnight. The reactions were concentrated in vacuo and used in the subsequent reaction without further purification. (m/z): [M+H]$^+$ calculated for C$_{18}$H$_{18}$ClN$_3$O$_3$ 361.1 found 361.2.

Example 9: 1-(3-(((6-(3-chloro-4-hydroxy-5-methoxyphenyl)imidazo[1,5-a]pyridin-8-yl)oxy)methyl)azetidin-1-yl)prop-2-en-1-one

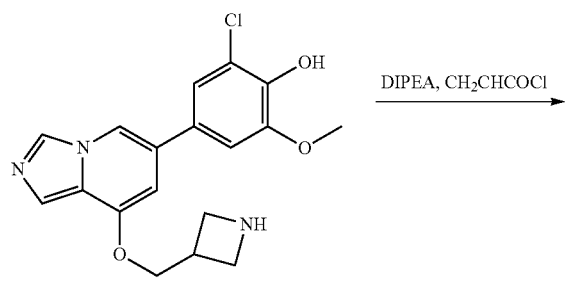

To a stirring solution of 4-(8-(azetidin-3-ylmethoxy)imidazo[1,5-a]pyridin-6-yl)-2-chloro-6-methoxyphenol in DMF (619 μl) was added DIPEA (130 μl, 0.742 mmol) and then acryloyl chloride (5.03 μl, 0.062 mmol). The reaction was stirred for 10 minutes and then concentrated in vacuo. The crude residue was dissolved in ~1:1 AcOH:H$_2$O and then purified by reverse phase HPLC using a 10-50% MeCN:H$_2$O gradient (with 0.1% TFA) using a Phenomenex 21.2×250 mm Luna Axia C18 column to afford the desired product as a TFA salt (2.8 mg, 0.007 mmol). (m/z): [M+H]$^+$ calculated for C$_{21}$H$_{20}$ClN$_3$O$_4$ 415.1 found 415.2.

Preparation 36: tert-butyl (1R,3S,5S)-3-(((6-(4-hydroxyphenyl)imidazo[1,5-a]pyridin-8-yl)oxy)-8-azabicyclo[3.2.1]octane-8-carboxylate

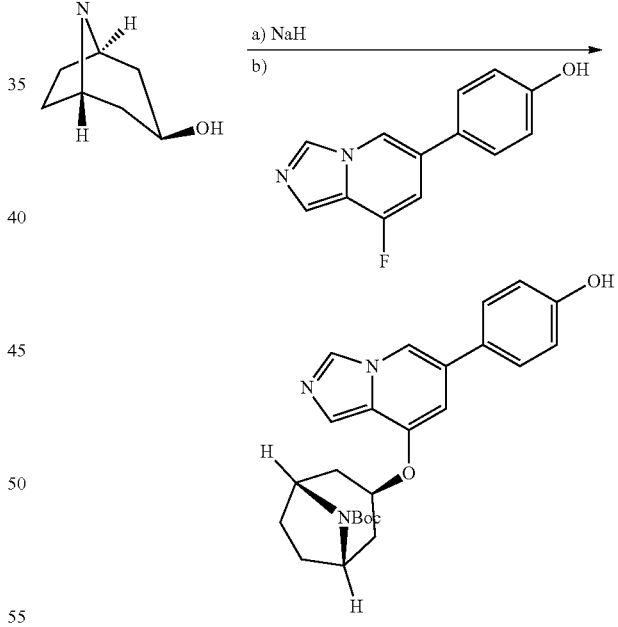

To a solution of tert-Butyl 3-exo-hydroxy-8-azabicyclo[3.2.1]octane-8-carboxylate (149 mg, 0.657 mmol) in DMF (2.5 mL) at 0° C. was added potassium bis(trimethylsilyl)amide solution (1 M in THF) (1.18 mL, 1.183 mmol) and the reaction was stirred at 0° C. for 10 minutes, 10 minutes at rt, then 5 minutes at 0° C. A solution of 4-(8-fluoroimidazo[1,5-a]pyridin-6-yl)phenol (100 mg, 0.438 mmol) in DMF (375 uL) was then added to the solution at 0° C. and the black reaction was heated to 50° C. and stirred for 2 hours. The reaction was quenched with 5 mL H$_2$O and extracted with 3×5 mL EtOAc. The organic extracts were combined and dried over Na₂SO₄, filtered, and concentrated onto celite. Purification by silica gel column chromatography using a 0-100% gradient yielded the product as an orange solid (79 mg, 0.181 mmol). (m/z): [M+H]⁺ calculated for $C_{29}H_{25}N_3O_4$ 436.2 found 436.

Preparation 37: 4-(8-(((1R,3S,5S)-8-azabicyclo[3.2.1]octan-3-yl)oxy)imidazo[1,5-a]pyridin-6-yl)phenol

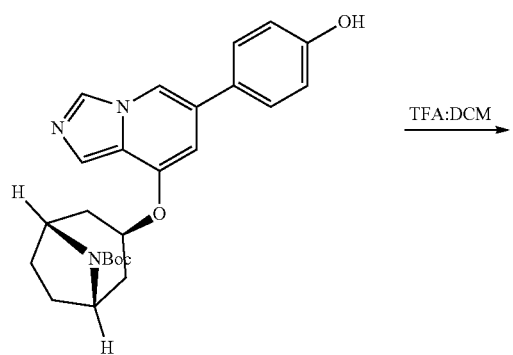

To a stirring solution of tert-butyl (1R,3S,5S)-3-((6-(4-hydroxyphenyl)imidazo[1,5-a]pyridin-8-yl)oxy)-8-azabicyclo[3.2.1]octane-8-carboxylate (79 mg, 0.181 mmol) in DCM (500 μL) was added TFA (500 μL). The reaction was stirred for 2 hours and then concentrated in vacuo to afford the crude product as a TFA salt. The crude product was used without any further purification and 100% yield was assumed (61 mg, 0.181 mmol). (m/z): [M+H]⁺ calculated for $C_{20}H_{21}N_3O_2$ 336.2 found 336.

Example 10: 1-((1R,3S,5S)-3-((6-(4-hydroxyphenyl)imidazo[1,5-a]pyridin-8-yl)oxy)-8-azabicyclo[3.2.1]octan-8-yl)prop-2-en-1-one

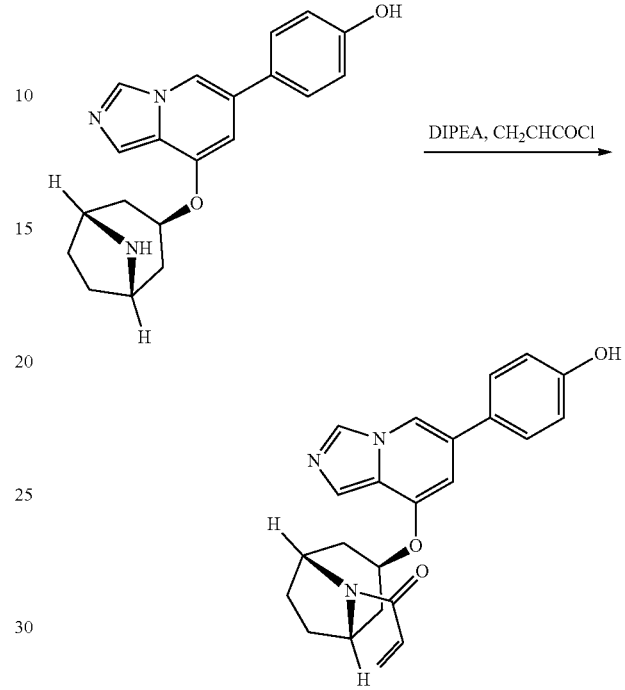

To a stirring solution of 4-(8-(((1R,3S,5S)-8-azabicyclo[3.2.1]octan-3-yl)oxy)imidazo[1,5-a]pyridin-6-yl)phenol (61 mg, 0.136 mmol) in DMF (950 μL) was added DIPEA (143 μL, 0.816 mmol) and then acryloyl chloride (8.84 μL, 0.015 mmol). The reaction was stirred for 5 minutes and concentrated in vacuo. The crude residue was dissolved in ~1:1 AcOH:H₂O and purified by reverse phase HPLC using a 10-50% MeCN:H₂O gradient (with 0.1% TFA) using a Phenomenex 21.2×250 mm Luna Axia C18 column to afford the desired product as a TFA salt (12 mg, 0.031 mmol). (m/z): [M+H]⁺ calculated for $C_{23}H_{23}N_3O_3$ 390.2 found 390.0.

Preparation 38: tert-butyl 3-(((6-bromoimidazo[1,5-a]pyridin-8-yl)oxy)methyl)azetidine-1-carboxylate

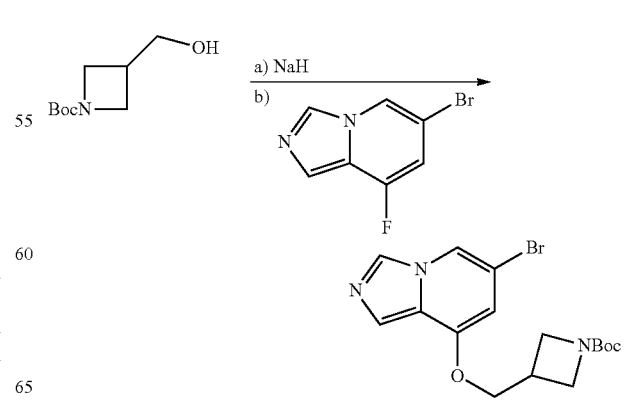

To a solution of tert-butyl 3-(hydroxymethyl)azetidine-1-carboxylate (1.22 g, 6.51 mmol) in DMF (15 mL) at 0° C. was added sodium hydride (60% dispersion in mineral oil) (279 mg, 6.98 mmol) and the reaction was warmed to room temperature and stirred for 30 minutes. The alkoxide suspension was then added dropwise to a stirring solution of 4-(8-fluoroimidazo[1,5-a]pyridin-6-yl)phenol (50 mg, 0.219 mmol) in DMF (8.25 mL) and the resulting reaction was warmed to room temperature and stirred for 24 hours. The reaction was quenched with 60 mL H$_2$O and extracted with 3×25 mL EtOAc. The organic extracts were combined, dried over Na$_2$SO$_4$, filtered, and concentrated onto celite. The crude material was purified by silica gel column chromatography using a 0-80% EtOAc:hexanes gradient to afford the product as a white solid (1.48 g, 3.87 mmol). (m/z): [M+H]$^+$ calculated for C$_{11}$H$_{12}$BrN$_3$O, 383.0 found 382.9.

Preparation 39: tert-butyl 3-(((6-(4-hydroxyphenyl)imidazo[1,5-a]pyridin-8-yl)oxy)methyl)azetidine-1-carboxylate

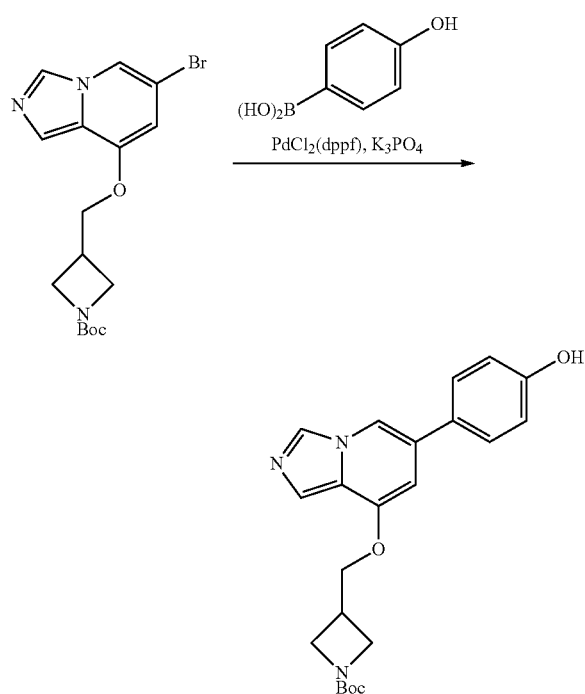 [SMILES: CC(C)(C)OC(=O)N1CC(COc2cc(Br)cn3cncc23)C1 ; OB(O)c1ccc(O)cc1 ; CC(C)(C)OC(=O)N1CC(COc2cc(-c3ccc(O)cc3)cn3cncc23)C1]

To a solution of tert-butyl 3-(((6-bromoimidazo[1,5-a]pyridin-8-yl)oxy)methyl)azetidine-1-carboxylate (889 mg, 2.33 mmol) in dioxane (9.3 mL) was added (4-hydroxyphenyl)boronic acid (385 mg, 2.79 mmol), potassium phosphate, tribasic (1481 mg, 6.98 mmol) in water (2.3 mL), and dichloro[1,1'-bis(diphenylphosphino)ferrocene]palladium (ii) dichloromethane adduct (380 mg, 0.465 mmol). The vial was sealed and heated to 110° C. for 18 hours. The reaction was then cooled and concentrated onto celite in vacuo to afford the crude product. The crude product was then purified by silica gel column chromatography using a 10-100% EtOAc:Hex gradient to afford the desired product. (m/z): [M+H]$^+$ calculated for C$_{22}$H$_{25}$N$_3$O$_4$ 396.2 found 396.0.

Preparation 40: 4-(8-(azetidin-3-ylmethoxy)imidazo[1,5-a]pyridin-6-yl)phenol

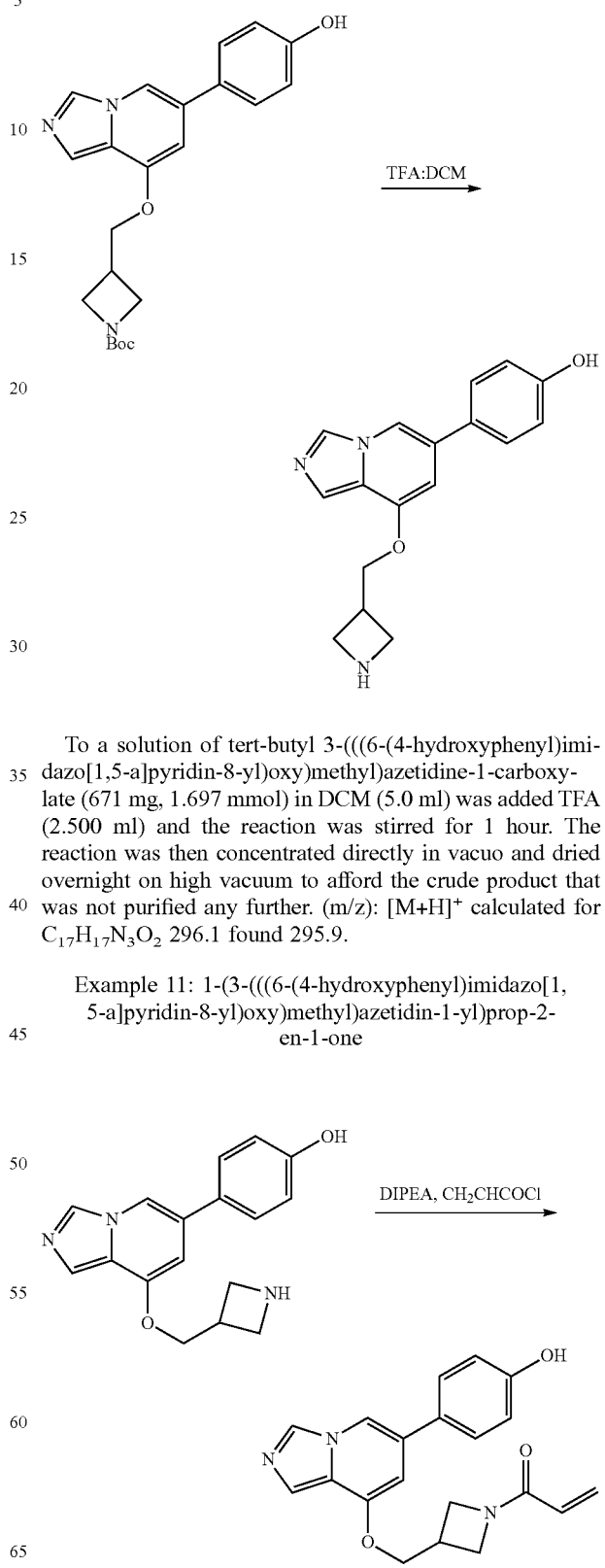

To a solution of tert-butyl 3-(((6-(4-hydroxyphenyl)imidazo[1,5-a]pyridin-8-yl)oxy)methyl)azetidine-1-carboxylate (671 mg, 1.697 mmol) in DCM (5.0 ml) was added TFA (2.500 ml) and the reaction was stirred for 1 hour. The reaction was then concentrated directly in vacuo and dried overnight on high vacuum to afford the crude product that was not purified any further. (m/z): [M+H]$^+$ calculated for C$_{17}$H$_{17}$N$_3$O$_2$ 296.1 found 295.9.

Example 11: 1-(3-(((6-(4-hydroxyphenyl)imidazo[1,5-a]pyridin-8-yl)oxy)methyl)azetidin-1-yl)prop-2-en-1-one To a stirring solution of 4-(8-(azetidin-3-ylmethoxy)imidazo[1,5-a]pyridin-6-yl)phenol (39 mg, 0.095 mmol) in DMF (475 μL) was added DIPEA (83 ΞL, 0.475 mmol) and then acryloyl chloride (7.7 μL, 0.095 mmol). The reaction was stirred for 5 minutes and concentrated in vacuo. The crude residue was dissolved in ~1:1 AcOH:H₂O and purified by reverse phase HPLC using a 5-45% MeCN:H₂O gradient (with 0.1% TFA) using a Phenomenex 21.2×250 mm Luna Axia C18 column to afford the desired product as a TFA salt (2.4 mg, 0.007 mmol). (m/z): [M+H]⁺ calculated for $C_{20}H_{19}N_3O_3$ 350.1 found 350.1. ¹H NMR (400 MHz, DMSO-d₆) δ 9.19 (s, 1H), 8.37 (s, 1H), 7.85 (s, 1H), 7.55 (d, J=8.5 Hz, 2H), 6.88 (d, J=8.5 Hz, 2H), 6.80 (s, 1H), 6.32 (dd, J=16.9, 10.2 Hz, 1H), 6.10 (dd, J=16.9, 1.8 Hz, 1H), 5.65 (dd, J=10.3, 1.8 Hz, 1H), 4.47 (d, J=6.4 Hz, 2H), 4.38 (t, J=8.6 Hz, 1H), 3.79 (dd, J=10.1, 5.3 Hz, 1H).

Preparation 41: tert-butyl 3-(((6-bromoimidazo[1,5-a]pyridin-8-yl)oxy)methyl)azetidine-1-carboxylate

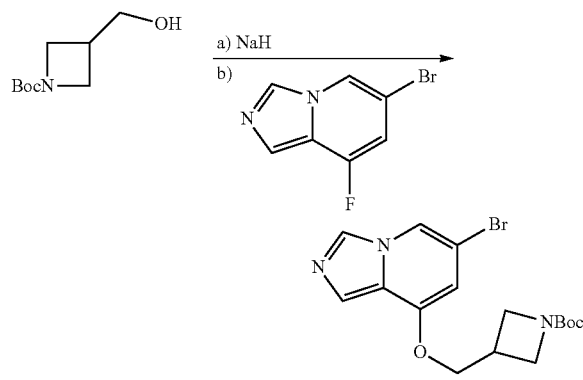

To a solution of tert-butyl 3-(hydroxymethyl)azetidine-1-carboxylate (1.22 g, 6.51 mmol) in DMF (15 mL) at 0° C. was added sodium hydride (60% dispersion in mineral oil) (279 mg, 6.98 mmol) and the reaction was warmed to room temperature and stirred for 30 minutes. The alkoxide suspension was then added dropwise to a stirring solution of 4-(8-fluoroimidazo[1,5-a]pyridin-6-yl)phenol (50 mg, 0.219 mmol) in DMF (8.25 mL) and the resulting reaction was warmed to room temperature and stirred for 24 hours. The reaction was quenched with 60 mL H₂O and extracted with 3×25 mL EtOAc. The organic extracts were combined, dried over Na₂SO₄, filtered, and concentrated onto celite. The crude material was purified by silica gel column chromatography using a 0-80% EtOAc:hexanes gradient to afford the product as a white solid (1.48 g, 3.87 mmol). (m/z): [M+H]⁺ calculated for $C_{11}H_{12}BrN_3O$ 283.0 found 282.9.

Preparation 42: tert-butyl 3-(((6-(3-chloro-4-hydroxyphenyl)imidazo[1,5-a]pyridin-8-yl)oxy)methyl)azetidine-1-carboxylate

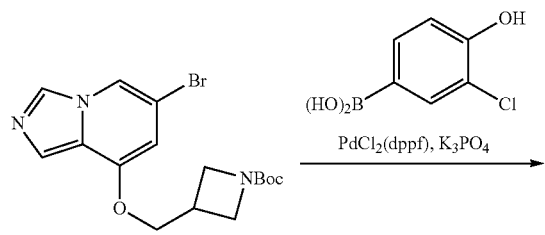

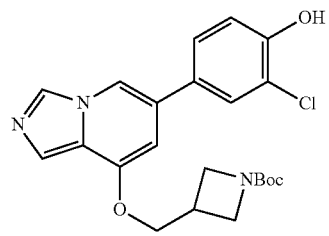

To a stirring solution of tert-butyl 3-(((6-bromoimidazo[1,5-a]pyridin-8-yl)oxy)methyl)azetidine-1-carboxylate (370 mg, 0.968 mmol) in dioxane (5.16 mL) was added a solution of potassium phosphate, tribasic (616 mg, 2.90 mmol) in water (1.29 mL), dichloro[1,1'-bis(diphenylphosphino)ferrocene]palladium (158 mg, 0.194 mmol), and 3-chloro-4-hydroxyphenylboronic acid (200 mg, 1.16 mmol). The vial was sealed, heated to 110° C., and stirred for 18 hours. The reaction was then cooled to room temperature and concentrated onto celite. The crude material was purified by silica gel column chromatography using a 10-100% EtOAc:hexane gradient to afford the desired product (143 mg, 0.333 mmol). (m/z): [M+H]⁺ calculated for $C_{22}H_{24}ClN_3O_4$ 431.1 found 431.1.

Preparation 43: 4-(8-(azetidin-3-ylmethoxy)imidazo[1,5-a]pyridin-6-yl)-2-chlorophenol

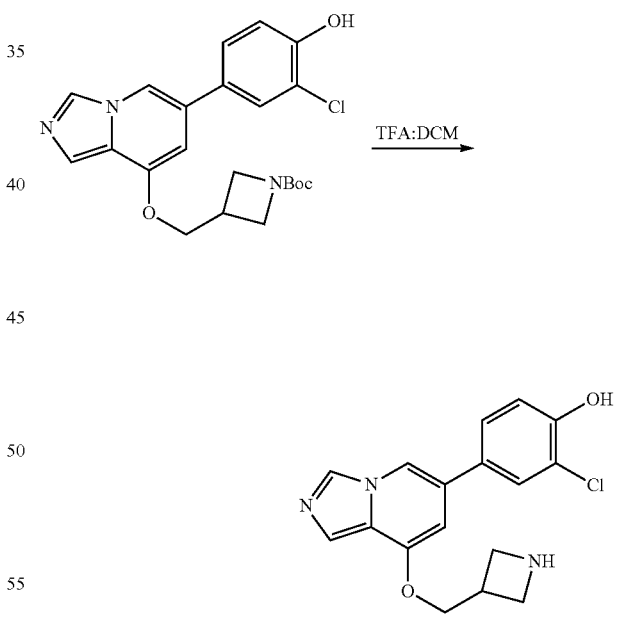

To a stirring solution of tert-butyl tert-butyl 3-(((6-(3-chloro-4-hydroxyphenyl)imidazo[1,5-a]pyridin-8-yl)oxy)methyl)azetidine-1-carboxylate (143 mg, 0.333 mmol) in DCM (500 μL) was added TFA (500 μL). The reaction was stirred for 2 hours and then concentrated in vacuo to afford the crude product as a TFA salt. The crude product was used without any further purification and 100% yield was assumed (110 mg, 0.333 mmol). (m/z): [M+H]⁺ calculated for $C_{17}H_{16}ClN_3O_2$ 331.0 found 331.2.

Example 12: 1-(3-(((6-(3-chloro-4-hydroxyphenyl)imidazo[1,5-a]pyridin-8-yl)oxy)methyl)azetidin-1-yl)prop-2-en-1-one

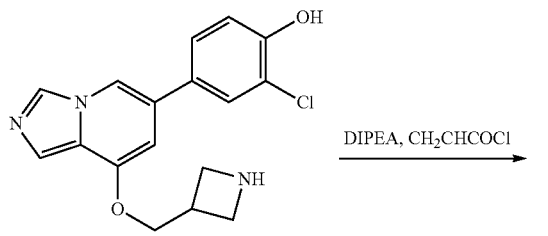

To a solution of 4-(8-(azetidin-3-ylmethoxy)imidazo[1,5-a]pyridin-6-yl)-2-chlorophenol (110 mg, 0.333 mmol) in DMF (1.0 mL) was added DIPEA (192 μL, 1.097 mmol) and then acryloyl chloride (16.1 μL, 0.198 mmol) dropwise. The reaction was stirred for 5 minutes and then concentrated in vacuo. The crude material was dissolved in ~1:1 AcOH:H$_2$O and purified using a 10-50% MeCN:H$_2$O (with 0.1% TFA) gradient on a Phenomenex 21.2×250 mm Luna Axia C18 column to afford the desired product as a TFA salt (8.6 mg, 0.022 mmol). (m/z): [M+H]$^+$ calculated for C$_{20}$H$_{18}$ClN$_3$O$_3$ 385.1 found 385.2.

Preparation 44: tert-butyl 3-(((6-(2-ethyl-5-fluoro-4-hydroxyphenyl)imidazo[1,5-a]pyridin-8-yl)oxy)methyl)azetidine-1-carboxylate

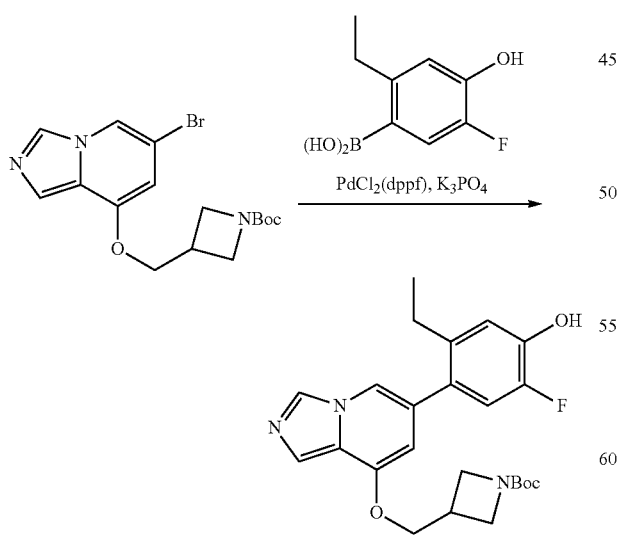

To a stirring solution of tert-butyl 3-(((6-bromoimidazo[1,5-a]pyridin-8-yl)oxy)methyl)azetidine-1-carboxylate (370 mg, 0.968 mmol) in dioxane (5.16 mL) was added a solution of potassium phosphate, tribasic (616 mg, 2.90 mmol) in water (1.29 mL), dichloro[1,1'-bis(diphenylphosphino)ferrocene]palladium (158 mg, 0.194 mmol), and 3-fluoro-4-hydroxyphenylboronic acid (181 mg, 1.16 mmol). The vial was sealed, heated to 110° C., and stirred for 18 hours. The reaction was then cooled to room temperature and concentrated onto celite. The crude material was purified by silica gel column chromatography using a 10-100% EtOAc:hexane gradient to afford the desired product (274 mg, 0.621 mmol). (m/z): [M+H]$^+$ calculated for C$_{24}$H$_{28}$FN$_3$O$_4$ 442.2 found 442.

Preparation 45: 4-(8-(azetidin-3-ylmethoxy)imidazo[1,5-a]pyridin-6-yl)-5-ethyl-2-fluorophenol

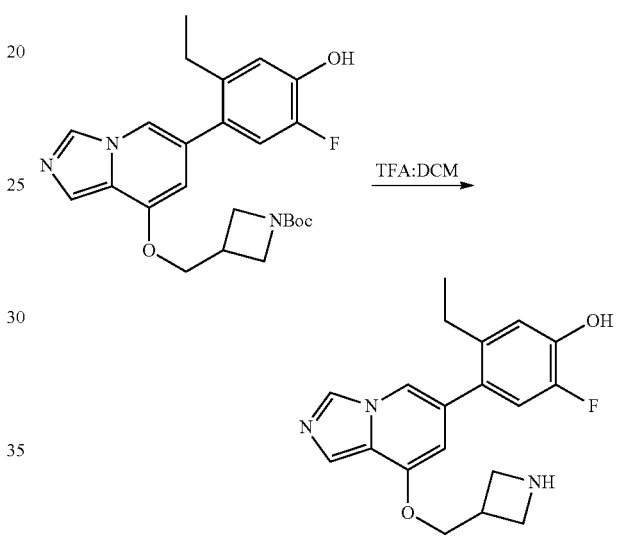

To a stirring solution of tert-butyl 3-(((6-(2-ethyl-5-fluoro-4-hydroxyphenyl) imidazo[1,5-a]pyridin-8-yl)oxy)methyl)azetidine-1-carboxylate (274 mg, 0.621 mmol) in DCM (500 μL) was added TFA (500 μL). The reaction was stirred for 2 hours and then concentrated in vacuo to afford the crude product as a TFA salt. The crude product was used without any further purification and 100% yield was assumed (212 mg, 0.621 mmol). (m/z): [M+H]$^+$ calculated for C$_{17}$H$_{16}$ClN$_3$O$_2$ 342.1 found 342.

Example 13: 1-(3-(((6-(2-ethyl-5-fluoro-4-hydroxyphenyl)imidazo[1,5-a]pyridin-8-yl)oxy)methyl)azetidin-1-yl)prop-2-en-1-one

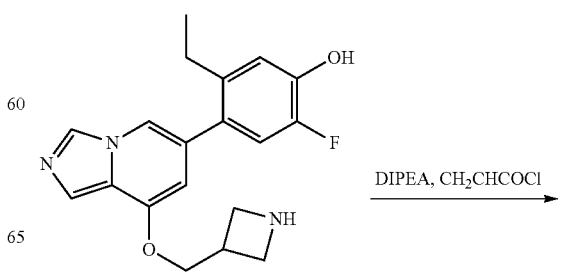

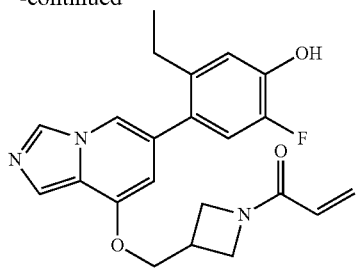

To a solution of 4-(8-(azetidin-3-ylmethoxy)imidazo[1,5-a]pyridin-6-yl)-5-ethyl-2-fluorophenol (100 mg, 0.219 mmol) in DMF (1.1 mL) was added DIPEA (192 μl, 1.097 mmol) and then acryloyl chloride (16.1 μl, 0.198 mmol) dropwise. The reaction was stirred for 5 minutes and then concentrated in vacuo. The crude material was dissolved in ~1:1 AcOH:H$_2$O and purified using a 10-50% MeCN:H$_2$O (with 0.1% TFA) gradient on a Phenomenex 21.2×250 mm Luna Axia C18 column to afford the desired product as a TFA salt (2.1 mg, 0.005 mmol). (m/z): [M+H]$^+$ calculated for C$_{22}$H$_{22}$FN$_3$O$_3$ 396.16 found 396.1.

Preparation 46: tert-butyl 3,3-difluoro-4-((6-(4-hydroxyphenyl)imidazo[1,5-a]pyridin-8-yl)oxy)piperidine-1-carboxylate

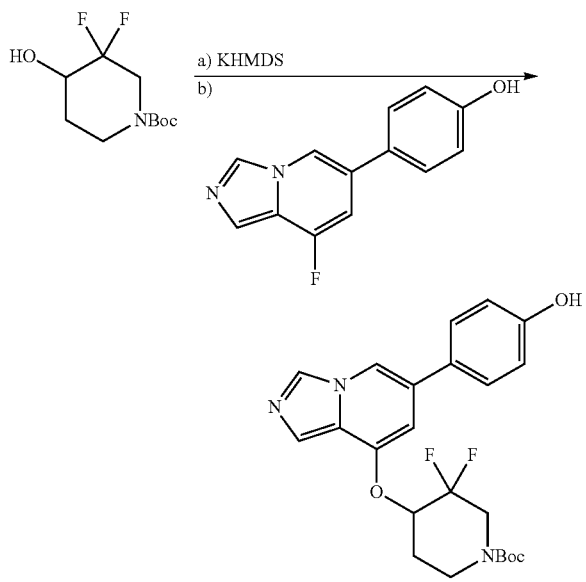

To a stirring solution of tert-butyl 3,3-difluoro-4-hydroxypiperidine-1-carboxylate in DMF (1.64 mL) at 0° C. was added potassium hexamethyldisilazide (1.0 M in THF) (1775 μl, 1.775 mmol) and the reactions were warmed to room temperature and stirred for 20 minutes. The alkoxide solution was cooled to 0° C. and a solution of 4-(8-fluoroimidazo[1,5-a]pyridin-6-yl)phenol (150 mg, 0.657 mmol) was added. The resulting reaction was stirred at room temperature for 3 hours, then diluted with 10 mL H$_2$O and extracted with 3×5 mL EtOAc. The organic extracts were combined and dried over Na$_2$SO$_4$, filtered, and concentrated onto celite. Purification by silica gel column chromatography using a 10-100% EtOAc:hexanes gradient yielded the desired product (176 mg, 0.394 mmol). (m/z): [M+H]$^+$ calculated for C$_{23}$H$_{25}$F$_2$N$_3$O$_4$ 446.1 found 446.

Preparation 47: 4-(8-((3,3-difluoropiperidin-4-yl)oxy)imidazo[1,5-a]pyridin-6-yl)phenol

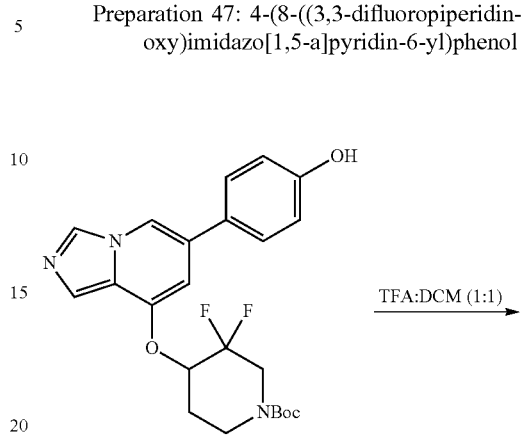

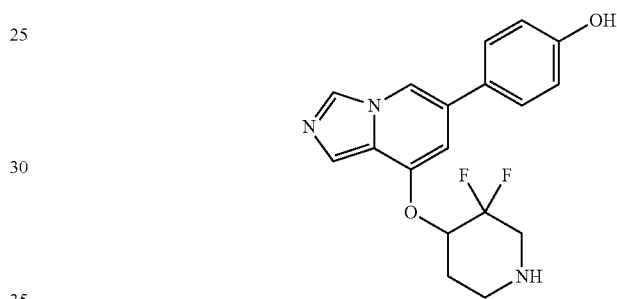

To a stirring solution of tert-butyl 3,3-difluoro-4-((6-(4-hydroxyphenyl) imidazo[1,5-a]pyridin-8-yl)oxy)piperidine-1-carboxylate (176 mg, 0.394 mmol) in DCM (500 μL) was added TFA (500 μL). The reaction was stirred for 2 hours and then concentrated in vacuo to afford the crude product as a TFA salt. The crude product was used without any further purification and 100% yield was assumed (136 mg, 0.394 mmol). (m/z): [M+H]$^+$ calculated for C$_{18}$H$_{17}$F$_2$N$_3$O$_2$ 346.1 found 346.

Example 14: 1-(3,3-difluoro-4-((6-(4-hydroxyphenyl)imidazo[1,5-a]pyridin-8-yl)oxy)piperidin-1-yl)prop-2-en-1-one

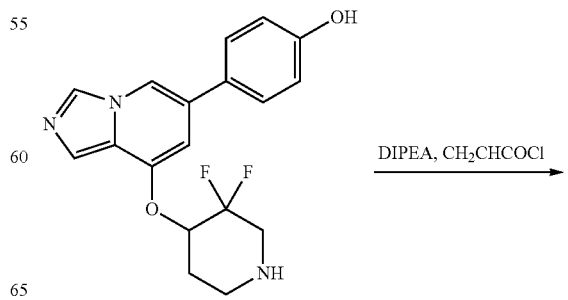

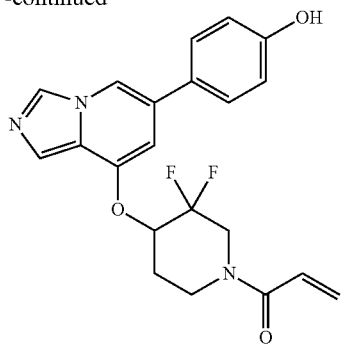

To a solution of 4-(8-((3,3-difluoropiperidin-4-yl)oxy)imidazo[1,5-a]pyridin-6-yl)phenol (136 mg, 0.395 mmol) in DMF (1.98 mL) was added DIPEA (414 µL, 2.37 mmol) and then acryloyl chloride (24.1 µL, 0.296 mmol) dropwise. The reaction was stirred for 5 minutes and then concentrated in vacuo. The crude material was dissolved in ~1:1 AcOH:H$_2$O and purified using a 20-35% MeCN:H$_2$O (with 0.1% TFA) gradient on a Phenomenex 21.2×250 mm Luna Axia C18 column to afford the desired product as a TFA salt (5.6 mg, 0.014 mmol). (m/z): [M+H]$^+$ calculated for C$_{21}$H$_{19}$F$_2$N$_3$O$_3$ 400.1 found 400.1.

Preparation 48: tert-butyl (2R,4R)-4-((6-(4-hydroxyphenyl)imidazo[1,5-a]pyridin-8-yl)oxy)-2-methylpiperidine-1-carboxylate

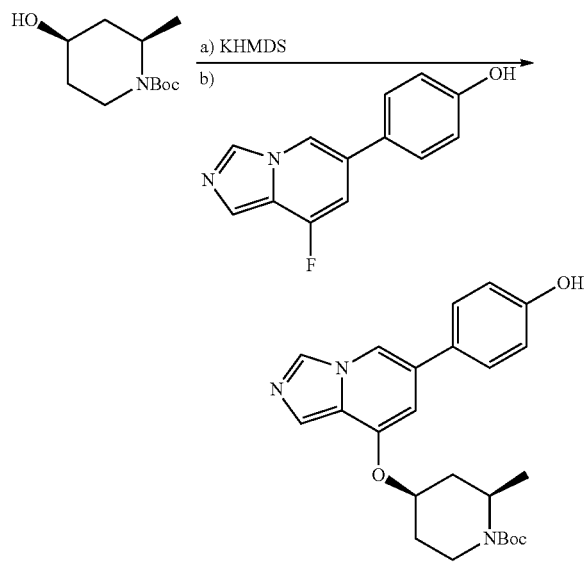

To a stirring solution of tert-butyl (2R,4R)-4-hydroxy-2-methylpiperidine-1-carboxylate (170 mg, 0.789 mmol) in DMF (1.3 mL) was added KHMDS (1.0 M in THF) (1.42 mL, 1.42 mmol). A solution of 4-(8-fluoroimidazo[1,5-a]pyridin-6-yl)phenol (120 mg, 0.526 mmol) in DMF (1.3 mL) was then added to the potassium alkoxide solution. The reaction was stirred at 50° C. for 2 h and then cooled to room temperature. The reaction mixture was diluted with H$_2$O (10 mL) and extracted with 3×5 mL EtOAc. The organic layer was dried over Na$_2$SO$_4$, filtered, and concentrated onto celite. Purification by silica gel column chromatography using a 0-100% EtOAc:hexanes gradient afforded the desired product (49 mg, 0.116 mmol). (m/z): [M+H]$^+$ calculated for C$_{24}$H$_{29}$N$_3$O$_4$ 424.2 found 424.2.

Preparation 49: tert-butyl (2R,4R)-4-((6-(4-hydroxyphenyl)imidazo[1,5-a]pyridin-8-yl)oxy)-2-methylpiperidine-1-carboxylate

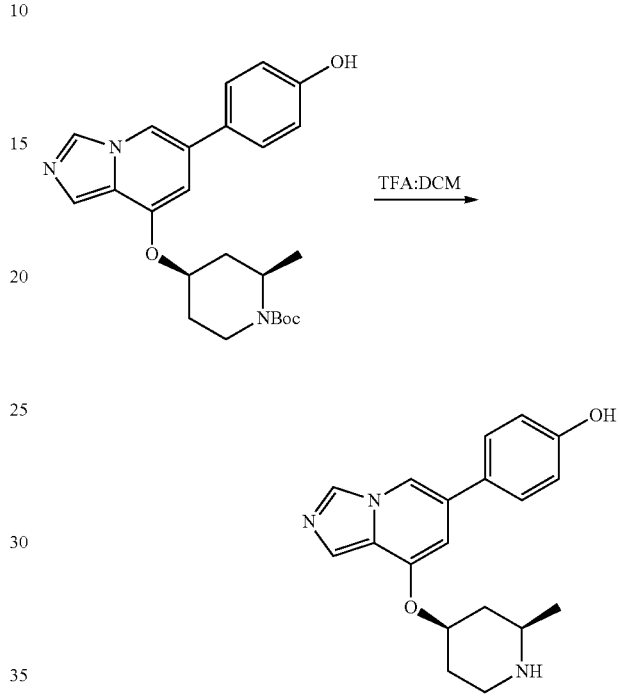

To a stirring solution of tert-butyl (2R,4R)-4-((6-(4-hydroxyphenyl)imidazo[1,5-a]pyridin-8-yl)oxy)-2-methylpiperidine-1-carboxylate in DCM (1.0 mL) was added TFA (1.0 mL) and the reaction was stirred at room temperature for 2 h. The reactions were then concentrated under reduced pressure to afford the desire product as a TFA salt (51 mg, 0.116 mmol). The crude product was used without any further purification. (m/z): [M+H]$^+$ calculated for C$_{19}$H$_{21}$N$_3$O$_2$ 324.1 found 324.2.

Example 15: 1-((2R,4R)-4-((6-(4-hydroxyphenyl)imidazo[1,5-a]pyridin-8-yl)oxy)-2-methylpiperidin-1-yl)prop-2-en-1-one

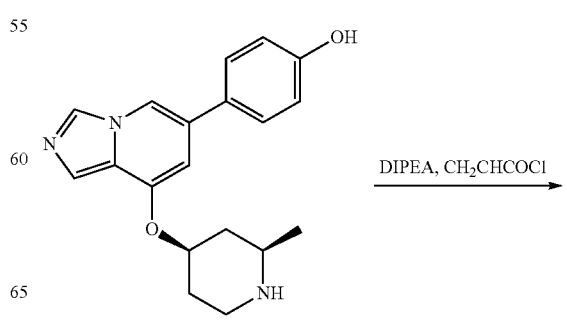

-continued

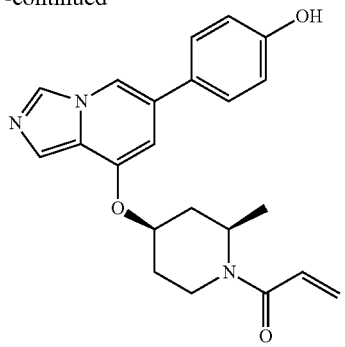

To a solution of 4-(8-(((2R,4R)-2-methylpiperidin-4-yl)oxy)imidazo[1,5-a]pyridin-6-yl)phenol (51 mg, 0.117 mmol) in DMF (585 μL) was added DIPEA (123 μL, 0.702 mmol) and then acryloyl chloride (7.6 μl, 0.094 mmol) dropwise. The reaction was stirred for 5 minutes and then concentrated in vacuo. The crude material was dissolved in ~1:1 AcOH:H$_2$O and purified using a 10-50% MeCN:H$_2$O (with 0.1% TFA) gradient on a Phenomenex 21.2×250 mm Luna Axia C18 column to afford the desired product as a TFA salt (7.8 mg, 0.021 mmol). (m/z): [M+H]$^+$ calculated for C$_{22}$H$_{23}$N$_3$O$_3$ 478.1 found 478.0.

Compounds 16 to 52 in Table 1 were prepared by similar synthetic methods using the appropriate starting materials.

TABLE 1

| Ex No. | Structure | Calculated [M + H]$^+$ | Found [M + H]$^+$ |
|---|---|---|---|
| 16 | 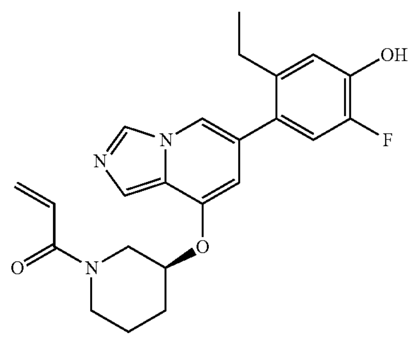 [SMILES: C=CC(=O)N1CCC[C@H](Oc2cc(-c3cc(F)c(O)cc3CC)cn3cncc23)C1] | 410.17 | 410.0 |
| 17 | 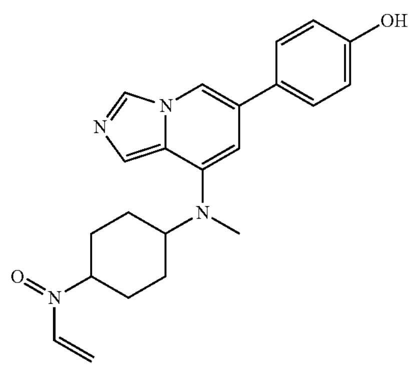 | 377.18 | 377.1 |
| 18 | 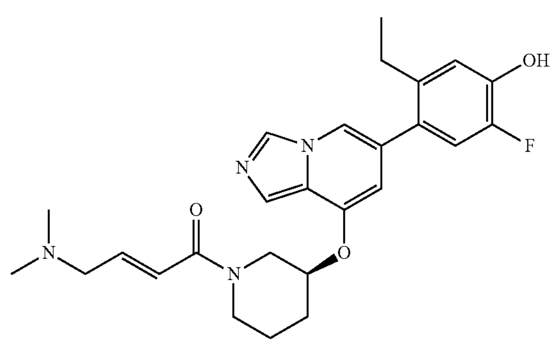 [SMILES: CCc1cc(O)c(F)cc1-c1cc(O[C@H]2CCCN(C(=O)/C=C/CN(C)C)C2)c2cncn2c1] | 467.23 | 467.0 |

TABLE 1-continued
| Ex No. | Structure | Calculated [M + H]+ | Found [M + H]+ |
|---|---|---|---|
| 19 | 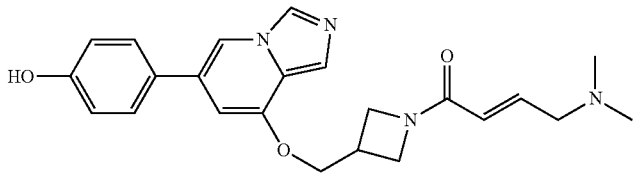 [SMILES: CN(C)C/C=C/C(=O)N1CC(COc2cc(-c3ccc(O)cc3)cn3cncc23)C1] | 407.19 | 407.2 |
| 20 | 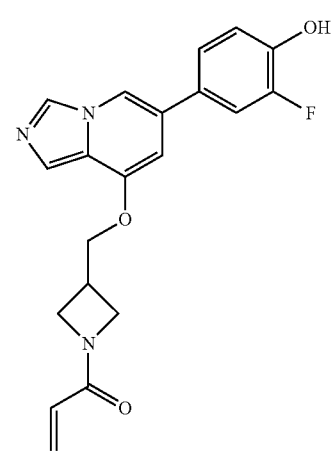 [SMILES: C=CC(=O)N1CC(COc2cc(-c3ccc(O)c(F)c3)cn3cncc23)C1] | 368.13 | 368.1 |
| 21 | 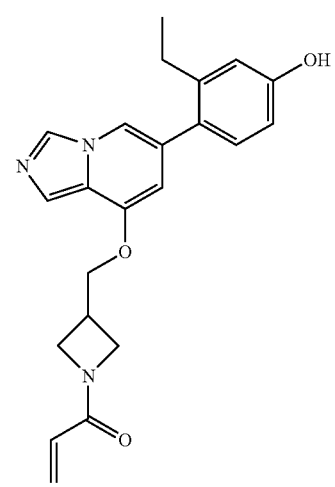 [SMILES: C=CC(=O)N1CC(COc2cc(-c3ccc(O)cc3CC)cn3cncc23)C1] | 378.17 | 378.2 |

TABLE 1-continued

| Ex No. | Structure | Calculated [M + H]+ | Found [M + H]+ |
|---|---|---|---|
| 22 | 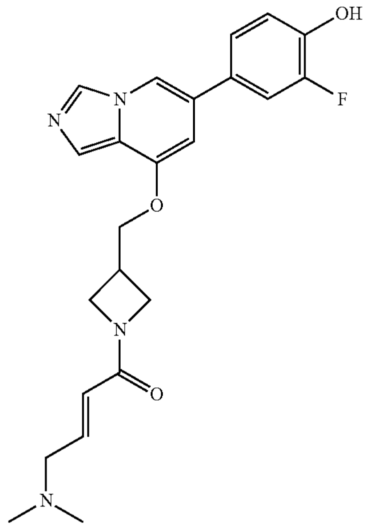 [SMILES: CN(C)C/C=C/C(=O)N1CC(COc2cc(-c3ccc(O)c(F)c3)cn3cncc23)C1] | 425.18 | 425.2 |
| 23 | 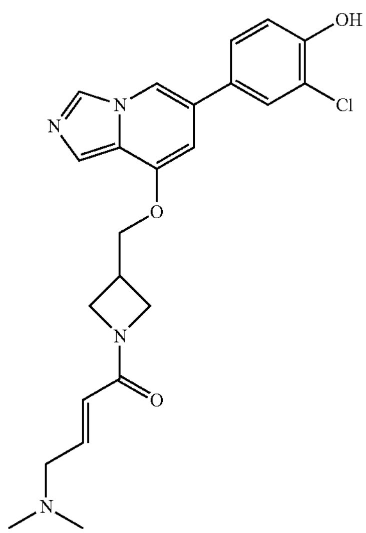 [SMILES: CN(C)C/C=C/C(=O)N1CC(COc2cc(-c3ccc(O)c(Cl)c3)cn3cncc23)C1] | 441.15 | 441.1 |
| 24 | 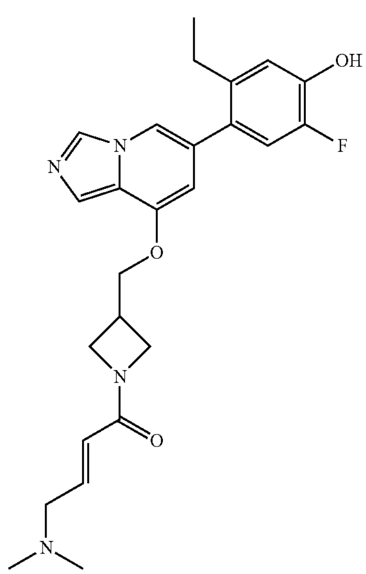 [SMILES: CCc1cc(O)c(F)cc1-c1cc(OCC2CN(C(=O)/C=C/CN(C)C)C2)c2cncn2c1] | 453.21 | 453.2 |

TABLE 1-continued

| Ex No. | Structure | Calculated [M + H]+ | Found [M + H]+ |
|---|---|---|---|
| 25 | 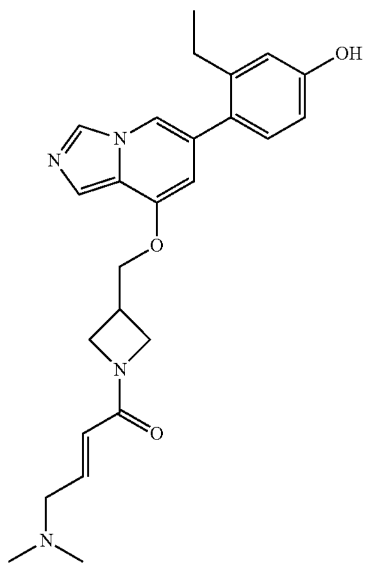 [SMILES: CCc1cc(O)ccc1-c1cc(OCC2CN(C(=O)/C=C/CN(C)C)C2)c2cncn2c1] | 435.22 | 435.2 |
| 26 | 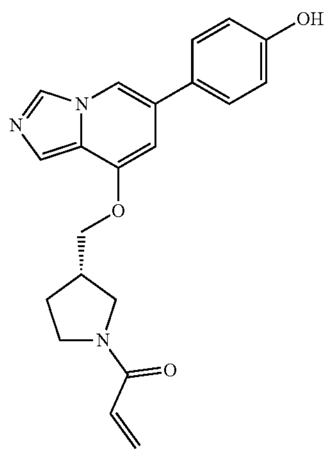 [SMILES: C=CC(=O)N1CC[C@H](COc2cc(-c3ccc(O)cc3)cn3cncc23)C1] | 364.15 | 364.2 |
| 27 | 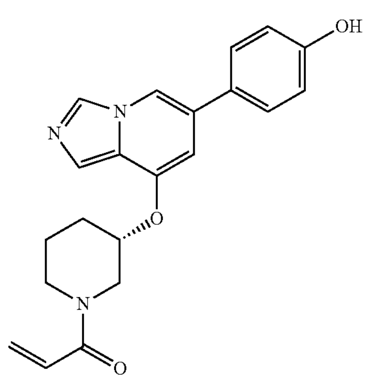 [SMILES: C=CC(=O)N1CCC[C@H](Oc2cc(-c3ccc(O)cc3)cn3cncc23)C1] | 364.15 | 364.1 |

TABLE 1-continued
| Ex No. | Structure | Calculated [M + H]+ | Found [M + H]+ |
|---|---|---|---|
| 28 | 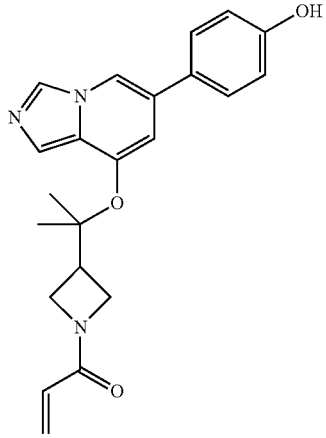 [SMILES: C=CC(=O)N1CC(C(C)(C)Oc2cc(-c3ccc(O)cc3)cn3cncc23)C1] | 378.17 | 378.1 |
| 29 | 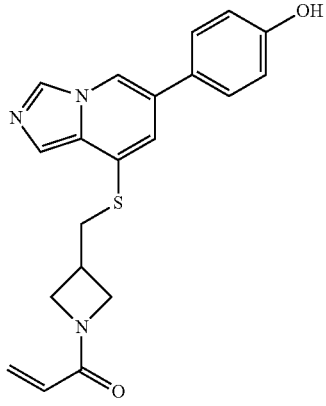 [SMILES: C=CC(=O)N1CC(CSc2cc(-c3ccc(O)cc3)cn3cncc23)C1] | 366.11 | 366.1 |
| 30 | 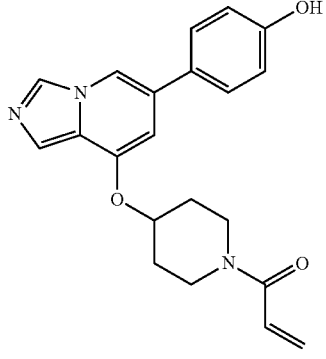 [SMILES: C=CC(=O)N1CCC(Oc2cc(-c3ccc(O)cc3)cn3cncc23)CC1] | 364.15 | 364.1 |

TABLE 1-continued

| Ex No. | Structure | Calculated [M + H]+ | Found [M + H]+ |
| --- | --- | --- | --- |
| 31 | 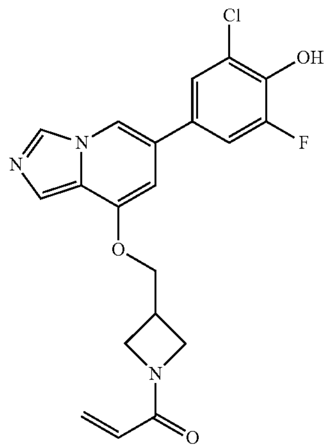 | 402.09 | 402.0 |
| 32 | 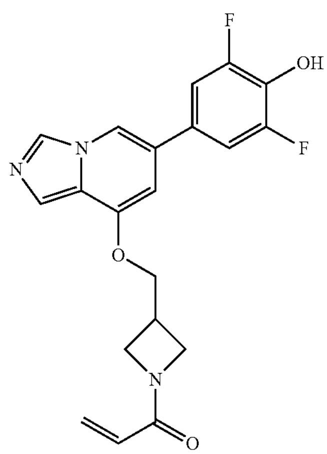 [SMILES: C=CC(=O)N1CC(COc2cc(-c3cc(F)c(O)c(F)c3)cn3cncc23)C1] | 386.12 | 386.1 |
| 33 | 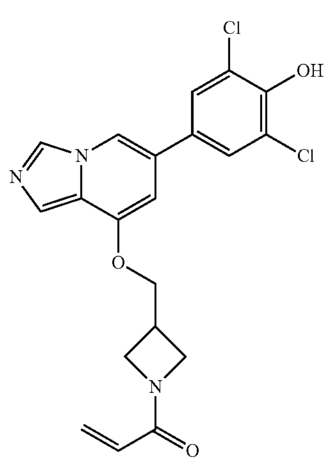 [SMILES: C=CC(=O)N1CC(COc2cc(-c3cc(Cl)c(O)c(Cl)c3)cn3cncc23)C1] | 148.06 | 418.0 |

TABLE 1-continued

| Ex No. | Structure | Calculated [M + H]+ | Found [M + H]+ |
|---|---|---|---|
| 34 | 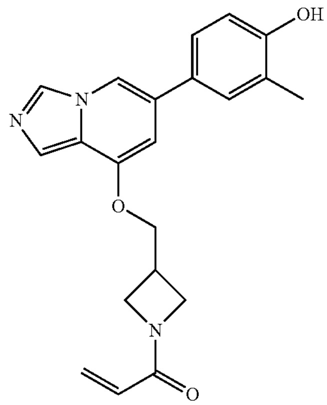 [SMILES: C=CC(=O)N1CC(COc2cc(-c3ccc(O)c(C)c3)cn3cncc23)C1] | 364.15 | 364.1 |
| 35 | 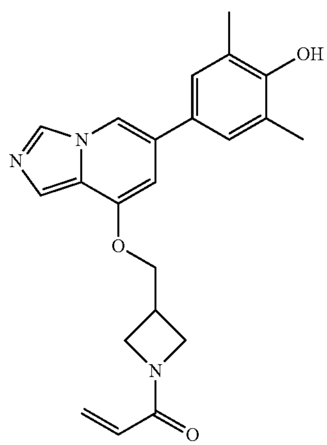 [SMILES: C=CC(=O)N1CC(COc2cc(-c3cc(C)c(O)c(C)c3)cn3cncc23)C1] | 378.17 | 378.1 |
| 36 | 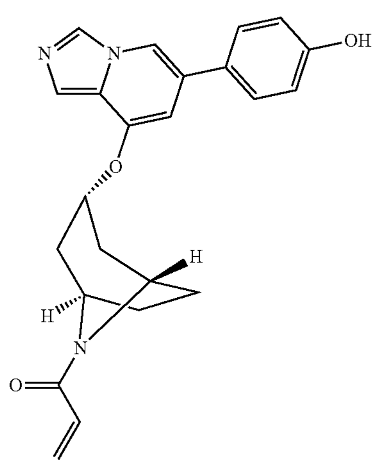 [SMILES: C=CC(=O)N1[C@@H]2CC[C@H]1C[C@@H](Oc1cc(-c3ccc(O)cc3)cn3cncc13)C2] | 390.17 | 390.1 |

TABLE 1-continued

| Ex No. | Structure | Calculated [M + H]+ | Found [M + H]+ |
|---|---|---|---|
| 37 | 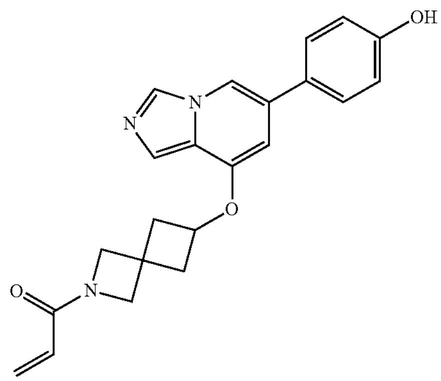 [SMILES: C=CC(=O)N1CC2(CC(Oc3cc(-c4ccc(O)cc4)cn4cncc34)C2)C1] | 376.15 | 376.1 |
| 38 | 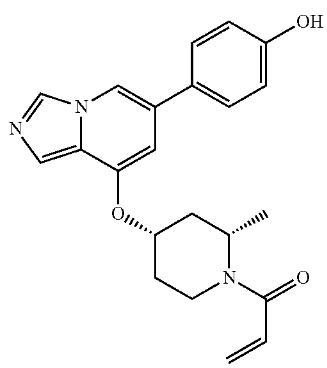 [SMILES: C=CC(=O)N1CC[C@H](Oc2cc(-c3ccc(O)cc3)cn3cncc23)C[C@@H]1C] | 378.17 | 378.0 |
| 39 | 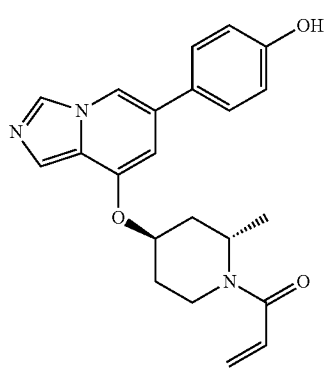 [SMILES: C=CC(=O)N1CC[C@@H](Oc2cc(-c3ccc(O)cc3)cn3cncc23)C[C@@H]1C] | 378.17 | 378.1 |
| 40 | 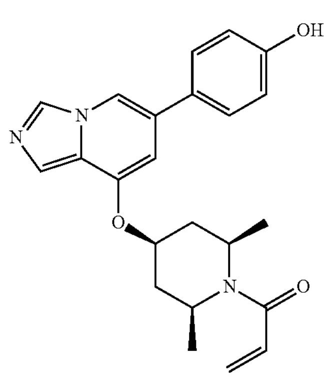 [SMILES: C=CC(=O)N1[C@H](C)C[C@H](Oc2cc(-c3ccc(O)cc3)cn3cncc23)C[C@@H]1C] | 392.18 | 392.1 |

TABLE 1-continued
| Ex No. | Structure | Calculated [M + H]+ | Found [M + H]+ |
|---|---|---|---|
| 41 | 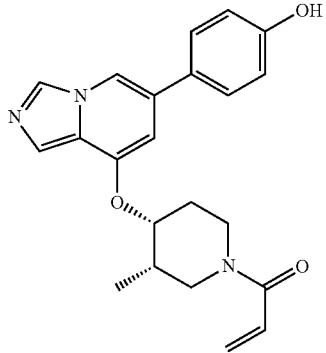 [SMILES: C=CC(=O)N1CC[C@@H](Oc2cc(-c3ccc(O)cc3)cn3cncc23)[C@@H](C)C1] | 378.17 | 378.1 |
| 42 | 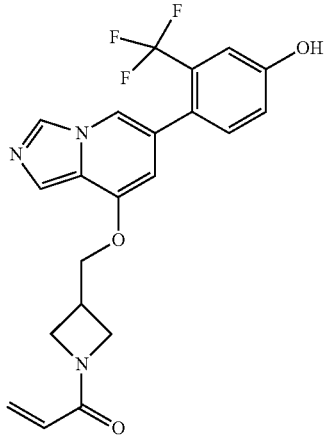 [SMILES: C=CC(=O)N1CC(COc2cc(-c3ccc(O)cc3C(F)(F)F)cn3cncc23)C1] | 418.12 | 418.0 |
| 43 | 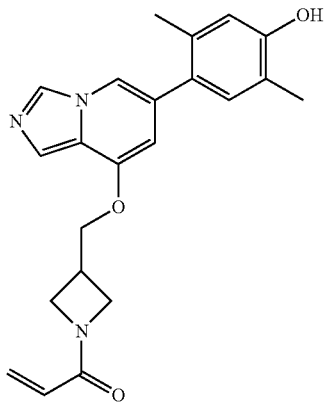 [SMILES: C=CC(=O)N1CC(COc2cc(-c3cc(C)c(O)cc3C)cn3cncc23)C1] | 378.17 | 378.0 |

TABLE 1-continued

| Ex No. | Structure | Calculated [M + H]+ | Found [M + H]+ |
|---|---|---|---|
| 44 | 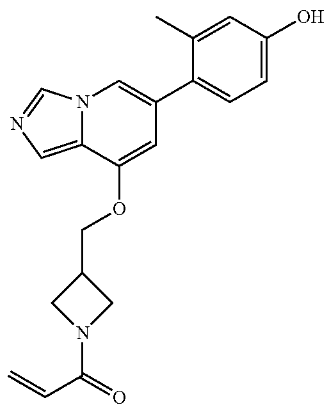 [SMILES: C=CC(=O)N1CC(COc2cc(-c3ccc(O)cc3C)cn3cncc23)C1] | 364.15 | 364.0 |
| 45 | 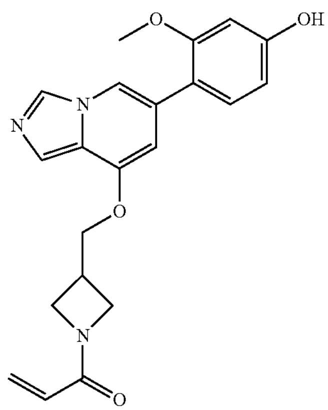 [SMILES: C=CC(=O)N1CC(COc2cc(-c3ccc(O)cc3OC)cn3cncc23)C1] | 380.15 | 380.0 |
| 46 | 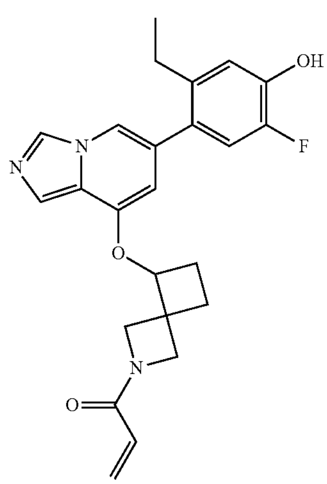 [SMILES: C=CC(=O)N1CC2(CCC2Oc2cc(-c3cc(F)c(O)cc3CC)cn3cncc23)C1] | 422.17 | 422.2 |

TABLE 1-continued
| Ex No. | Structure | Calculated [M + H]+ | Found [M + H]+ |
|---|---|---|---|
| 47 | 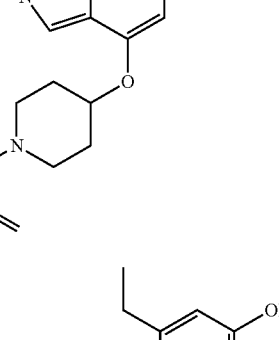 | 410.17 | 410.2 |
| 48 | 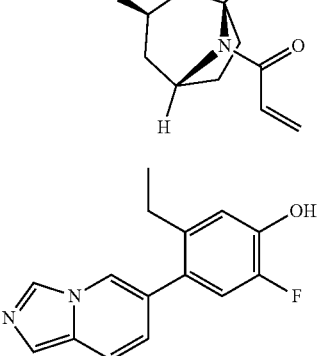 | 436.19 | 436.1 |
| 49 | 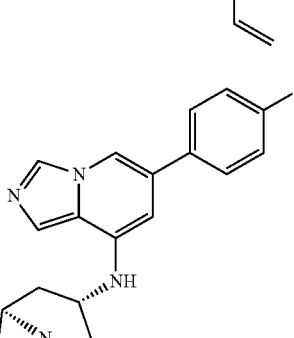 | 446.15 | 446.1 |
| 50 | 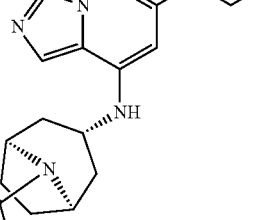 | 389.17 | 389.2 |

TABLE 1-continued

| Ex No. | Structure | Calculated [M + H]+ | Found [M + H]+ |
|---|---|---|---|
| 51 | 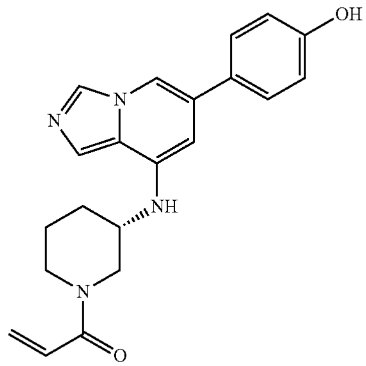 [SMILES: C=CC(=O)N1CCC[C@H](Nc2cc(-c3ccc(O)cc3)cn3cncc23)C1] | 363.16 | 363.2 |
| 52 | 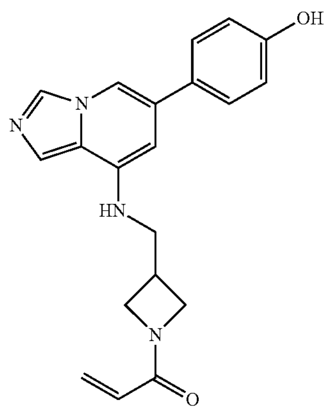 [SMILES: C=CC(=O)N1CC(CNc2cc(-c3ccc(O)cc3)cn3cncc23)C1] | 349.39 | 349.2 |

Biological Assays

The compounds of the disclosure have been characterized in one or more of the following biological assays.

Assay 1: Biochemical JAK and Tyk2 Kinase Assays

A panel of four LanthaScreen JAK biochemical assays (JAK1, 2, 3 and Tyk2) were carried in a common kinase reaction buffer (50 mM HEPES, pH 7.5, 0.01% Brij-35, 10 mM $MgCl_2$, and 1 mM EGTA). Recombinant GST-tagged JAK enzymes and a GFP-tagged STAT1 peptide substrate were obtained from Life Technologies.

Serially or discretely diluted compounds were pre-incubated with each of the four JAK enzymes and the substrate in white 384-well microplates (Corning) at ambient temperature for 1 h. ATP was subsequently added to initiate the kinase reactions in 10 μL total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 μL, 3 μM, 1.6 μL, and 10 μL; while the substrate concentration is 200 nM for all four assays. Kinase reactions were allowed to proceed for 1 hour at ambient temperature before a 10 μL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1 h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software (GraphPad Software). Results were expressed as $pIC_{50}$ (negative logarithm of $IC_{50}$) and subsequently converted to pKi (negative logarithm of dissociation constant, Ki) using the Cheng-Prusoff equation.

Assay 2: Cellular JAK3 Potency Assay: Inhibition of IL-2 Stimulated pSTAT5 in Tall-1 T Cells The potency of test compounds for inhibition of interleukin-2 (IL-2) stimulated STAT5 phosphorylation was measured in the Tall-1 human T cell line (DSMZ) using AlphaLisa. Because IL-2 signals through JAK3, this assay provides a measure of JAK3 cellular potency.

Phosphorylated STAT5 was measured via the AlphaLISA SureFire Ultra pSTAT5 (Tyr694/699) kit (PerkinElmer).

Human T cells from the Tall-1 cell line were cultured in a 37° C., 5% $CO_2$ humidified incubator in RPMI (Life Technologies) supplemented with 15% Heat Inactivated Fetal Bovine Serum (FBS, Life Technologies), 2 mM Glutamax (Life Technologies), 25 mM HEPES (Life Technologies) and 1× Pen/Strep (Life Technologies). Compounds were serially diluted in DMSO and dispensed acoustically to empty wells. Assay media (phenol red-free DMEM (Life Technologies) supplemented with 10% FBS (ATCC)) was dispensed (4 μL/well) and plates shaken at 900 rpm for 10 mins. Cells were seeded at 45,000 cells/well in assay media (4 μL/well), and incubated at 37° C., 5% $CO_2$ for 1 hour, followed by the addition of IL-2 (R&D Systems; final concentration 300 ng/ml) in pre-warmed assay media (4 ΞL) for 30 minutes. After cytokine stimulation, cells were lysed with 6 ul of 3× AlphaLisa Lysis Buffer (PerkinElmer)

containing 1× PhosStop and Complete tablets (Roche). The lysate was shaken at 900 rpm for 10 minutes at room temperature (RT). Phosphorylated STAT5 was measured via the pSTAT5 AlphaLisa kit (PerkinElmer). Freshly prepared acceptor bead mixture was dispensed onto lysate (5 µL) under green filtered <100 lux light. Plates were shaken at 900 rpm for 2 mins, briefly spun down, and incubated for 2 hrs at RT in the dark. Donor beads were dispensed (5 µL) under green filtered <100 lux light. Plates were shaken at 900 rpm for 2 minutes, briefly spun down, and incubated overnight at RT in the dark. Luminescence was measured with excitation at 689 nm and emission at 570 nm using an EnVision plate reader (PerkinElmer) under green filtered <100 lux light.

To determine the inhibitory potency of test compounds in response to IL-2, the average emission intensity of beads bound to pSTAT5 was measured in a human T cell line. $IC_{50}$ values were determined from analysis of the inhibition curves of signal intensity versus compound concentration. Data are expressed as $pIC_{50}$ (negative decadic logarithm $IC_{50}$) values (mean±standard deviation).

Assay 3: Inhibition of IL-2 Stimulated pSTAT5 in CD4+ T Cells Isolated from Murine Splenocytes The potency of test compounds for inhibition of interleukin-2 (IL-2) stimulated STAT5 phosphorylation was measured in the CD4+ T cells isolated from murine splenocytes using AlphaLisa. Because IL-2 signals through JAK3, this assay provides a measure of JAK3 cellular potency in mouse.

Phosphorylated STAT5 was measured via the AlphaLISA SureFire Ultra pSTAT5 (Tyr694/699) kit (PerkinElmer).

CD4+ T cells were isolated from murine splenocytes via negative selection on a magnetic column (Miltnyi Biotec) and re-suspended in assay media (phenol red-free DMEM (Life Technologies) supplemented with 10% FBS (ATCC)). Cells were seeded at 50,000 cells/well in assay media (2 µL/well). Compounds were serially diluted in DMSO and diluted to 2× final concentration in assay media. Compound was added (4 µl/well) and the cells incubated at 37° C., 5% $CO_2$ for 1 hour, followed by the addition of IL-2 (R&D Systems; final concentration 7 ng/ml) in pre-warmed assay media (2 µL) for 30 minutes. After cytokine stimulation, cells were lysed with 2 µl of 5× AlphaLisa Lysis Buffer (PerkinElmer). The lysate was shaken at 900 rpm for 10 minutes at room temperature (RT). Phosphorylated STAT5 was measured via the pSTAT5 AlphaLisa kit (PerkinElmer). Freshly prepared acceptor bead mixture was dispensed onto lysate (5 ul) under green filtered <100 lux light. Plates were shaken at 900 rpm for 2 mins, briefly spun down, and incubated for 2 hrs at RT in the dark. Donor beads were dispensed (5 µl) under green filtered <100 lux light. Plates were shaken at 900 rpm for 2 mins, briefly spun down, and incubated overnight at RT in the dark. Luminescence was measured with excitation at 689 nm and emission at 570 nm using an EnVision plate reader (PerkinElmer) under green filtered <100 lux light.

To determine the inhibitory potency of test compounds in response to IL-2, the average emission intensity of beads bound to pSTAT5 was measured in primary CD4+ T cells isolated from murine splenocytes. $IC_{50}$ values were determined from analysis of the inhibition curves of signal intensity vs compound concentration. Data are expressed as $pIC_{50}$ (negative decadic logarithm $IC_{50}$) values (mean±standard deviation).

Compounds 7, 8, 9, 11, 12, 13, 15, 20, 24, 28, 31, and 34 all had $pIC_{50}$ values over 6.0 in this assay.

Assay 4: JAK Cytotoxicity Assay

A CellTiter-Glo luminescent cell viability/cytotoxicity assay was carried out in BEAS-2B human lung epithelial cells (ATCC) under the normal growth condition.

Cells were grown at 37° C. in a 5% $CO_2$ humidified incubator in 50% DMEM/50% F-12 medium (Life Technologies) supplemented with 10% FBS (Hyclone), 100 U/mL penicillin, 100 µg/mL streptomycin (Life Technologies), and 2 mM GlutaMAX (Life Technologies). On day 1 of the assay, cells were seeded at a 500 cells/well density in white 384-well tissue culture plates (Corning) with 25 µL medium, and were allowed to adhere overnight in the incubator. On day 2 of the assay, 5 µL of medium containing dose-responses of test compounds was added, and incubated at 37° C. for 48 h. 30 µL of CellTiter-Glo detection solution (Promega) was subsequently added, mixed on an orbital shaker for 5 min, and incubated for additional 10 min before being read on the EnVision reader. Luminescence signals were recorded and percent DMSO control values were calculated.

For dose-response analysis, percent DMSO control data were plotted vs. compound concentrations to derive dose-response curves by line connecting each data point. The concentration at which each curve crosses the 15% inhibition threshold is defined as $CC_{15}$. Results were expressed as the negative logarithm of the $CC_{15}$ value, $pCC_{15}$.

It is expected that test compounds exhibiting a lower $pCC_{15}$ value in this assay have less likelihood to cause cytotoxicity. Compounds of the disclosure tested in this assay typically exhibited $pCC_{15}$ values between 5 and about 6.

Assay 5: Caco-2 Permeation Assay

The Caco-2 permeation assay was performed to model the ability of test compounds to pass through the intestine and get into the blood stream after oral administration. The rate at which test compounds in solution permeate a cell monolayer designed to mimic the tight junction of human small intestinal monolayers was determined.

CacoReady 24-well transwell plates were obtained from ADMEcell (Alameda, Calif.). The compounds were evaluated at a concentration of 5 µM from 10 mM DMSO stock solutions in duplicate (n=2). The passive permeability of the compounds tested was evaluated using Caco-2 cell monolayers along with Verapamil (25 µM) to inhibit P-gp transport proteins in the apical to basolateral (A-B) direction. The experiment was conducted in a 37° C., 5% $CO_2$ incubator. Caco-2 culture media consisted of standard filtered DMEM, FCS 10%, L-Glutamine 1% and PenStrep 1%. Basal assay plate was prepared by adding 750 µL, of transport buffer to A-B wells. A CacoReady™ plate was prepared by removing the Caco-2 media from the apical wells and replacing with fresh transport media (200 µL repeated for a total of 3 washes). Blank media (200 µL) was then replaced with diluted compound for A-B wells. To begin the incubation, the basal plate was removed from the incubator and the apical section was added on top of it. Samples (40 µL) were collected from the apical and basal compartments for time zero (t0). Samples were collected again after 120 minutes (t120) from the apical and basal compartments. All samples were diluted and prepared for bioanalysis by LC-MS/MS. The permeation coefficient ($K_p$, mean A to B+Verapamil Papparent) in cm/sec was calculated as dQ (flux)/(dt×Area× concentration).

In this assay, a $K_p$ value less than approximately $5 \times 10^{-6}$ cm/sec is considered favorable to minimize systemic exposure and target the colon. A $K_p$ value less than approximately $10 \times 10^{-6}$ cm/sec may also be sufficient to minimize systemic exposure and target the colon. By comparison, PF-06651600, a JAK3 inhibitor available systemically (2-propen-1-one, 1-[(2S,5R)-2-methyl-5-(7H-pyrrolo[2,3]pyrimidin-4-ylamino)-1-piperidinyl]) exhibited a Kp value of 25.

In Vitro Assay Results

All of the compounds of Examples 1 to 52 were tested in one or more of the assays described above.

In Table 2 below, for the JAK1, JAK 2, JAK3, and TYK2 enzyme assays, A represents a $pK_i$ value≥10 ($K_i$≤0.1 nM), B represents a $pK_i$ value between 9 and 10 ($K_i$ between 1 nM and 0.1 nM), C represents a $pK_i$ value between 8 and 9 ($K_i$ between 10 nM and 1 nM), D represents a $pK_i$ value between 7 and 8 ($K_i$ between 100 nM and 10 nM), and E represents a $pK_i$ value of 7 or below ($K_i$ of 100 nM or above). For the Tall-1 Potency assay, A represents a $pIC_{50}$ value ≥7.5 ($IC_{50}$≤32 nM), B represents a $pIC_{50}$ value between 6.7 (included) and 7.5 ($IC_{50}$ between 200 nM and 32 nM), and C represents a $pIC_{50}$ value between 6 and 6.7 ($IC_{50}$ between 1 μM and 200 nM). For the JAK3 (pKi)-JAK1 (pKi) values, A represents a value of 3 or above, B represents a value of 2.3 to 3 and C represents a value of 1.8 to 2.3. For the Caco assay, A represents a value below $5\times10^{-6}$ cm/sec, B represents a value between $5\times10^{-6}$ and $10\times10^{-6}$ cm/sec, C represents a value between $10\times10^{-6}$ and $25\times10^{-6}$ cm/sec.

TABLE 2

| Ex No. | JAK 1 (pKi) | JAK 2 (pKi) | JAK 3 (pKi) | Tyk 2 (pKi) | Tall-1 ($pIC_{50}$) | JAK3 (pKi)-JAK1 (pKi) | Caco $K_p$ $10^{-6}$ cm/sec |
|---|---|---|---|---|---|---|---|
| 1 | E | E | B | E | C | A | |
| 2 | E | E | B | E | C | A | C |
| 3 | E | E | B | E | B | A | |
| 4 | E | E | C | E | | B | |
| 5 | E | | A | | C | A | |
| 6 | E | E | B | E | B | A | B |
| 7 | E | E | B | E | B | A | B |
| 8 | E | E | A | E | B | A | B |
| 9 | E | E | B | E | B | A | A |
| 10 | E | E | A | E | B | A | |
| 11 | E | E | B | E | B | A | A |
| 12 | E | E | B | E | B | A | A |
| 13 | E | E | B | E | A | A | A |
| 14 | E | D | A | E | A | A | B |
| 15 | E | D | A | E | A | A | |
| 16 | D | D | B | E | B | B | C |
| 17 | E | | C | | | B | |
| 18 | E | | B | | | B | |
| 19 | E | | B | | C | A | |
| 20 | E | E | B | E | B | A | A |
| 21 | E | E | B | E | B | A | B |
| 22 | E | | B | | C | A | |
| 23 | E | E | B | E | C | A | |
| 24 | E | E | A | E | B | A | A |
| 25 | E | | B | | C | A | |
| 26 | E | E | B | E | B | A | |
| 27 | E | E | B | E | C | A | |
| 28 | E | E | A | E | B | A | A |
| 29 | E | | B | | C | A | |
| 30 | E | E | A | E | B | A | C |
| 31 | E | E | A | E | B | A | A |
| 32 | E | | B | | C | A | |
| 33 | E | | A | | B | A | A |
| 34 | E | E | B | E | B | A | B |
| 35 | E | | B | | C | A | |
| 36 | E | | A | | B | A | |
| 37 | E | E | B | E | C | A | |
| 38 | E | | B | | B | A | |
| 39 | E | E | A | E | B | A | |
| 40 | E | | C | | C | B | |
| 41 | E | E | A | E | B | A | |
| 42 | E | | B | | C | A | |
| 43 | E | | B | | B | A | |

TABLE 2-continued

| Ex No. | JAK 1 (pKi) | JAK 2 (pKi) | JAK 3 (pKi) | Tyk 2 (pKi) | Tall-1 ($pIC_{50}$) | JAK3 (pKi)-JAK1 (pKi) | Caco $K_p$ $10^{-6}$ cm/sec |
|---|---|---|---|---|---|---|---|
| 44 | E | E | B | E | B | A | |
| 45 | E | | B | | C | A | |
| 46 | E | | B | | B | B | |
| 47 | D | | A | | A | B | |
| 48 | D | | A | | A | A | |
| 49 | D | | 10 | | A | C | |
| 50 | E | | C | | | B | |
| Si | E | | C | | | B | |
| 52 | E | | C | | | B | |

Assay 6: Colon and Plasma Mouse Pharmacokinetics 6 male Balb/c mice were administered 10 mg/kg of compound in 1% HPMC+0.1% Tween-80 by PO administration. At 0.5, 2 and 6 hours after dose administration, animals were anesthetized, and terminal blood samples were collected by cardiac puncture, followed by collection of colon contents and colon tissue.

Blood samples were collected into $K_2$EDTA and stored on wet ice until processed to plasma by centrifugation (12,000 rpm at 4° C.). Plasma samples were transferred to cluster tubes and placed on dry ice prior to freezer storage. The colon contents from each animal were collected at each terminal blood collection time point. The colon tissues were flushed with saline and patted dry. The colon and colon content tissues were homogenized using sterile water containing 0.1% formic acid 9:1 (water:tissue, v/w). The homogenized tissues and colon contents were transferred to cluster tubes and placed on dry ice prior to freezer storage. All samples were analyzed using LC/MS/MS against analytical standards.

The composite pharmacokinetic parameters of the compounds were determined by non-compartmental analysis using Phoenix WinNonlin Version 6 (Certara, St. Louis, Mo.) and using mean values from 2 animals/time point. For plasma concentrations below the quantification limit (BQL), the lowest concentration measurable or the BLOQ (below limit of quantification) was used.

A colon to plasma ratio was determined as the ratio of the colon AUC to the plasma AUC. Compounds 12, 13, 16, and 24 exhibited a colon to plasma ratio in excess of 200. Compound 15 exhibited a colon to plasma ratio in excess of 30. Compound 30 exhibited a colon to plasma ratio in excess of 8.

In contrast, the reference compound (PF-06651600, a JAK3 inhibitor available systemically) 2-propen-1-one, 1-[(2S,5R)-2-methyl-5-(7H-pyrrolo[2,3-d]pyrimidin-4-ylamino)-1-piperidinyl], exhibited a colon to plasma ratio of 2.8

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A compound of formula (I):

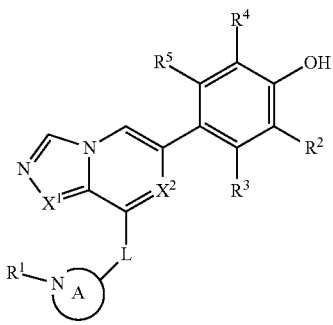

or a pharmaceutically acceptable salt thereof, wherein
$X^1$ and $X^2$ are each independently selected from N and CH;

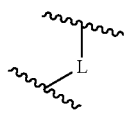

is selected from the group consisting of

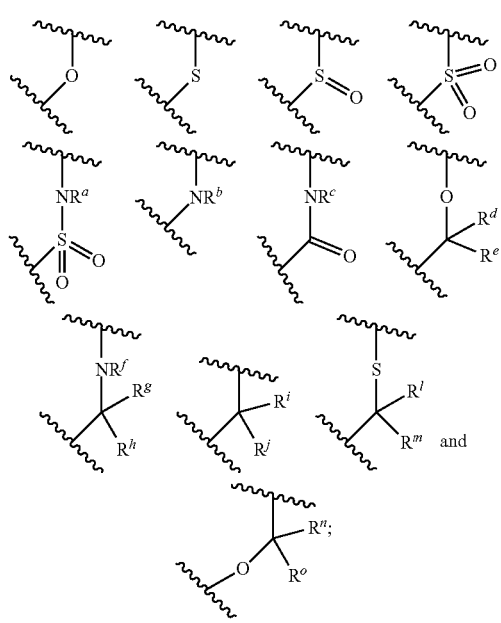

$R^a$, $R^b$, $R^c$, and $R^f$ are each independently selected from the group consisting of H and $C_{1-3}$ alkyl;
$R^d$, $R^e$, $R^g$, $R^h$, $R^i$, $R^j$, $R^l$, $R^m$, $R^n$ and $R^o$ are each independently selected from the group consisting of H and $C_{1-3}$ alkyl wherein the $C_{1-3}$ alkyl group may be optionally substituted with 1 to 3 halogens;
A is selected from the group consisting of
(a) a 4 to 8 membered monocyclic heterocyclic group containing one nitrogen atom and optionally containing one additional heteroatom selected from N, S, $S(O)_2$ and O, and
(b) a 6 to 10 membered multicyclic heterocyclic group containing one nitrogen atom and optionally containing one additional heteroatom selected from N, S, $S(O)_2$ and O,
wherein L is linked to a carbon atom in A and A is optionally substituted with 1 to 3 $R^k$ groups;
each $R^k$ is independently selected from the group consisting of F, CN, $C_{1-3}$ alkoxy, and $C_{1-3}$ alkyl, wherein the $C_{1-3}$ alkyl group may be optionally substituted with OH, OMe or 1 to 3 halogens;
$R^1$ is selected from the group consisting of:

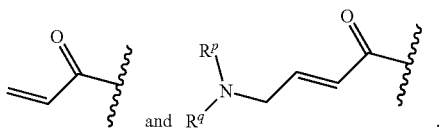

wherein $R^p$ and $R^q$ are each independently selected from the group consisting of H, $C_{3-5}$ cycloalkyl and $C_{1-6}$ alkyl;
$R^2$ is selected from the group consisting of H, Cl, OMe, Me and F;
$R^3$ is selected from the group consisting of H, Me, Et, $CF_3$, OMe, and F;
$R^4$ is selected from the group consisting of H, Me, OMe, Cl, and F; and
$R^5$ is selected from the group consisting of H, Me, Et, and F.

2. The compound of claim 1, or a pharmaceutically acceptable salt thereof, having the Formula (II):

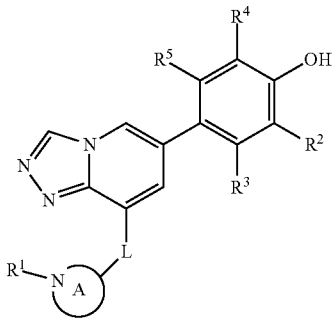

3. The compound of claim 1, or a pharmaceutically acceptable salt thereof, having the Formula (III):

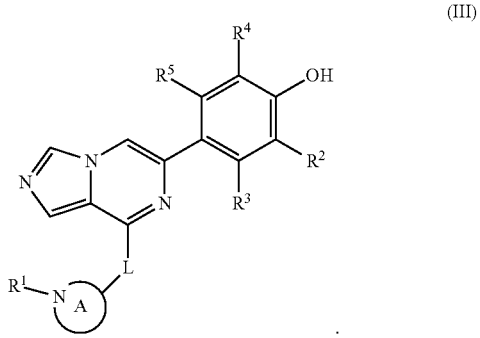

4. The compound of claim 1, or a pharmaceutically acceptable salt thereof, having the Formula (IV):

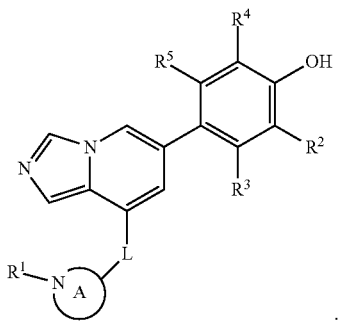

(IV)

5. The compound of claim 4, or a pharmaceutically acceptable salt thereof, wherein $R^1$ is selected from the group consisting of:

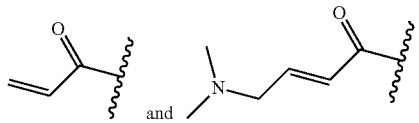

and

6. The compound of claim 4, or a pharmaceutically acceptable salt thereof, wherein $R^1$ is

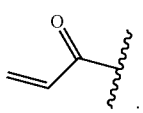

7. The compound of claim 6, or a pharmaceutically acceptable salt thereof, wherein A is selected from the group consisting of azetidine, pyrrolidine, piperidine, 2-azaspiro[3.3]heptane, and nortropane, wherein A is optionally substituted with 1 to 3 $R^k$ groups.

8. The compound of claim 6, or a pharmaceutically acceptable salt thereof, wherein A is selected from the group consisting of azetidine and piperidine, wherein A is optionally substituted with 1 to 3 $R^k$ groups.

9. The compound of claim 6, or a pharmaceutically acceptable salt thereof, wherein

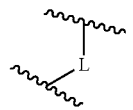

is selected from the group consisting of

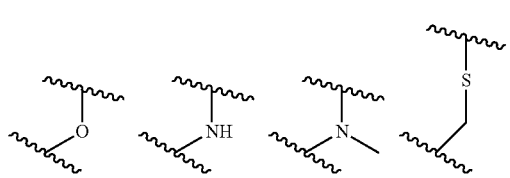

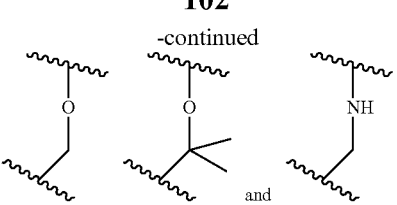

and

10. The compound of claim 6, or a pharmaceutically acceptable salt thereof, wherein

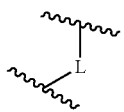

is selected from the group consisting of

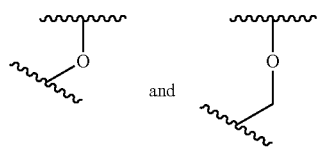

and

11. The compound of claim 6, or a pharmaceutically acceptable salt thereof, wherein

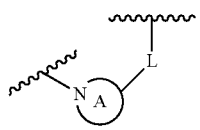

is selected from the group consisting of:

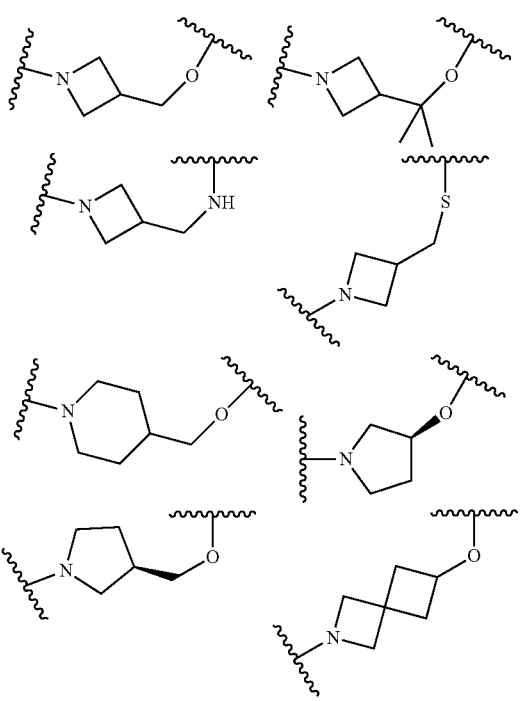

-continued
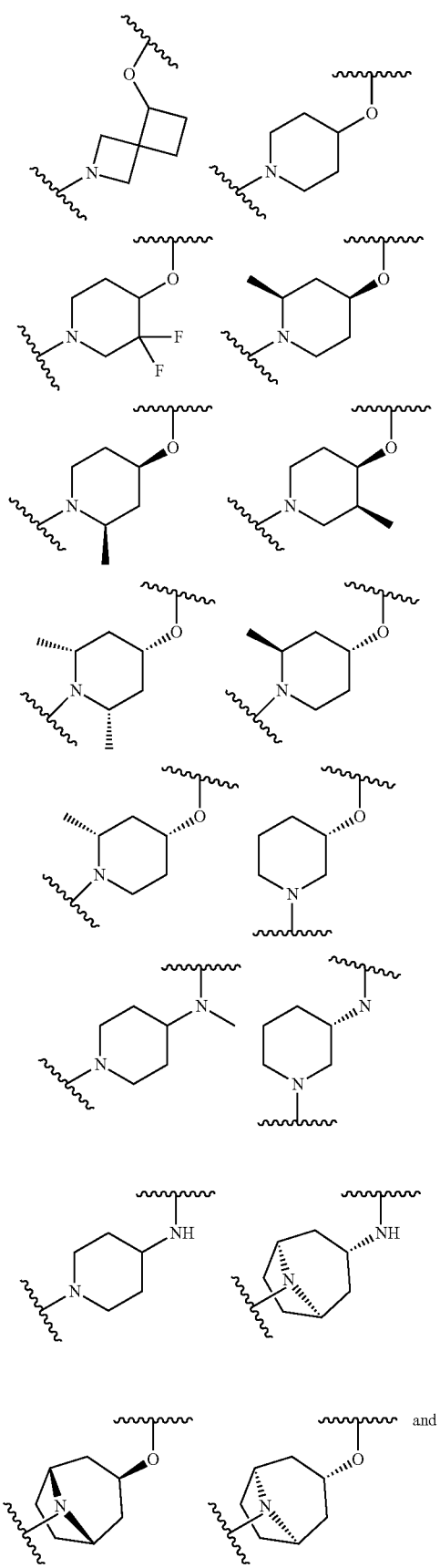
-continued
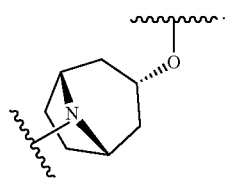
12. The compound of claim 6, or a pharmaceutically acceptable salt thereof, wherein
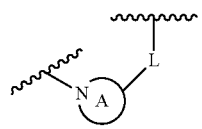
is selected from the group consisting of:
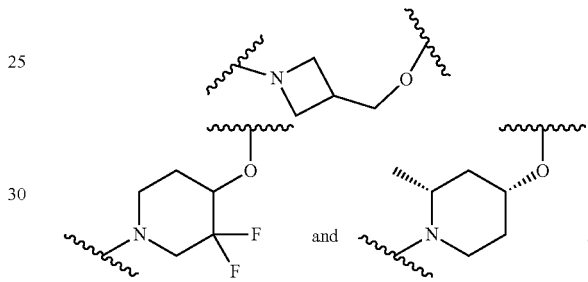
13. The compound of claim 6, or a pharmaceutically acceptable salt thereof, wherein
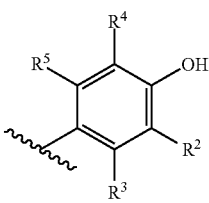
is selected from the group consisting of:
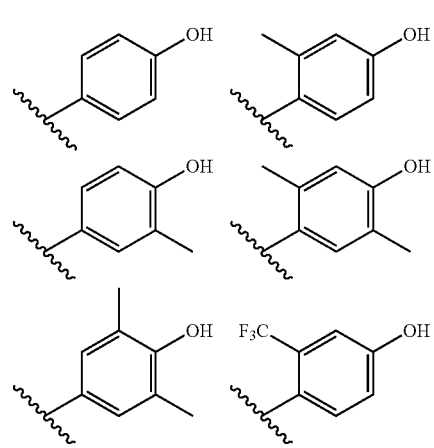

-continued

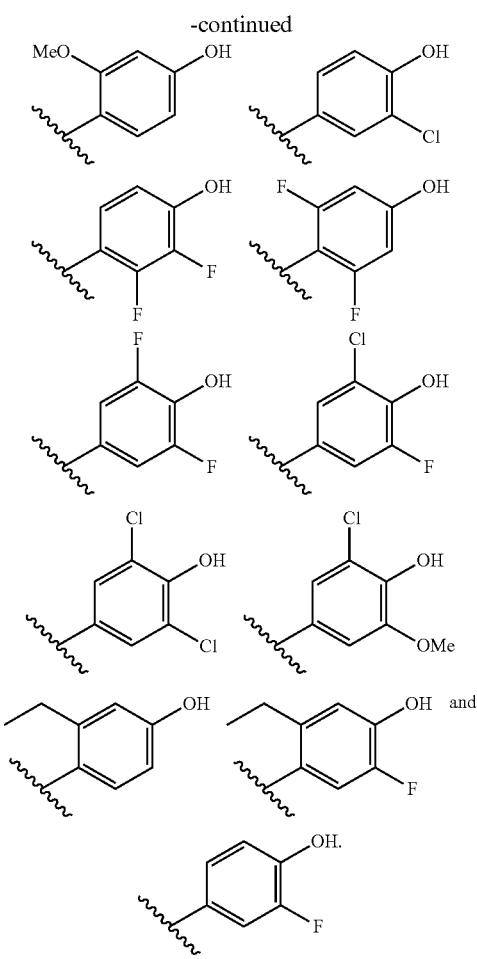

14. The compound of claim 6, or a pharmaceutically acceptable salt thereof, wherein

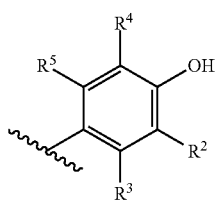

is selected from the group consisting of:

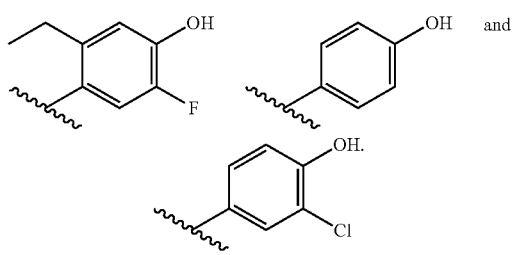

15. The compound of claim 4, or a pharmaceutically acceptable salt thereof, wherein

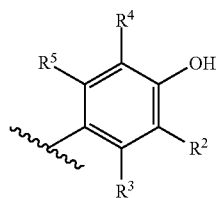

is selected from the group consisting of:

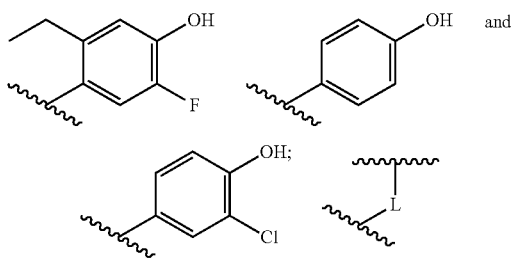

is selected from the group consisting of

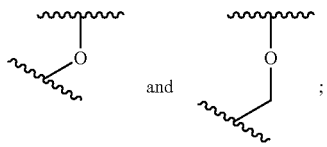

$R^1$ is

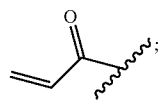

and

A is selected from the group consisting of azetidine and piperidine, wherein A is optionally substituted with 1 or 2 $R^k$ groups, wherein each $R^k$ is independently selected from the group consisting of methyl and fluoro.

16. The compound of claim 4, or a pharmaceutically acceptable salt thereof, wherein the compound is selected from the group consisting of:

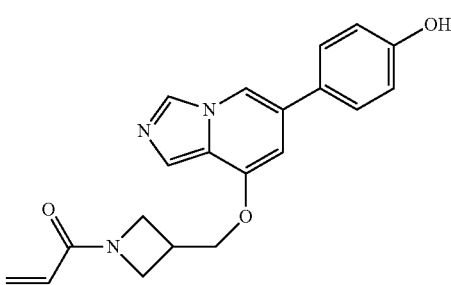

107
-continued

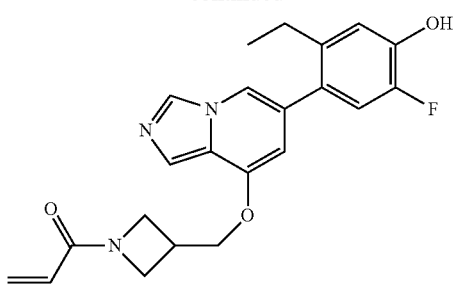 [SMILES: C=CC(=O)N1CC(COc2cc(-c3cc(F)c(O)cc3CC)cn3cncc23)C1]
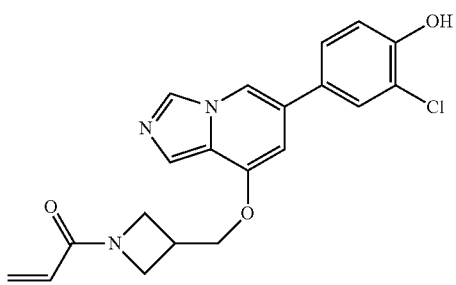
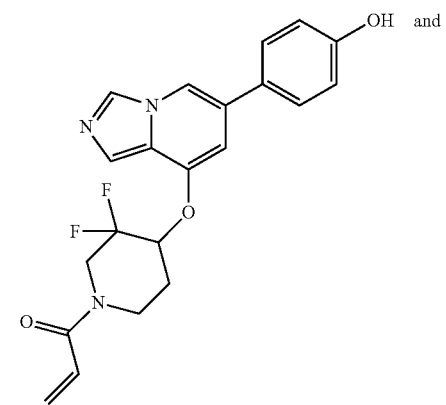

108
-continued

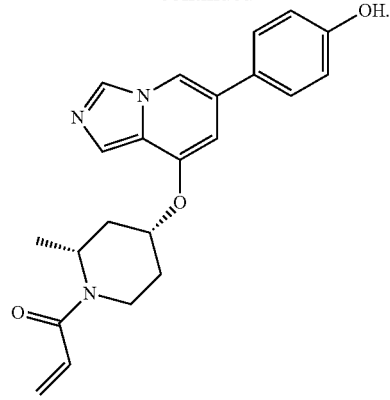

17. A pharmaceutical composition comprising a compound of claim 1, or a pharmaceutically acceptable salt thereof, and a pharmaceutically-acceptable carrier.

18. The pharmaceutical composition of claim 17, further comprising one or more other therapeutic agents useful for treating a gastrointestinal inflammatory disease.

19. A compound of formula:

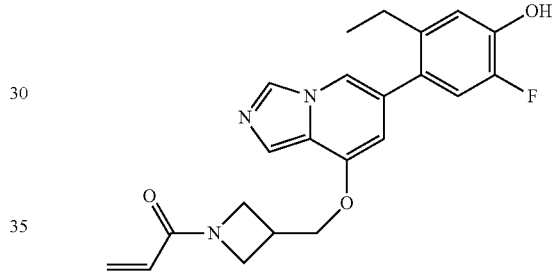

or a pharmaceutically acceptable salt thereof.

* * * * *